US007352466B2

(12) United States Patent
Cao et al.

(10) Patent No.: US 7,352,466 B2
(45) Date of Patent: Apr. 1, 2008

(54) GAS DETECTION AND PHOTONIC CRYSTAL DEVICES DESIGN USING PREDICTED SPECTRAL RESPONSES

(75) Inventors: Jiang-Rong Cao, Irvine, CA (US); Mamoru Miyawaki, Irvine, CA (US)

(73) Assignee: Canon Kabushiki Kaisha, Tokyo (JP)

(*) Notice: Subject to any disclaimer, the term of this patent is extended or adjusted under 35 U.S.C. 154(b) by 312 days.

(21) Appl. No.: 11/157,042

(22) Filed: Jun. 17, 2005

(65) Prior Publication Data
US 2006/0285114 A1    Dec. 21, 2006

(51) Int. Cl.
*G01N 21/00* (2006.01)
(52) U.S. Cl. ................................. 356/437
(58) Field of Classification Search ......... 356/432–444
See application file for complete search history.

(56) References Cited

U.S. PATENT DOCUMENTS

| 5,459,566 A | 10/1995 | Pearson et al. | 356/246 |
| 2005/0063633 A1* | 3/2005 | Shurgalin et al. | 385/12 |
| 2005/0110992 A1* | 5/2005 | Scherer et al. | 356/318 |

OTHER PUBLICATIONS

U. Fano, "Effects of Configuration Interaction On Intensities and Phase Shifts," Physical Review vol. 124, No. 6 (1961).
J. Stoer, R. Blirsch, "Introduction to Numerical Analysis," Springer-Verlag, New York (1980), particular §2.2.
W. H. Press, S. A. Teukolsky, W. t. Vetterling, B. P. Flannery, "Numerical Recipes in Fortran 77 (2nd Ed.)," Cambridge University Press, New York (1992), pp. 104-107; 113-116; and 194-197.
K. M. Ho, C. T. Chan, C. M. Soukoulis, R. Biswas, M. Sigalas, "Photonic Band Gaps in Three Dimension: New Layer-by-Layer Periodic Structures," Solid State Commun. 89(5), 413-6 (1994).
P. R. Villeneuve et al., "Microcavities in photonic crystals: Mode symmetry, tenability, and coupling efficiency," Phys. Rev. B 54(11), 7837 (1996).
Supriyo Dey, et al., "Efficient Computation of Resonant Frequencies and Quality Factors of Cavities via a Combination of the Finite-Difference Time-Domain Technique and the PadëApproximation", IEEE Microwave and Guided Wave Letters, vol. 8, No. 12, (1998).

(Continued)

Primary Examiner—Tarifur Chowdhury
Assistant Examiner—Jonathon D Cook
(74) Attorney, Agent, or Firm—Fitzpatrick, Cella, Harper & Scinto

(57) ABSTRACT

In detecting presence of a gas, light passes through a photonic crystal cavity configured to sample a gas and receive light. The light has a wavelength that at least partially falls within a specific absorption wavelength of the gas. At least one parameter of a band gap spectrum is generated from at least a portion of the light passing through the photonic crystal cavity. In generating the at least one parameter, a numerical simulation is performed within a frequency range of the photonic crystal cavity to generate a set of spectral response data points, rational function interpolation is performed on the set of spectral response data points to generate a spectral response, and at least one parameter is determined from the spectral response. The at least one parameter is compared with stored parameters of band gap spectrums, wherein a match indicates a presence and/or concentration of the gas.

31 Claims, 49 Drawing Sheets

OTHER PUBLICATIONS

S. Y. Lin, J. G. Fleming, D. L. Hetherington, B. K. Smith, R. Biswas, K. M. Ho, M. M. Sigalas, W. Zubrzycki, S. R. Kurtz, J. Bur, "A three-dimensional photonic crystal operating at infrared wavelengths," Nature 394, 251-3 (1998).

Andrew M. Girard, James R. Soltys, "Complex Tariff Structures: Modeling and Estimation Techniques," The Telecommunication Review pp. 59-71 (1999).

S. Fan, "Analysis of guided resonances in photonic crystal slabs", Physical Review B 65, 235112 (2002).

Marko Ledvij, "Curve Fitting Made Easy," The Industrial Physicist pp. 24-27, published by American Institute of Physics (Apr./May 2003).

Lan-Lan Lin, Zhi-Yuan Li, and Kai-Ming Ho, "Lattice symmetry applied in transfer-matrix methods for photonic crystals," Journal of Applied Physics 94(2), 811-21 (2003).

Z. Y. Li, L. L. Lin, "Photonic band structure solved by a plane-wave-based transfer-matrix method," Physical Review E 67, 046607 (2003).

"Peak Fitting Module Manual (version 7.5)," pp. 85, OriginLab Corporation, MA (2003). http://www.originlab.com/.

Ph. Lalanne, J. P. Hugonin, J. M. Gerard, "Electromagnetic study of the quality factor of pillar microcavities in the small diameter limit," Applied Physics Letters 84(23), 4726-8 (2004).

http://encyclopedia.laborlawtalk.com/Photonic_crystal.

Eric W. Weisstein. "Least Squares Fitting." From MathWorld—A Wolfram Web Resource. http://mathworld.wolfram.com/LeastSquaresFitting.html.

Eric W. Weisstein. "Interpolation." From MathWorld—A Wolfram Web Resource. http://mathworld.wolfram.com/Interpolation.html.

Eric W. Weisstein. "Nonlinear Least Squares Fitting." From MathWorld—A Wolfram Web Resource. http://mathworld.wolfram.com/NonlinearLeastSquaresFitting.html.

http://www.sensorsmag.com/express/.

http://cfa-www.havard.edu/HITRAN/.

http://www.swsciences.com/technology/sensors.html.

Anders Bjarklev, et al., "Comparison of strengths/weaknesses of existing numerical tools and outlining of modeling strategy", Report on PICCO deliverable D8 for WP4.

\* cited by examiner

| Gas Specimen | CO | CH₄ | C₂H₂ | HCN/HI | NH₃ |
|---|---|---|---|---|---|
| Absorption wavelength (nm) | 1570 | 1650 | 1520 | 1540 | 1500 |
| Absorption frequency (THz) | 191.1 | 181.8 | 197.4 | 194.8 | 200.0 |

*FIG. 6*

A side view of the optical path

| Extra Post's Location Label | Peak Frequency (THz) | Sensitivity Enhancement Factor |
|---|---|---|
| 0 | 181.84738367300201 | 27.32355223124698 |
| 1 | 161.54300172750601 | 38.7469544308952 |
| 2 | 161.86279632011599 | 38.14096566930428 |
| 3 | 162.88582450129999 | 44.95017823613852 |
| 4 | 162.28243486543499 | 44.62972979149267 |
| 5 | 164.88763603985899 | 72.88482814807649 |
| 6 | 168.60015549201401 | 94.02132450526581 |
| 7 | 172.95381400892899 | 71.74545053159626 |
| 8 | 177.570362549164 | 36.20910231468205 |
| 9 | 156.52150039935401 | 143.33749241184955 |
| 10 | 160.68980923571399 | 43.33332824716287 |
| 11 | 159.42340946048901 | 66.28823982554692 |
| 12 | 164.01931108716599 | 62.16315014817396 |
| 13 | 166.43296813197699 | 89.75831492091582 |
| 14 | 172.199440923743 | 77.97762025547833 |
| 15 | 176.76698798577601 | 41.83966511940792 |

| Extra Post's Location Label | Peak Frequency (THz) | Sensitivity Enhancement Factor |
|---|---|---|
| 0 | 181.83372769455099 | 183.12882521340464 |
| 1 | 161.63961434149999 | 361.7003134505772 |
| 2 | 161.96354823130801 | 350.20305378140563 |
| 3 | 162.944013064963 | 315.72689341040308 |
| 4 | 162.32162841142201 | 304.41534904701905 |
| 5 | 164.914420360061 | 240.86024478664382 |
| 6 | 168.648831226722 | 187.96096611688336 |
| 7 | 173.041797928574 | 182.8251147616534 |
| 8 | 177.65971788589599 | 169.09885612818417 |
| 9 | 156.66702013461 | 401.34289669752991 |
| 10 | 160.833589984865 | 353.59588493014559 |
| 11 | 159.57080209016499 | 327.64509635278324 |
| 12 | 164.04514755951601 | 253.39604766130495 |
| 13 | 166.45894663723999 | 198.52626304132505 |
| 14 | 172.27671923415301 | 182.59509467208613 |
| 15 | 176.86580800001801 | 166.65216854483751 |

| Gas Name | Absorption Wavelength (nm) | Corresponding Lattice Constant (nm) |
|---|---|---|
| CO | 1570 | 526.34249999999997 |
| CH4 | 1650 | 553.16250000000002 |
| C2H2 | 1520 | 509.57999999999998 |
| HCN/HI | 1540 | 516.28499999999997 |
| NH3 | 1500 | 502.875 |

GAS DETECTION AND PHOTONIC CRYSTAL DEVICES DESIGN USING PREDICTED SPECTRAL RESPONSES

BACKGROUND OF THE INVENTION

1. Field of the Invention

This invention generally relates to the field of gas detection and photonic crystal devices design, and specifically but not exclusively to gas detection and photonic crystal devices design that use numerical analysis to predict a spectral response of a photonic crystal.

2. Description of the Related Art

A photonic crystal is a periodic dielectric or metallo-dielectric (nano)structure that is designed to affect the propagation of electromagnetic waves in the same way as the periodic potential in a semiconductor crystal affects the electron motion, by defining allowed and forbidden photonic energy bands (See http://www.webster-dictionary.org/definition/Photonic%20crystalE; Yablonovitch, "Inhibited Spontaneous Emission in Solid State Physics and Electronics," Phys. Rev. Lett. 58, 2059-2062 (1987); S. John, "Strong Localization of Photons in Certain Disordered Dielectric Superlattices," Phys. Rev. Lett. 58, 2486-2489 (1987); and J. D. Joannopoulos, R. D. Meade, J. N. Winn, "Photonic Crystals," Princeton, N.J.: Princeton Univ. Press (1995)). The forbidden photonic energy band of a given photonic crystal is known as a "band gap", and represents the frequency range at which light cannot propagate unattenuated within a photonic crystal. By altering properties of the photonic crystal, a defect may be introduced in such a way as to allow a defect mode to exist within the band gap. Since the defect is surrounded by the periodic structures possessing a band gap, light can be localized at the defect region. Resonant frequencies can then be determined by analysis within the frequency range of the band gap.

In the design of devices which use photonic crystals, it may be helpful to obtain accurate and efficient predictions of the spectral response of a photonic crystal. For example, a predicted spectral response of a photonic crystal can be compared with known spectral response data corresponding to particular photonic crystal arrangements. In addition, such analysis may be useful for predicting changes in resonant mode behavior based on physical and/or environmental changes that affect a photonic crystal device.

Several techniques have been employed to determine the frequency range of a band gap for a photonic crystal having a defect therein. Such techniques include Plane Wave Expansion (PWE), the plane wave based Transfer Matrix Method (TMM), the Finite Element Method (FEM), Finite Difference Time Domain (FDTD), and Rigorous Coupled Wave Analysis (RCWA). These techniques can produce predicted estimates of a transmission spectrum which includes the frequency range of the band gap.

Although the above-mentioned techniques (including both frequency and time domain simulations) can determine the frequency range of the band gap, they typically do not provide sufficient information for analysis of the resonant frequencies occurring within the full range of the band gap. The resonant frequencies of a photonic crystal having a defect therein are typically represented as resonant peaks within the band gap range. However, the resolution of the transmission spectrum alone is usually too low for identifying and characterizing each of these resonant peaks.

To characterize each of the resonant peaks, it is desirable to determine the position (i.e. frequency) of each resonant peak within the range of the band gap, as well as the width (e.g. FWHM), and amplitude of each peak. It should be noted that resonant peaks with a high Q factor (quality factor) are often desired, with Q being proportional to the ratio between the peak frequency and the peak width.

As noted above, the transmission spectrum (e.g., generated by numerical methods such as PWE) alone typically does not have a high enough resolution to identify and characterize the resonant peaks. Thus, performance of additional numerical simulation is often necessary to obtain a sufficiently accurate prediction of a spectral response of a photonic crystal device.

One device that can benefit from the accurate and efficient prediction of a spectral response is a gas detector device using a photonic crystal cavity. In traditional gas detectors, like the one shown in FIG. 4, a laser light is output from a laser source 401, through a gas volume 402 across a distance L. The laser output travels through a gas specimen under detection, and the laser power decays exponentially due to absorption of the gas specimen. A photo detector 403 on the other side of the gas specimen detects the remaining optical power after the absorption. By monitoring the absorption optical power, the concentration of the gas specimen between the laser source 401 and the photo detector 403 can be determined.

In addition to determining the concentration of the gas specimen, the type of gas specimen can also be estimated. This is because most gases have unique absorption wavelengths, which correspond with unique atomic and molecular compositions. FIG. 5 illustrates a graph depicting the unique absorption wavelengths of different gases. There are more extensively tabulated absorption spectra and amplitudes available in several databases (e.g. HITRAN). Therefore, by choosing a specific wavelength of laser light, certain gas compositions can be detected without interference by other gas molecules. FIG. 6 illustrates a table showing a subset of 5 gases and their unique absorption wavelengths in the near infrared (NIR) wavelength range.

Although traditional gas sensors may be capable to detect presence of a gas, the sensors tend to be large and expensive, particularly for use in applications such as automobile and consumer gas sensors. The light path of such sensors are typically long, in order to increase the absorption properties of the gas sensor and to increase sensitivity. Additionally, ongoing adjustment may be required to maintain the performance of such gas, resulting in a higher overall cost for the sensor.

If a gas sensor was to be implemented using a photonic crystal cavity structure, gas can be introduced into the cavity. Since light is localized at the cavity (or defect region), light can be absorbed by the gas in the cavity more efficiently than the single path device shown in FIG. 4.

However, in order to measure the absorption rate, an accurate prediction of the spectral response of the photonic cavity is required. This prediction is useful for determining whether gas has been absorbed, and if so, what type of gas corresponds with the absorption rate. Since the prediction could be calculated numerous times, an efficient simulation is desired.

Another device which can benefit from the accurate and efficient prediction of spectral response data is a photonic crystal device for design and analysis of photonic crystals. From a design standpoint, such a device can be used to determine whether input data representing a particular photonic crystal structure meets desired design characteristics. Alternatively, from an analysis standpoint, such a device can be used for analyzing whether a photonic crystal contains a cavity, and if so, what the cavity structure looks like.

Analysis of spectral response data in the above-described devices is made more complex when dealing with 3D photonic crystal structures. Prediction of spectral response data with sufficient detail for a 3-D photonic crystal structure can require a large amount of time (e.g., several weeks) and computational resources (e.g., supercomputers with hundreds of CPUs) using conventional analysis approaches.

SUMMARY OF THE INVENTION

At least one exemplary embodiment provides for detecting presence of a gas having a specific absorption wavelength. Light passes through a photonic crystal cavity configured to sample a gas and receive light. The light has a wavelength that at least partially falls within the specific absorption wavelength of the gas. At least one parameter of a band gap spectrum is generated from at least a portion of the light passing through the photonic crystal cavity. In generating the at least one parameter, a numerical simulation is performed within a frequency range of the photonic crystal cavity to generate a set of spectral response data points, rational function interpolation is performed on the set of spectral response data points to generate a spectral response of the photonic crystal cavity, and at least one parameter representing the band gap spectrum is determined from the spectral response of the photonic crystal cavity. The at least one parameter of the generated band gap spectrum is compared with stored parameters of band gap spectrums, wherein a match of parameters indicates a presence and/or concentration of the gas.

At least one exemplary embodiment provides that the frequency range can represent a band gap of the photonic crystal embedded with a cavity. The numerical simulation performed within the frequency range of the photonic crystal band gap can use a finite difference time domain (FDTD) algorithm. The at least one parameter can comprise frequency, width, and amplitude information. The at least one parameter can be determined by using Lorentzian regression on the spectral response of the photonic crystal cavity.

At least one exemplary embodiment provides for a pillar positioned within the photonic crystal cavity, wherein movement of the pillar can adjust the spectral output of the photonic crystal cavity. The pillar can be positioned by an actuator. The pillar can be positioned on a substrate opposite a substrate on which the photonic cavity is mounted.

At least one exemplary embodiment provides for simultaneous detection of a plurality of gases comprising a plurality of gas detection devices, each with such a photonic crystal cavity arrangement, wherein each photonic crystal cavity is capable of detecting the presence of at least one of the plurality of gases.

At least one exemplary embodiment provides that the gas can be introduced into the photonic crystal cavity via gas inlet channels. Mirrors can be provided for reflecting the light from an emitter to the photonic crystal cavity, and for reflecting light passing through the photonic crystal cavity to a detector. The photonic crystal cavity can be in a 3D photonic crystal.

At least one exemplary embodiment provides for determining whether data representative of a photonic crystal meets a predetermined design standard for photonic crystal device design. Data representative of the photonic crystal device is received, and a frequency solution of the photonic crystal is generated based on the data representative of the photonic crystal. A band gap spectrum is generated from the frequency solution of the photonic crystal. In generating the band gap spectrum, a numerical simulation is performed within the frequency solution of the photonic crystal to generate a set of spectral response data points, rational function interpolation is performed on the set of spectral response data points to generate a spectral response of the photonic crystal, and parameter information representing the band gap spectrum is determined from the spectral response of the photonic crystal cavity. A determination is made as to whether the data representative of the photonic crystal device meets the predetermined design standard based on the generated band gap spectrum.

At least one exemplary embodiment provides that the frequency range can represent a band gap of the photonic crystal. The parameter information can comprise frequency, width and amplitude information. The parameter information can be determined by performing Lorentzian regression on the spectral response of the photonic crystal cavity. The data representative of a photonic crystal can represent a 3D photonic crystal. The frequency solution can be determined using Maxwell's equation based on the data representative of the photonic crystal. If it is determined that the data representative of the photonic crystal does not meet the predetermined design standard based on the generated band gap spectrum, the data representative of the photonic crystal can be modified and the steps of receiving, generating a frequency solution, generating a band gap spectrum, and determining can be repeated with the modified data.

At least one exemplary embodiment provides for characterizing a photonic crystal. Light is emitted such that the light is incident upon and passes through the photonic crystal, and at least a portion of the light that passes through the photonic crystal is detected. A band gap spectrum is generated from the detected portion of the light. In generating the band gap spectrum, a numerical simulation is performed within a frequency range of the photonic crystal to generate a set of spectral response data points, rational function interpolation is performed on the set of spectral response data points to generate a spectral response of the photonic crystal, and parameter information representing the band gap spectrum is determined from the spectral response of the photonic crystal. The generated band gap spectrum is compared with stored band spectrums for characterizing the photonic crystal.

At least one exemplary embodiment provides that the frequency range can represent a band gap of the photonic crystal. The parameter information can comprise frequency, width and amplitude information. The parameter information can be determined by performing Lorentzian regression on the spectral response of the photonic crystal cavity. The data representative of a photonic crystal can represent a 3D photonic crystal. The frequency solution can be determined using Maxwell's equation based on the data representative of the photonic crystal.

At least one exemplary embodiment provides for a tunable device comprising at least one photonic crystal, where the at least one photonic crystal has at least one of an adjustable refractive index, an adjustable lattice constant, an adjustable pillar within a cavity in the at least one photonic crystal, and an adjustable hole within a cavity in the at least one photonic crystal. The tunable device further comprises at least one tuning mechanism, where the at least one tuning mechanism is configured to tune a resonance frequency of the at least one photonic crystal by changing at least one of the refractive index, the lattice constant, and the pillar position within the cavity.

At least one exemplary embodiment provides that the at least one photonic crystal has an adjustable refractive index, and that the at least one tuning mechanism tunes a resonant frequency of the at least one photonic crystal by changing the refractive index of the photonic crystal using the Kerr effect. The at least one photonic crystal can have an adjustable refractive index, and the at least one tuning mechanism can tune a resonant frequency of the at least one photonic crystal by changing the refractive index of the photonic crystal using the Pockels effect.

At least one exemplary embodiment provides that the at least one photonic crystal can have a cavity with an adjustable pillar within the cavity. The at least one tuning mechanism can tune a resonant frequency of the at least one photonic crystal by changing the pillar position in the cavity. The at least one photonic crystal can have a cavity with an adjustable hole within the cavity. The at least one tuning mechanism tunes a resonant frequency of the at least one photonic crystal by changing the hole position in the cavity. The at least one photonic crystal can have an adjustable lattice constant, and the at least one tuning mechanism can tune a resonant frequency of the at least one photonic crystal by changing the lattice constant.

At least one exemplary embodiment provides that the tunable device can have a first photonic crystal having a first cavity and a first adjustable element in the first cavity, where the first adjustable element is one of a first adjustable pillar and a first adjustable hole, a second photonic crystal having a second cavity and a second adjustable element in the second cavity, where the second adjustable element is one of a second adjustable pillar and a second adjustable hole, and the tunable device can have a first tuning mechanism and a second tuning mechanism. The first tuning mechanism and the second tuning mechanism can be operated simultaneously. The first tuning mechanism can set a first lattice constant of the first photonic crystal, where the first lattice constant tunes the first photonic crystal to a first resonant frequency, and where the second tuning mechanism sets a second lattice constant of the second photonic crystal, where the first lattice constant tunes the first photonic crystal to a first resonant frequency. The first adjustable element and the second adjustable element can be adjusted to about the same relative position within their respective cavities.

At least one exemplary embodiment provides that the tunable device can have a first photonic crystal and a second photonic crystal, where the first photonic crystal has at least one of an adjustable refractive index, an adjustable lattice constant, an adjustable pillar within a cavity in the at least one photonic crystal, and an adjustable hole within a cavity in the at least one photonic crystal. The tunable device can be part of at least one of a tunable laser, a gas sensor, and a photo diode.

At least one exemplary embodiment provides for constructing a tunable device. A photonic crystal is constructed by depositing a first layer of material, where the first layer includes a multiple of strips of a first material spaced a first distant from each other, depositing a second layer of material on the first layer, where the second layer includes a multiple of strips of a second material spaced a second distant from each other, where the strips of the second material are arranged to be non parallel to the strips of the first material, and depositing a third layer of material on the second layer, where the third layer includes a multiple of strips of a third material spaced a third distant from each other, where the strips of the third material are arranged to be substantially parallel to the strips of the first material, and where the strips of the third material are offset the first offset distance with respect to the strips of the first material. The photonic crystal is further constructed by depositing a fourth layer of material on the third layer, where the third layer includes a multiple of strips of a fourth material spaced a fourth distant from each other, where the strips of the fourth material are arranged to be substantially parallel to the strips of the second material, and where the strips of the fourth material are offset the second offset distance with respect to the strips of the second material, and depositing additional layers by repeating the laying of the, first, second, third, and fourth layers on previous layers, until a series of layers of a chosen thickness is accumulated. The first and second offset distance are chosen so that the photonic crystal is tuned to at least a first resonance frequency.

At least one exemplary embodiment provides that a first electrode can be deposited on a first side of the photonic crystal, a second electrode can be deposited on a second side of the photonic crystal, where the second side is not the first side, and a voltage difference can be applied between the first and second electrodes, where the voltage difference changes the refractive index of the photonic crystal tuning the photonic crystal to a second resonance frequency.

At least one exemplary embodiment provides that at least one cavity can be placed in at least one of the first, second, third, and fourth layers by modifying the length of at least a few of the respective strips. An adjustable pillar can be deposited in the at least one cavity, and the pillar can be moved, where moving the pillar adjusts the tuning of the photonic crystal to a third resonance frequency. A hole can be adjusted in the boundaries of the at least one cavity, where adjusting the hole adjusts the tuning of the photonic crystal to a third resonance frequency.

At least one exemplary embodiment provides for crystal fabrication. Tuning curves are developed, where the tuning curves are developed from parameters of a photonic crystal design, and where the parameters are derived from simulation of the photonic crystal design. The effect of fabrication tolerances on the tuning curves is determined. A target tuning property of the photonic crystal design is selected. A prototype photonic crystal is developed, where new parameters are used to develop the prototype photonic crystal, and where the new parameters are chosen by optimizing the interaction between the effect of fabrication tolerances and the target tuning property.

At least one exemplary embodiment provides that the prototype photonic crystal can be tested to determine if the actual tuning property is within a predetermined variation from the target tuning property.

At least one exemplary embodiment provides that the new parameters can be chosen by selecting the new parameter values to be at least one parameter value associated with difficult to control fabrication related parameters which fall within the regions where the tuning curves are relatively flat, selecting the new parameter values to be at least one parameter value associated with controllable fabrication related parameters which fall within the region where the tuning curves are relatively steep, selecting the new parameter values to be at least one parameter value that fall within the region where the tuning curves are relatively steep while providing a tuning frequency within a predetermined variation value of a target tuning frequency, and selecting the new parameter values to be at least one parameter value that fall within the region where the tuning curves are relatively flat while providing a tuning frequency with a predetermined tuning frequency error.

Further areas of applicability of exemplary embodiments will become apparent from the detailed description provided hereinafter. It should be understood that the detailed description and specific examples, while indicating exemplary embodiments, are intended for purposes of illustration only and are not intended to limit the scope of the exemplary embodiments.

BRIEF DESCRIPTION OF THE DRAWINGS

FIG. 6 illustrates a table depicting a subset of 5 gases and their unique absorption wavelengths in the near infrared (NIR) wavelength range.

FIG. 35A illustrates an example of a 3-D photonic crystal, while

DETAILED DESCRIPTION OF THE INVENTION

The following description of exemplary embodiments is merely illustrative in nature and is in no way intended to limit the invention, its application, or uses.

Processes, techniques, apparatuses and materials as known by one of ordinary skill in the relevant art may not be discussed in detail but are intended to be part of the enabling description where appropriate.

Figure 1:
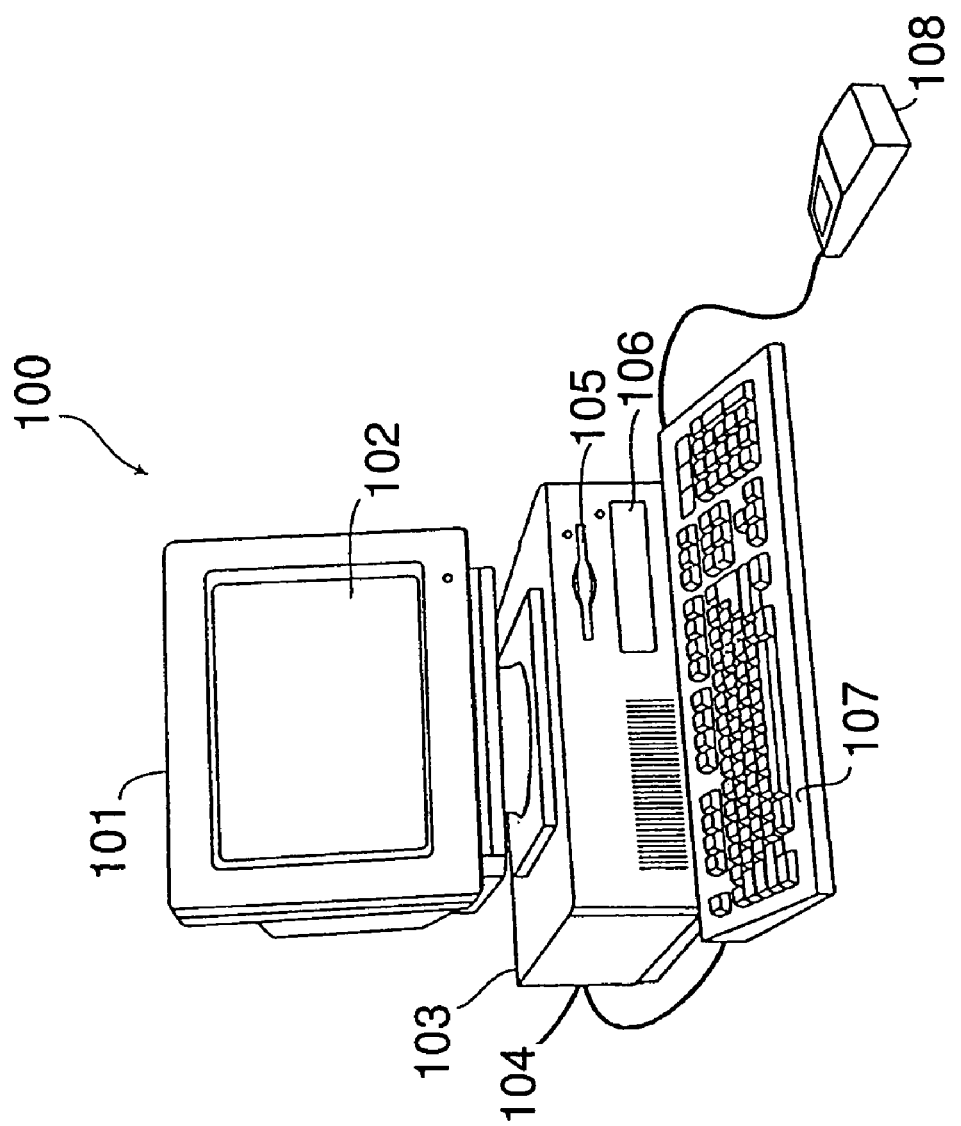
FIG. 1 illustrates one example of a computer system in which at least one exemplary embodiment may be implemented.

FIG. 1 illustrates an example of a computation system 100 (e.g., computer system) in which at least one exemplary embodiment may be implemented. The computation system 100 can comprise: a host processor 103, which comprises a personal computer (hereinafter "PC"); a color monitor 101 including display screen 102; a keyboard 107 for entering text data and user commands; and a pointing device 108 (e.g., a mouse), for manipulating objects displayed on display screen 102.

Computation system 100 can include a computer readable memory medium (e.g. a computer fixed disk 106 and/or floppy disk drive 105). Floppy disk drive 105 provides a computer readable storage medium whereby computation system 100 can access information on a removable memory media, (e.g. image color data, computer-executable process steps, application programs, equivalents and other computer information) stored on removable memory media. A similar CD-ROM interface (not shown) may be provided for the computation system 100 through which the computation system 100 can access information stored on the removable CD-ROM media. In addition, in at least one exemplary embodiment, network access 104 allows the computation system 100 to acquire and interact with information and application programs from other sources, such as a local area network or the Internet.

Although discussion herein has provided a PC as an example of a host processor 103, many other computation systems containing processors can be used in at least one exemplary embodiment (e.g., notebook computers, hand-held computation systems, equivalents and other processor containing systems as known by one of ordinary skill in the relevant art).

At least one exemplary embodiment may be incorporated in an output device driver for execution in a computing device, embedded in the firmware of an output device, or provided in a stand-alone simulation application for use on a general purpose computer. It can be appreciated that the exemplary embodiments are not limited to the examples provided and may be used in other environments.

Figure 2:
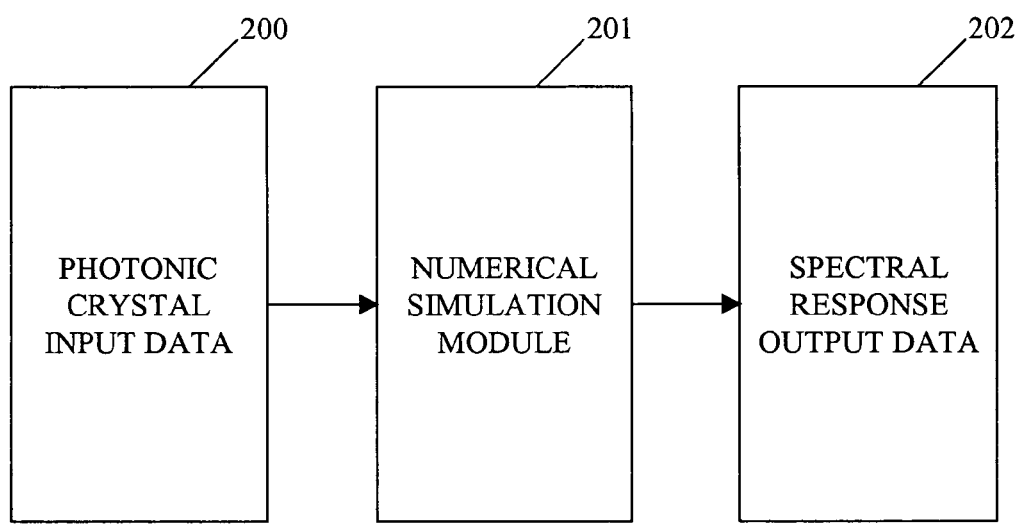
FIG. 2 illustrates the relationship between portions of at least one exemplary embodiment.

FIG. 2 illustrates the informational flow associated with a numerical simulation module in accordance with at least one exemplary embodiment. The numerical simulation performed by at least one exemplary embodiment is implemented in numerical simulation module 201. Numerical simulation module 201 is applied to photonic crystal input data 200 in order to generate spectral response output data 202.

The photonic crystal input data 200 may include periodicity information for a photonic crystal cavity and particular properties of a defect. The numerical simulation module 201 inspects the photonic crystal input data 200 and determines predicted spectral response output data 202. The spectral response output data 202 may include parameter information such as frequency, line width and amplitude of the resonant modes as well as other spectral information, which can be provided to a gas detector device or photonic crystal design device as described later.

Numerical simulation module 201 is capable of performing different types of numerical simulations on the photonic crystal input data 200. For example, numerical simulation module 201 may calculate a band gap range, calculate N frequency points for a photonic crystal using an algorithm such as TMM, perform rational function interpolation on the N frequency points to generate one or more resonant peaks, and perform a simulation such as Lorentzian regression near each of the resonant peaks.

Figure 3:
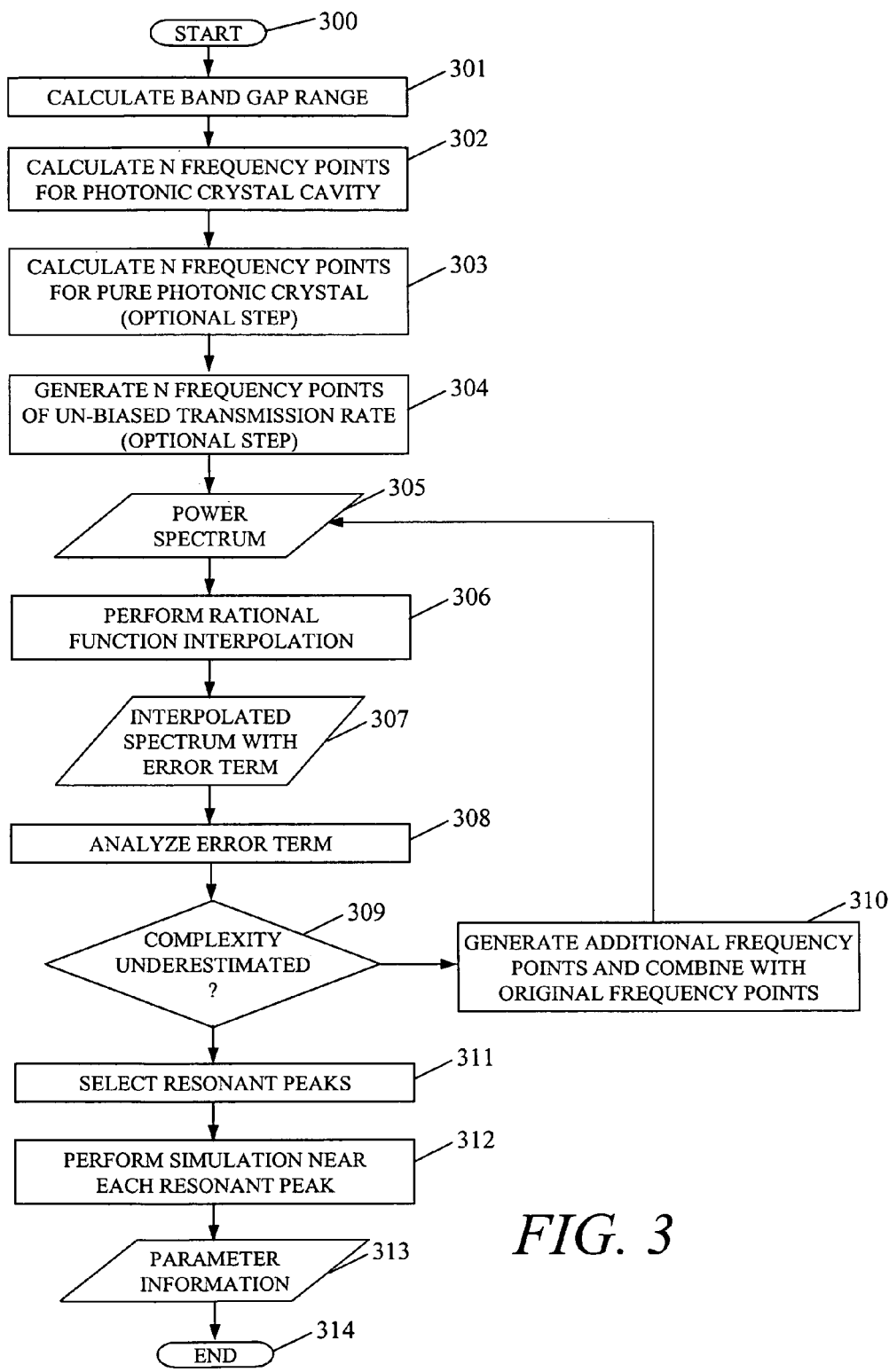
FIG. 3 illustrates a flowchart depicting at least one exemplary embodiment for performing numerical analysis to predict a spectral response of a resonant optical structure.

FIG. 3 illustrates a flowchart depicting at least one exemplary embodiment for performing numerical analysis to predict a spectral response of a resonant optical structure. This numerical simulation can be used to obtain improved predictions of the spectral response of a photonic crystal, and can be incorporated into the design of a device using a photonic crystal. Such devices include, for example, a gas detector using a photonic crystal cavity, and a photonic crystal device for design and analysis of photonic crystals.

Following start bubble 300, the full band gap range of the underlying photonic crystal is calculated (block 301). The full band gap range of a particular photonic crystal can by calculated by many numerical methods, such as PWE, FDTD, TMM and FEM. In addition, the result can be re-used for different optical cavity problems, as long as the underlying photonic crystal remains unchanged.

Although in the particular example described, the full band gap range is calculated, other exemplary embodiments can compare the band gap range calculated up to a point with a maximum band gap value. If during calculation the present band gap range exceeds a chosen minimum band gap value, the computation is stopped and a new candidate photonic crystal can be chosen for analysis.

After the range of the full band gap has been determined, N frequency points are calculated across the full band gap range of the photonic crystal cavity (block 302). These N frequency points can be generated by performing TMM within the range of the calculated band gap.

The initial number of frequency points, N, is based on an equation of N=4 m+1, where "m" is an estimated maximum number of resonant states existing in the optical cavity system. Normally, for a single unit cell defect cavity in photonic crystal, no more than 5 significant localized resonant modes are expected.

The origin of the N=4 m+1 equation for determining how many frequency points should be used for block 302 will now be described. First, it should be noted that the resonant features through a photonic crystal optical cavity were discovered in exemplary embodiments represent Lorentzians, which is a consequence of the time dependence characteristic of Maxwell's equations. As such, the most general form of the superposition of multiple Lorentzians is as follows:

$$f(x) = \sum_{i=1}^{m} \left( a_i + \frac{b_i}{(x-c_i)^2 + d_i^2} \right) \quad \text{(Equation 1)}$$

Here, $\{a_i, b_i, c_i, d_i\}$ are a total of 4 m independent parameters specifying any superposition of up to m Lorentzians. More specifically, $a_i$ represents the shift of a curve, $b_i$ represents the peak value, $c_i$ represents peak frequency and $d_i$ represents half of the full-width maximum of a peak. Equation (1) was then transformed into the following:

$$f(x) = \sum_{i=1}^{m} \frac{a_i x^2 - 2a_i c_i x + (a_i c_i^2 + a_i d_i^2 + b_i)}{x^2 - 2c_i x + d_i^2} = \quad \text{(Equation 2)}$$

$$\sum_{i=1}^{m} \frac{P_{3,i} x^2 + P_{4,i} x + P_{5,i}}{x^2 + P_{1,i} x + P_{2,i}}$$

In equation (2), the combination of the parameters from 4 m independent parameters (i.e. $\{a_i, b_i, c_i, d_i\}$) was changed to 5m dependent parameters (i.e. $\{P_{1,i}, P_{2,i}, P_{3,i}, P_{4,i}, P_{5,i}\}$). The summation of equation (2) can be evaluated to generate the following rational function form:

$$f(x) = \frac{\sum_{i=0}^{2m} p_i x^i}{x^{2m} + \sum_{i=0}^{2m-1} q_i x^i} \quad \text{(Equation 3)}$$

Looking at equation (3), it can be seen that there are a total of (4 m+1) parameters, (i.e. $\{p_i, q_i\}$). In addition, there is only one redundant dependent parameter compared to the 4 m of $\{a_i, b_i, c_i, d_i\}$ of equation (1). This small redundancy allows for the use of interpolation/extrapolation algorithms for diagonal rational functions, where the word "diagonal" refers to the degrees of numerator and denominator being equal. Moreover, it is later shown that this rational function form can also adapt some asymmetric features in spectra which arise from non-cavity modes.

An example of a robust and efficient interpolation/extrapolation algorithm, that can be used in exemplary embodiments, is the Bulirsch-Stoer algorithm of the Neville type. This algorithm is a good fit for the diagonal rational function form. In addition, the Bulirsch-Stoer algorithm generates an estimated error term, which provides valuable information as discussed later.

Other algorithms can be used, for example the Vandermode matrix type algorithm, although this algorithm typically has a very low numerical stability for more than approximately 16 points, due to its intrinsic non-stability, and the discussion herein is not intended to limit exemplary embodiments to any particular algorithm.

Before further discussion of rational function interpolation, reference is made to blocks 303 and 304 of FIG. 3. It should be noted that these steps (303, 304) are described by way of example only, but are not necessary for all exemplary embodiments. In particular, these steps can be used to determine an un-biased transmission rate, based on the difference between the photonic crystal cavity and a pure photonic crystal (i.e. no cavity). After performing TMM on the frequency points of the photonic crystal cavity (block 302), TMM can be performed again with the same points, but on a pure photonic crystal having no cavity (block 303). The difference between the frequency points generated by the photonic crystal cavity and the pure photonic crystal represents the unbiased transmission rate. Whether or not blocks 303 and 304 are performed, the output at block 305 is a power spectrum at the N frequency points, which is in turn used for input for rational functional interpolation.

The power spectrum of the N frequency points is used as the input for rational function interpolation (block 306). Performance of the rational function interpolation (e.g. the Bulirsch-Stoer algorithm) can generate the prediction of the full power spectrum with arbitrary high resolution across the full band gap of the frequency range. In addition, it only requires a relatively small amount of computation time (e.g. several seconds total). As noted above, in addition to generating an interpolated spectrum with arbitrary high resolution, some algorithms generate a corresponding error term (output 307).

The reason for performing interpolation at this stage, rather than performing another analysis such as regression, is because of the manner in which interpolation behaves. Interpolation is a computation of points or values between ones that are known or tabulated using the surrounding points or values. An interpolated/extrapolated curve has to strictly pass through all input data points. As such, a solution is facilitated when interpolation is used when the number of peaks is unknown.

Regression, on the other hand, is a mathematical procedure for finding the best-fitting curve to a given set of points by minimizing the sum of the squares of the offsets ("the residuals") of the points from the curve. Regression does not need to pass through each and every data point, but will instead minimize an error measurement. Regression tends to be less susceptible to noise when compared with interpolation. However, since the number of resonant peaks is unknown, and since regression does not pass through every data point, regression may fail to detect all of the resonant peaks. As will be described later in at least one exemplary embodiment, regression is more suitable after rational function interpolation is performed, since it provides for parameter information and also may detect multiple resonant peaks which occur within a common envelope curve.

Analysis of the estimated error term should then be performed to determine if the complexity of the photonic crystal cavity was underestimated, i.e. whether there might be more resonant peaks than estimated (block 308 and decision diamond 309). More specifically, a comparison can be made between the interpolated power spectrum and the estimated error term, to see whether the error term is constantly lower than the interpolated power spectrum itself.

If the estimated error term is constantly lower than the interpolated power spectrum, this indicates a likelihood that the initial estimate for the number of resonant peaks (i.e., "m") was either correct or an overestimate. In either case, the resulting interpolated power spectrum would be accurate. On the other hand, if the error term exceeds the interpolated power spectrum, this indicates an underestimation of complexity, in which the interpolated power spectrum can be updated with additional frequency points.

When the complexity of the photonic crystal cavity is likely underestimated, an additional $N_1$ frequency points can be calculated by TMM, and these $N_1$ points are combined with the original set of TMM frequency points (block 310).

For transmission spectra through photonic crystal cavities, underestimated cases can generally be divided into two categories. The first category includes extra resonant peaks with relatively high amplitudes and low quality factors existing outside the frequency range of the full photonic crystal bandgap. The second category includes extra resonant peaks with relatively low amplitude and high quality factor existing inside the frequency range of the full photonic crystal bandgap.

Regarding the second category of underestimation, in which extra resonant peaks with relatively low amplitude and high quality factor exist inside the frequency range of the photonic crystal bandgap, the error term typically provides an indication as to how many resonant peaks were not accounted for. This information is typically apparent by comparing the spectral response with the error term, and determining at what positions the error term exceeds the spectral response. Such positions typically correspond to missed resonant peaks.

After analysis of the error term, rational function interpolation is once again performed on the updated transmission spectrum, which includes the original N points and the additional $N_1$ points (block 306). The error term will typically be below the spectral response at this point, so that no further TMM calculations need to be calculated. Any number of iterations of the process described lies within exemplary embodiments.

Once it is determined that the complexity of the photonic crystal cavity has not been underestimated in decision diamond 309 (i.e. the estimated number of resonant modes is greater than or equal to the number of resonant peaks), further numerical simulation may be performed at the vicinity of each of the resonant peaks. For each of the resonant peaks in the spectral response, the peak is selected (block 311), and numerical simulation is performed near that peak (block 312). In at least one exemplary embodiment no further numerical simulation is performed.

In other exemplary embodiments, the reason for performing additional numerical simulations is twofold. First, it may be difficult to determine the desired accuracy level of information for each of the peaks after rational function interpolation has been performed. The second reason for performing the additional numerical simulation is to detect when multiple resonant peaks overlap in a region that appears only to have one peak.

Regarding the first reason, it should be noted that although algorithms (e.g., the Bulirsch-Stoer algorithm) provide a spectral response and estimated error term information, they do not provide for parameter information, such as frequency, width and amplitude of the resonant peaks. Such parameter information can be obtained by performing additional numerical simulation on each of the resonant peaks.

As noted above, regression is a mathematical procedure for finding the best-fitting curve to a given set of points by minimizing the sum of the squares of the offsets ("the residuals") of the points from the curve. In practice, non-linear regressions are implemented quite differently from linear regression. Unlike linear regression that can be reduced to a set of deterministic linear equations, nonlinear regression is an iterative numerical searching process. Like every numerical searching process, nonlinear regression is not a deterministic process, and its answers may depend on the initial value selected for each parameter (first factor), and the iteration algorithm chosen (second factor). The above two factors exhibit stronger influence, when more parameters are involved in the regression, for example when multiple Lorentzian peaks are presented in a curve. Although, in the examples of exemplary embodiments discussed, Lorentzian regression is used, other algorithms may be used.

Thus, in the example of at least one exemplary embodiment discussed using the Bulirsch-Stoer algorithm, since the Bulirsch-Stoer algorithm does not provide parameter information for each of the resonant peaks, additional numerical simulation can be performed to provide the desired parameter values. However, if a rational function interpolation algorithm other than Bulirsch-Stoer is used, and such rational function interpolation algorithm does provide parameter information, the performance of additional numerical simulation would not be necessary. However, such numerical simulation would still be useful to detect if multiple peaks overlap at the same curve.

The parameter information is represented in output block 313, and can include frequency, line width and amplitude information for each of the resonant peaks. This is followed by end bubble 314.

Figure 4:
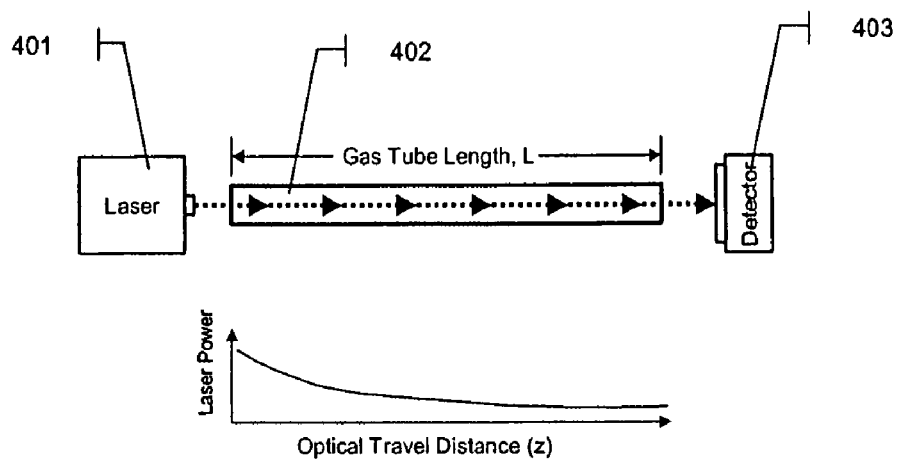
FIG. 4 illustrates a traditional implementation of a gas sensor based on laser optics.

The above-described numerical simulation as described with reference to FIG. 3 can be used in a gas detector device which uses a photonic crystal cavity to contain a gas sample. As noted above with reference to FIGS. 4 to 6, most gases have unique absorption wavelengths which correspond with unique atomic and molecular compositions. Accordingly, by monitoring the absorption optical power of a gas, the concentration of a gas specimen can be determined, and the type of gas specimen can also be predicted.

Figure 7:
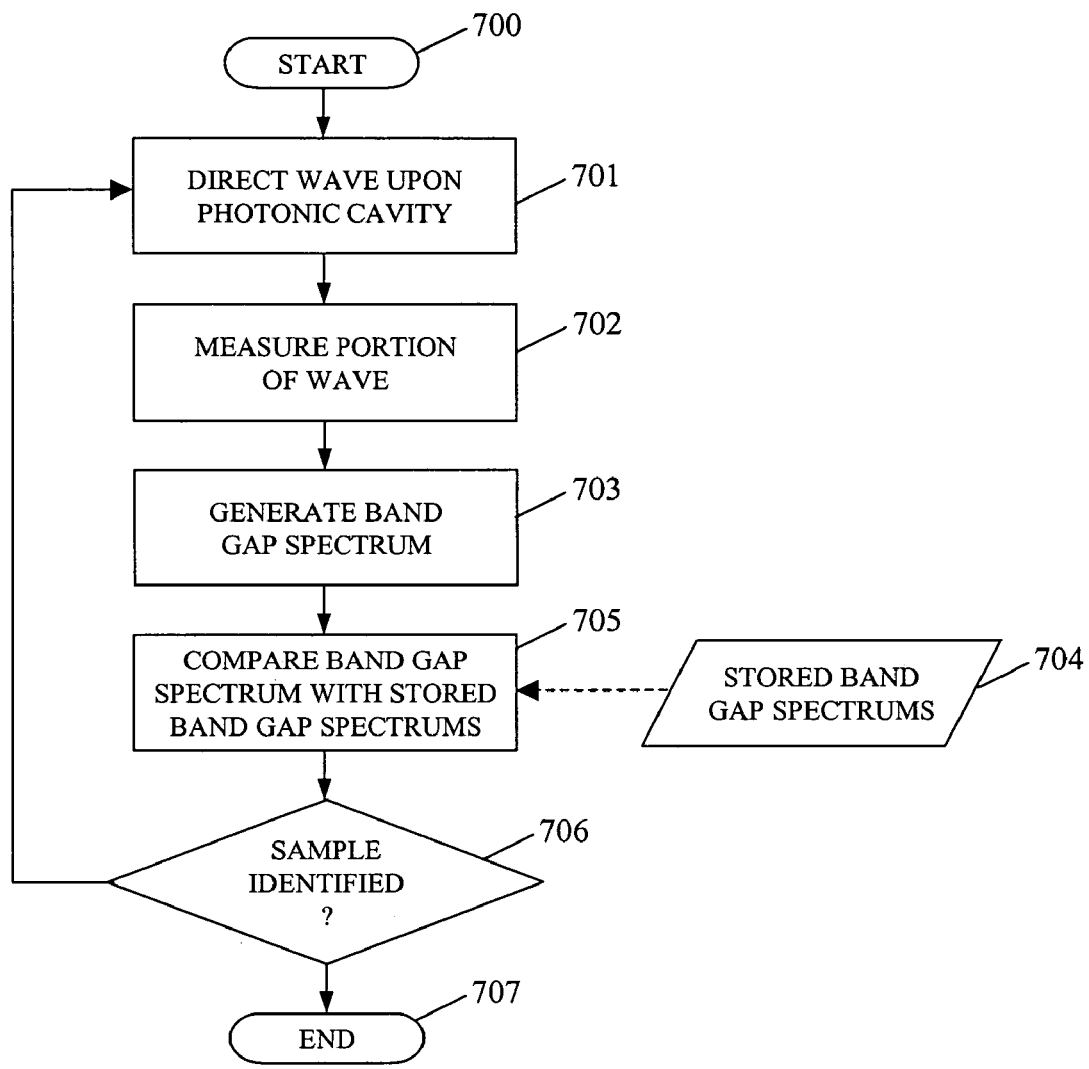
FIG. 7 illustrates a flowchart depicting at least one exemplary embodiment for detecting a gas sample using a photonic crystal cavity.

FIG. 7 illustrates a flowchart depicting at least one exemplary embodiment for detecting the presence of a gas sample using a photonic crystal cavity. Following start bubble 700, a multi-wavelength electromagnetic wave is directed to a photonic crystal cavity containing a gas sample to be analyzed (block 701). The multi-wavelength electromagnetic wave can be centered about a primary wavelength having a small bandwidth, or the wave can be a monochromatic electromagnetic wave. In addition, at least a portion of the wavelength of the electromagnetic wave should fall within the absorption wavelength of the gas sample to be tested. At least a portion of the electromagnetic wave passing through the cavity is then measured (block 702).

A band gap spectrum is then generated from the measured electromagnetic waves (block 703). This band gap spectrum can be generated, for example, by performing the above-described numerical simulation, upon the photonic crystal cavity included in the gas detector device.

Next, the generated band gap spectrum is compared with stored band gap spectrums, in order to identify the presence of a gas sample (block 704). The stored band gas spectrums may include, for example, a band gap spectrum of the photonic crystal cavity in which no gas is introduced.

A decision is then made as to whether the gas sample has been identified based on the comparison (decision diamond 706). In particular, if absorption of the electromagnetic waves occurred, the generated band gap spectrum would likely not match the band gap spectrum of the photonic crystal cavity in which no gas was introduced. This would suggest that a gas sample was detected in the photonic crystal cavity. If a gas sample is identified, the process ends (end bubble 707). Otherwise, the process repeats by returning to block 701, until presence of the sample gas is identified, or a set criteria is reached (e.g. a 100-second maximum sample time).

As noted above, the use of a photonic crystal cavity to contain a photon (i.e. light) provides advantages over traditional gas sensors. The arrangement using a photonic crystal cavity raises the chance of the photon being absorbed by the gas specimen inside the cavity.

Regarding the absorption of the photon, the Beer-Lambert law is an equation which relates the absorption of light in a gas as a function of the frequency and path length. The Beer-Lambert law can be written in the time domain as:

$$A = \alpha(\lambda) \times \tau_{ph} \times c_0 \times c \qquad \text{(Equation 4)}$$

In Equation 4, A represents a measured absorption, $\alpha(\lambda)$ represents a wavelength-dependent absorption coefficient, $\tau_{ph}$ represents the photon lifetime inside the cavity, $c_0$ represents the speed of the light, and c represents an analytic concentration. In a traditional gas sensor, such as the one depicted in FIG. 4, the photon lifetime for a single-pass can be understood as $\tau_{ph} = L/c_0$, which is the time needed for a photon to fly through the length L of the gas specimen tube. However, if the gas specimen tube is changed to an optical cavity, which can trap the photon inside it for a time span longer than $L/c_0$, then the absorption of the laser light is improved.

One consideration in the design of a gas detector device using a photonic crystal cavity is the length of analysis time required for deriving an accurate band gap structure. Conventional approaches to predicting accurate band gap structures are seen require an unreasonable amount of time. Therefore, such approaches are seen to render design and use of a gas detector with a photonic crystal cavity impractical. On the other hand, the above-described numerical simulation is seen to predict an accurate band gap structure within a reasonable time, and is thus seen to enable design and use of such a gas detector device. The following few paragraphs compare conventional analysis times with times afforded by use of the above-described numerical simulation.

If a photonic device with Q~400 is chosen (where Q is the ratio of the peak frequency and the peak width), an FWHM (or width) of ~0.5 THz should be expected. This requires a resolution of at least 0.1 THz (i.e. 1/5 of the FWHM) to see decent detail for the Lorentzian peak.

To obtain this spectral resolution, starting from a time domain simulation such as Finite-Difference Time-Domain (FDTD), a Discrete Fourier Transformation (DFT) should be performed, using the time domain signal as its input.

A spectral resolution obtained through DFT corresponds with the equation $\Delta f = 1/T$, where $\Delta f$ is the frequency resolution obtained after DFT, and the T is the total length of the time domain as the input signal for DFT. In other words, the spectral resolution obtained through DFT is proportional to the inverse of the length of the signal in the time domain. As such, a 10 ps-long-time-sequence generated from the FDTD routine would be needed.

The execution of the FDTD program for a 1 ps-long-time-sequence requires approximately 461 seconds (i.e. 7.7 minutes) per run. If the time sequence is increased to 10 ps, the execution time would approximate 77 minutes (i.e. 1.3 hours) per run.

As will described below, in order to make realistic device designs, and to account for fine tuning and error analysis, hundreds (or perhaps thousands) of iterations of a simulation run to predict an accurate spectral response may be required. Time consumption at a scale of 1.3 hours per run would render design of such a gas detector impractical. Furthermore, when a higher Q value is needed for higher enhancement and sensitivity, the time consumption would render design and use of such a gas detector device even more impractical.

The numerical simulation as described with reference to FIG. 3 enables accurate and detailed analysis of band gap spectrums in a rapid amount of time. For example, what conventionally equates to hours and days of computation time using conventional techniques can take seconds and minutes using the above-described numerical simulation.

Thus, using the above-described numerical simulation, concept design, optimization of such devices to realize a final specification, optimization of processes considering process margin and yield, inspection methods to keep high quality, and trouble analysis can be realized. In addition, the speed and accuracy of the numerical simulation of the exemplary embodiment provides for the possibility of trying and establishing new manufacturing techniques.

Turning to the manufacture of a gas device using a photonic crystal cavity, considerations for designing such a device include: (a) a simple structure for reducing cost maintaining high yield; (b) integration capability to reduce adjustment; ©) multi-gas detection capability to improve application of the sensor; (d) size approximately as small as a Si chip to improve application; (e) high sensitivity to improve application; (f) capability to estimate process margin for manufacturing process; (g) freedom to expand the process margin to maintain high yield; and (h) establishment of a methodology to correlate between actual experimental results and theory for trouble shooting purposes.

Figure 8A:
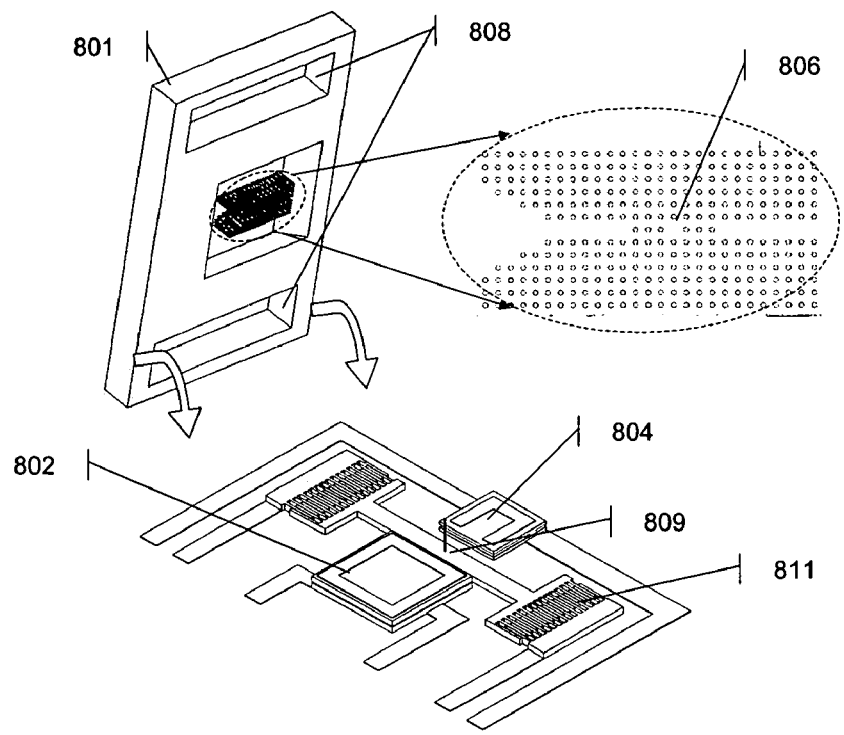
FIGS. 8A to 8C illustrate a first exemplary embodiment of a gas detector using a photonic crystal cavity.
Figure 8B:
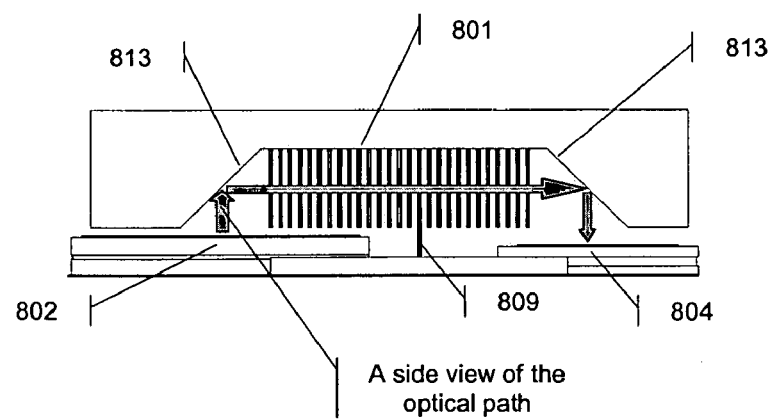
Figure 8C:
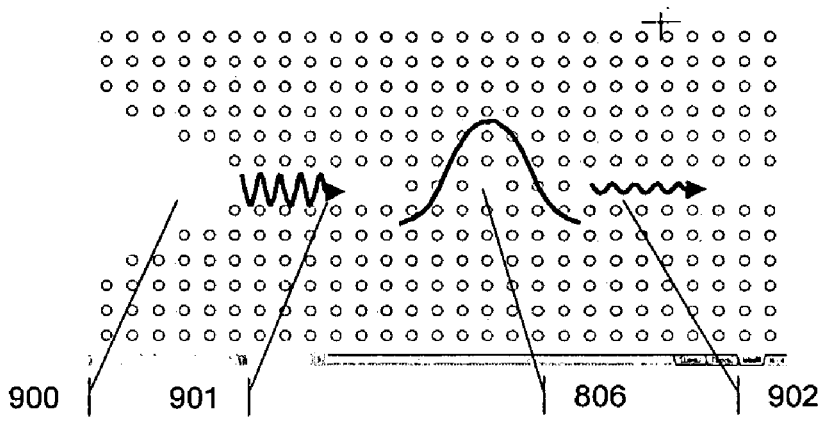

Thus, a gas sensor in accordance with these design considerations and consistent with exemplary embodiments of a gas detector having a photonic crystal cavity can include: a waveguide for light direction, a light source producing the light to be directed, a light detector for detecting light leaving the photonic cavity, a method/device to introduce gas into the cavity, and finally a peripheral driver and circuit, as illustrated in FIGS. 8A to 8C.

FIGS. 8A to 8C illustrate a first exemplary embodiment of a gas detector using a photonic crystal cavity. The gas detector includes a top-substrate 801, with a photonic crystal having a cavity 806, 45-degree wedges 813 which function as reflection mirrors, and micro-channels for gas flow 808. The gas detector also includes a vertical emitting laser diode or light emitting diode 802, whose wavelength range covers the targeted gas specimens. A photo diode 804 detects the transmitted optical signal after gas absorption.

A high quality factor optical cavity 806 is formed by photonic crystals. The gas detector also can include electrostatic actuators 811 (e.g., comb-drives). A single pillar 809 can be located inside optical cavity 806, and the position of the pillar 809 can be adjusted using the actuators 811. The position adjustment of the pillar 809 via wafer-bonding can act as a dynamic tuning mechanism of the optical cavity 806, as will be discussed later.

Figure 9:
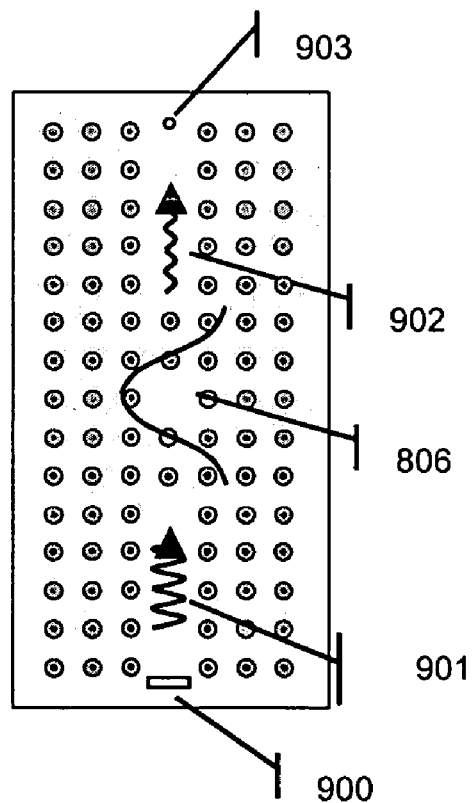
FIG. 9 illustrates an exemplary embodiment of the optical cavity structure of FIGS. 8A to 8C.

FIG. 9 illustrates an exemplary embodiment of the optical cavity structure of FIGS. 8A to 8C. An optical pulse is emitted from light emitting diode 802, vertically. The optical pulse can then reflected (e.g., by 45-degree wedge 813) in the horizontal direction to enter funnel 900, which is an optional funnel for increasing the coupling efficiency into an incident waveguide 901. An optical signal component (or photon) with the selected frequency (i.e. the resonant frequency for optical cavity 806) is first trapped in a high cavity mode inside optical cavity 806 for a time period, where the photon is at least partially absorbed by a gas specimen being monitored. The optical power exited from waveguide 902 is inversely proportional the gas concentration in optical cavity 806. The exit optical power from waveguide 902 is then reflected (e.g., by another 45-degree wedge 813) and detected by photo diode 804.

The gas specimens are introduced into the optical cavity 806 and its surrounding areas by etched channels 808 (FIG. 8A). To enhance the gas flow rate in certain cases, the gas flow channels 808 can be equipped with flow manipulators, such as micro heating rings (or those commonly used in inkjet printer nozzles). The flow manipulators can propel the gas flow through out the gas detector device.

Numerical simulation can be performed numerous times in the design of a gas detector using a photonic crystal cavity. For example, numerical simulation can be performed to estimate a sensitivity of the gas detector. Numerical simulation can also be performed in positioning the pillar so that the resonant frequency of the photonic crystal cavity matches the absorption wavelength of the sampled gas.

First, numerical simulation with respect to the estimation of the sensitivity of the gas detector will be discussed. As noted above, the photonic crystal cavity structure of FIG. 9 includes an incident waveguide 901, an optical cavity 806, and an output waveguide 902. In addition, the larger the Q value, the slower the energy decays, and the better the photons are confined.

Suppose a Lorentzian peak is centered at $\omega_0$ (i.e. the resonant frequency) with a FWHM peak width of $\Delta\omega=\omega_0/Q$. By measuring the peak width of the spectral response of such cavities, the Q values can be obtained.

Figure 10:
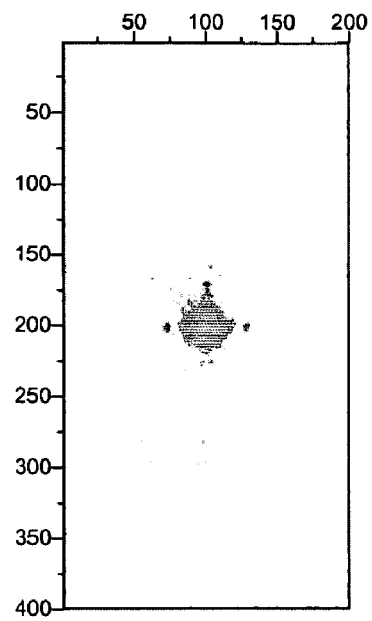
FIG. 10 illustrates a monopole cavity mode of the optical cavity structure of FIG. 9.
Figure 11:
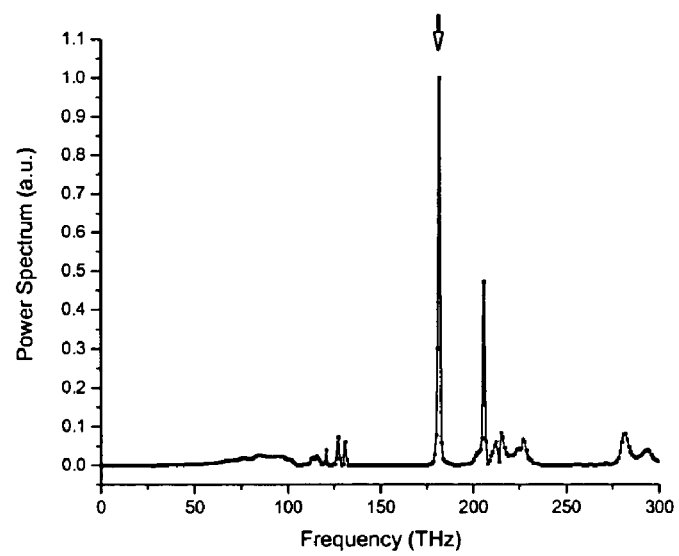
FIG. 11 illustrates a graph of a transmission spectrum generated by performing FDTD based on the optical cavity of FIG. 9.

Still referring to FIG. 9, resonance frequencies can be evaluated for a gas detector device performance by FDTD. The power flow at the exit waveguide 903 can be recorded, and with the power spectrum as plotted as shown in FIG. 11. The resonant transmission peak near 182 THz (labeled by an arrow) is the result of a localized monopole cavity mode supported by the cavity. This monopole cavity mode is well confined inside the cavity, as shown in FIG. 10.

Other minor peaks shown above 200 THz or below 135 THz are results of the remnant transmissions outside the photonic bandgap. These peaks are not near the desired frequencies for this exemplary gas detector device, and do not have to be measured or have any physical consequence in this particular exemplary embodiment, although other exemplary embodiments can be designed to sample these ranges.

As noted above with relation to the time domain Beer-Lambert law, the longer a photon lifetime, the more sensitive a gas sensor can be. In addition, the larger the Q value, the longer a photon lifetime is.

Therefore, the sensitivity of gas sensors can be enhanced by utilizing a high Q cavity mode, which is equivalent to longer photon lifetime. For traditional gas detectors, increased photon lifetime was realized by increasing length L (see FIG. 4) of the device. However, to keep the size of the sensor down, and maintain high sensitivity, multiple-pass optical cavities can be implemented to increase the photon lifetime inside a cavity.

For instance, presuming the structure shown in FIG. 9 did not have an optical cavity, the lifetime of a photon transmitting though the cavity area 806 would be about $10^{-14}$ seconds. However, based on FIG. 11, photons numbers in the optical cavity mode take about $40 \times 10^{-14}$ seconds to decay to 1/e (i.e. ~0.3679) of its initial value. The photon lifetime in this cavity mode is about $40 \times 10^{-14}$ seconds, and the corresponding Q value is ~400. Therefore, with the optical cavity 806, the photon lifetime is enhanced by a factor of 40, which leads to the relative sensitivity of the gas sensor being enhanced by a factor of 40. Due to the linear relation between Q and $\tau_{ph}$, a higher Q value can further enhance the sensitivity.

Figure 12:
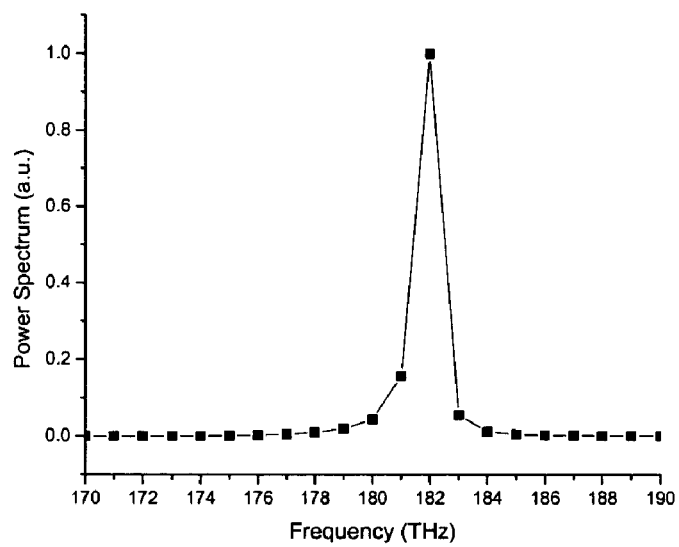
FIG. 12 illustrates a zoom-in view of FIG. 11 in the approximate range of 170 THz to 190 THz.

Referring to FIG. 12, the resonant wavelength of optical cavity 806 can be estimated based on a closer look at the power spectrum obtained at output port 903. FIG. 12 illustrates a zoom-in view of the 170~190 THz region in FIG. 11.

As shown in FIG. 12, the spectral resolution generated by this 1 ps-long-time-sequence is 1 THz. Judging from the asymmetric shape of the peak, it can be seen that a much higher spectral resolution is needed to measure the peak frequency and the peak width.

Figure 13:
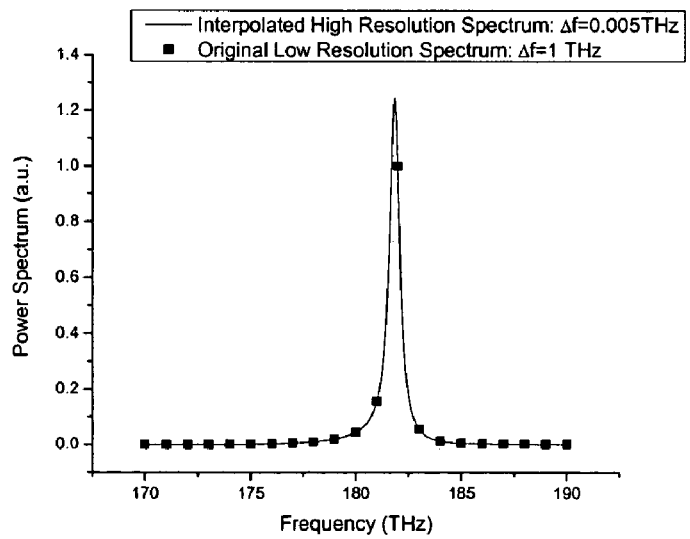
FIG. 13 illustrates the spectral response curve generated by performing rational function interpolation on the FDTD transmission spectrum of FIG. 12.

To illustrate how the numerical simulation as described in FIG. 3 increases speed and improves accuracy of the prediction, the same discrete spectrum plotted in FIG. 12 is used an initial input data. The discrete spectrum was used as the input data to rational function interpolation. After less than 1 second execution of the interpolation routine, a spectrum with 200 times higher resolution, as shown in FIG. 13, was generated.

Figure 14:
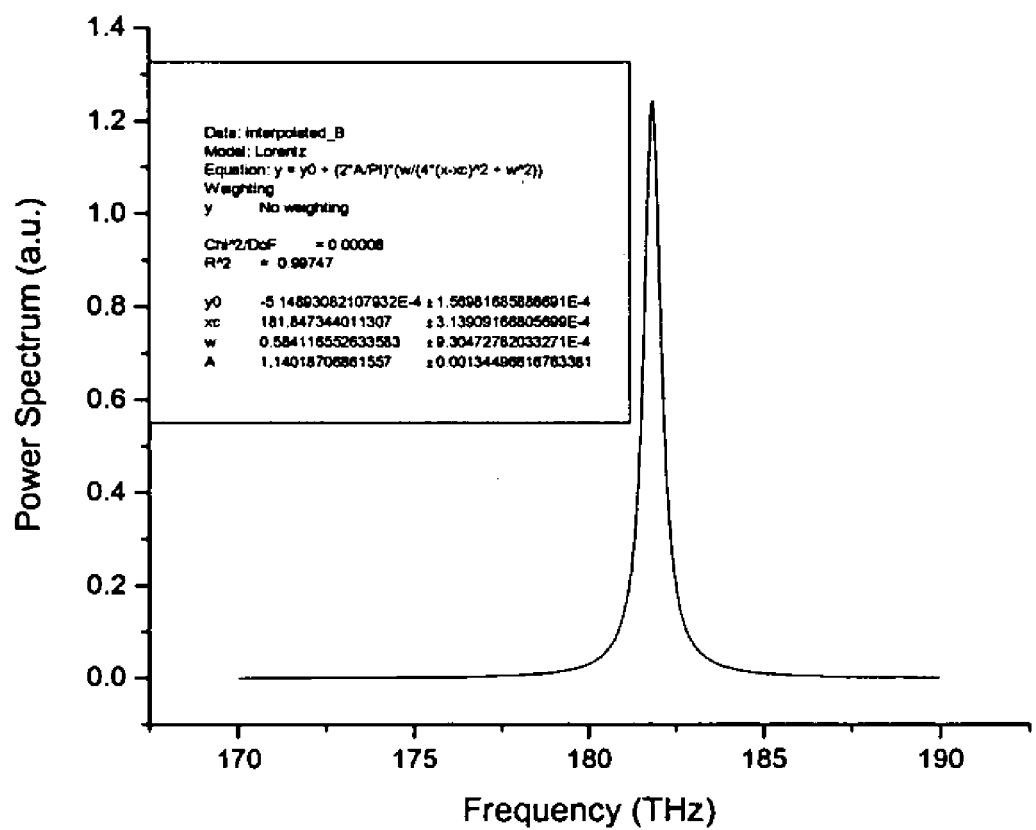
FIG. 14 illustrates the curve generated by performing Lorentzian regression on the spectral response curve of FIG. 13.

Then in the next step, with this high resolution interpolated spectrum as the input data for a Lorentzian regression algorithm, the numerical values of peak frequency and peak width (FWHM) were extracted in less than 1 second, and with very reduced uncertainty. The result of Lorentzian regression is shown in FIG. 14. Although it appears to be similar to the curve shown in FIG. 13, the regression result in FIG. 14 is the plot of an analytical form, which provides the parameter values of interest. In particular, the resonant frequency is 181.8473±0.0003 THz, the peak width, FWHM, is 0.5841±0.0009 THz, and the quality factor Q is 311.3±0.5.

Figure 5:
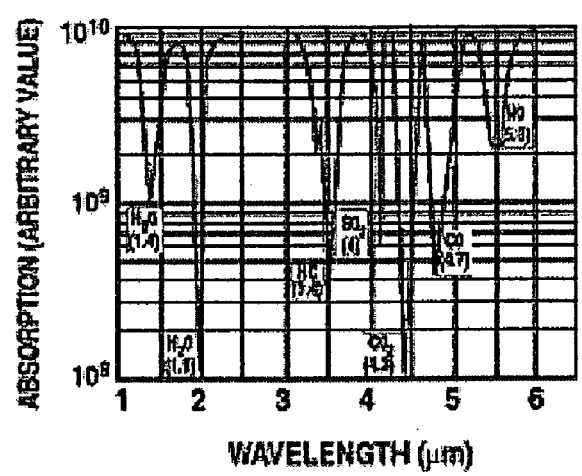
FIG. 5 illustrates a graph depicting unique absorption wavelengths of different gases.

The peak frequency value gives an accurate prediction of whether a resonant frequency of such the optical cavity 806 matches a specific gas absorption wavelength, such as those listed in FIGS. 5 and 6. In addition, the quality factor Q gives accurate prediction of the power of sensitivity enhancement with respect to single-pass sensors.

For this specific example, it can be seen that the resonant frequency 181.8 THz happens to match the absorption frequency of CH4 (Methane) gas exactly according to FIG. 6. And the quality factor of 311.3 means a sensitivity enhancement of 27 times.

Accordingly, the above-described numerical simulation facilitates the determination of the sensitivity of a gas detector using a photonic crystal cavity within a reasonable time. In addition to this use, the numerical simulation can also be used in matching the frequency of optical cavity 806 with the absorption frequency of the gas sample.

Referring back to FIGS. 8A to 8C, to match the resonant frequency of the optical cavity 806 with the characteristic absorption frequency of the chosen gas, an extra pillar 809 can be introduced inside the optical cavity 806.

The position of the pillar can be adjusted in numerous ways. For example, the position of the pillar 809 can be dynamically adjusted by the electrostatic actuator 811 to tune the cavity resonant frequency to overlap the gas absorption frequency exactly.

In another exemplary embodiment, the pillar 809 can be adjusted by separation from other pillars which are for the waveguide. The pillar 809 can be made on a counter substrate, and the substrate for the waveguide can be bonded to the counter substrate containing pillar 809 by alignment mark. A position of a pillar can then be adjusted by fine turning alignment of each substrate during monitoring the resonance frequency from waveguide. This allows for simpler fabrication, but may be more difficult to realize a multi-gas sensor on one substrate, which is discussed later with reference to FIG. 31.

In yet another exemplary embodiment, a piezoelectric device can be used to adjust the position of pillar 809 within the cavity. This allows for easier implementation for a multi-gas sensor, as discussed later with reference to FIG. 26.

Figure 15:
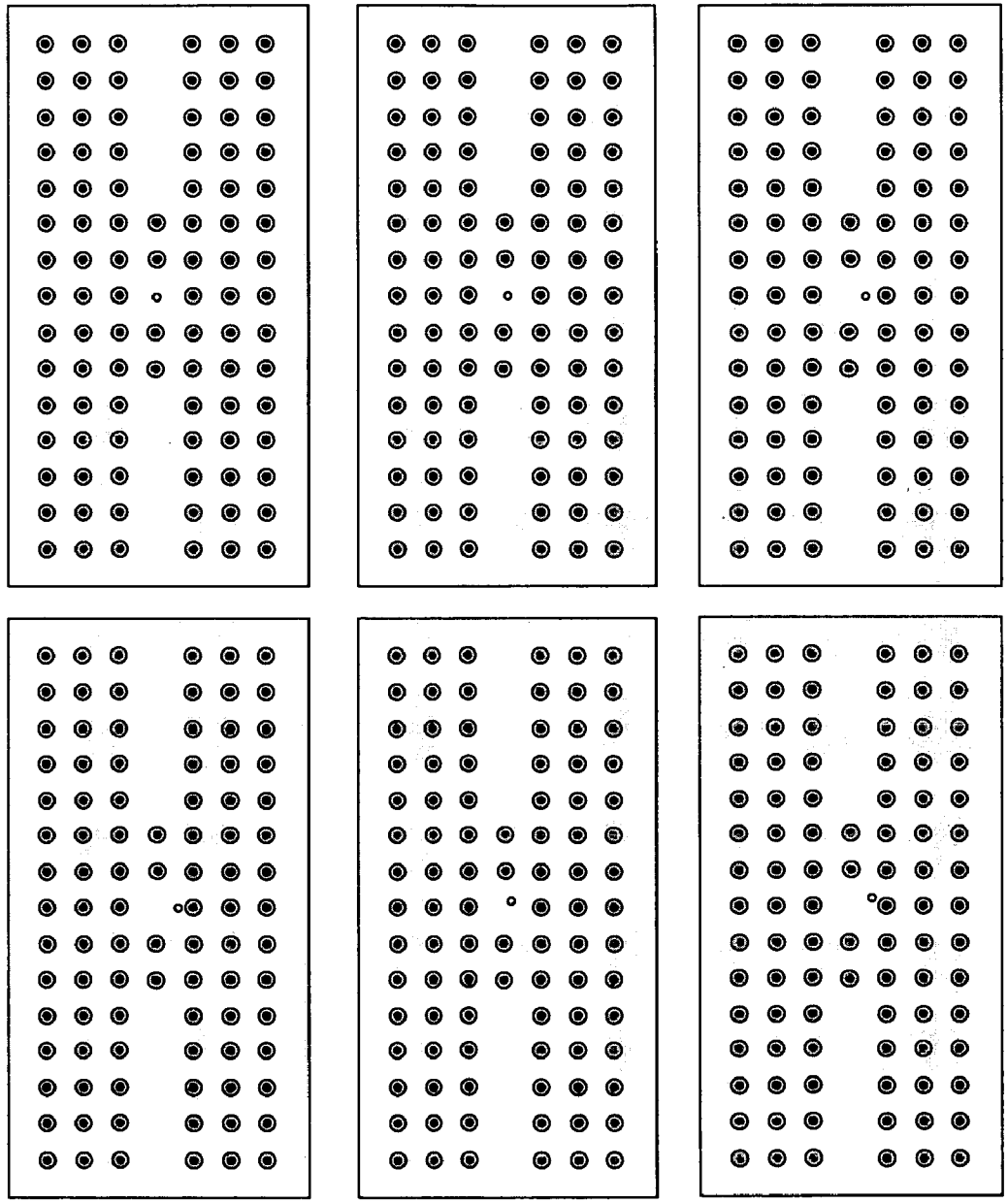
FIG. 15 illustrates six exemplary positions of a pillar for tuning the frequency of the optical cavity of FIG. 9.

Given the mode shape of the monopole mode shown in FIG. 11, the extra pillar 809 can be used to tune the resonant frequency through changing the location of the pillar 809. The extra pillar 809 can be constructed of any type of material that provides a selective effect on cavity frequency when inserted and moved (e.g. Si or GaAs). As an initial test, an extra pillar with a reduced radius (r'/a=0.15) was introduced into the cavity as shown in FIG. 15, with all other pillars forming the photonic crystal having a radius of r/a=0.2. FIG. 15 illustrates 6 exemplified simulated locations (within the total 16 positions simulated). The physical lattice constant (i.e. a) used was 620 nm. It should be noted that the result can be used at different scales, as long as r/a and r'/a are kept constant. It should also be noted that although a reduced size rod was used as the pillar, rods of other sizes can be used.

Figure 16:
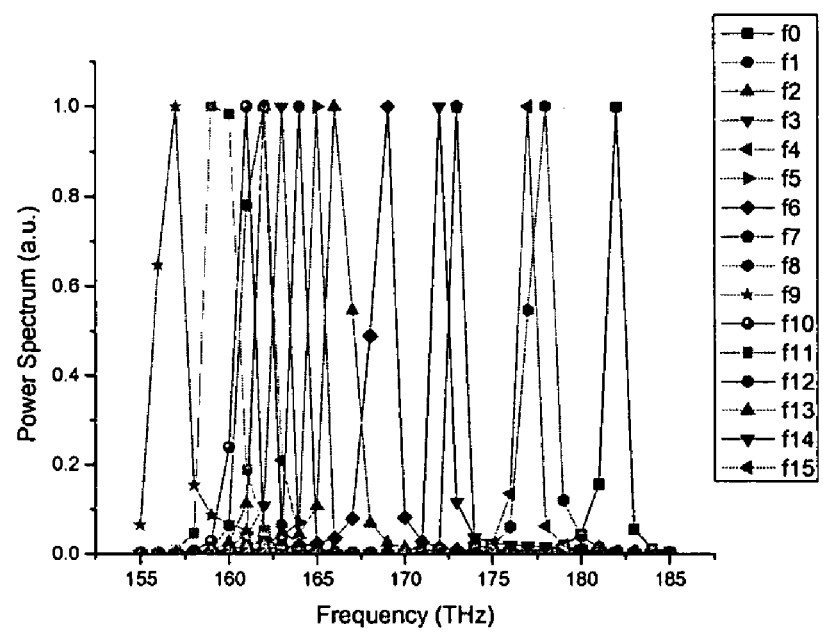
FIG. 16 illustrates a graph of transmission spectrums generated by performing FDTD on 16 exemplary positions of a pillar within the optical cavity of FIG. 9.

16 different positions of the extra pillar 809 were evaluated with results as shown in FIG. 16. The 16 different locations of the extra rods were simulated with 2D-FDTD routine. Each FDTD simulation evolved 1 picosecond numerically. The 1 THz resolution spectra generated by the 16 pillar positions are plotted in FIG. 16.

Referring to the labels 0 to 15, the position "0" corresponds to the absence of the extra pillar 809, and positions 1 through 8 correspond to a position of the pillar 809 moved from the exact cavity center (i.e. x=0, y=0) to the edge of the cavity on the x-orientation (i.e. x=0.63 a, y=0) at a uniform step size of $\Delta x=0.09$ a. Positions 9 through 15 correspond to the position of the pillar 809 being moved from (x=0.09 a, y=0.09 a) to the edge (x=0.63 a, y=0.09), also along the x-orientation.

Although it can be observed that the resonant frequency was tuned in FIG. 16, it is difficult to tell the value of the tuned frequency and the peak width with sufficient accuracy, because the resolution (i.e. 1 THz) does not resolve these peaks, which have FWHMs equal or less than 0.5 THz.

Traditionally, longer FDTD simulations would be required to resolve these peaks. For instance, to obtain a resolution at least 0.1 THz, simulation time would increase 10 times. Given 9.16 minutes consumed for each of the 16 spectra plotted in FIG. 16, a 10-time increase would increase the total FDTD simulation time for 16 positions from about 2.44 hours to about 24.4 hours. From a practical design standpoint, hundreds of simulation runs could be required. For example, given a reasonable estimation of 160 positions, the time for performing FDTD simulation increases by a factor of 10, totaling more than 10 days of computation time. This is not a practical solution for the design and use of gas detector device.

Using the above-described numerical simulation, rational function interpolation can be performed to generate accurate predictions of high resolution spectra within a few seconds. Such predictions are plotted in FIG. 17. The spectra shown in FIG. 17 have 200 times higher resolutions than those shown in FIG. 16. Yet, the generation of FIG. 17 from FIG. 16 required only a few seconds of computation time.

Figure 17:
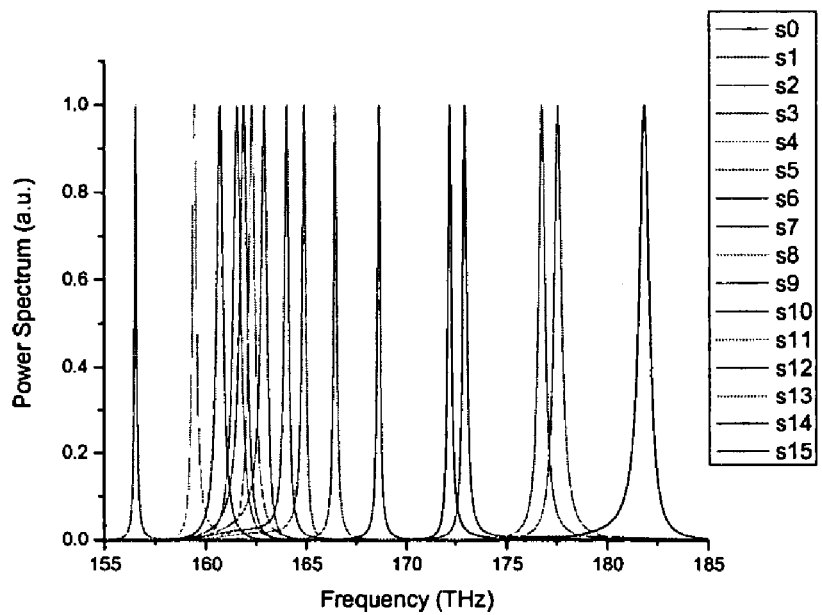
FIG. 17 illustrates the spectral response curves generated by performing rational function interpolation on the FDTD transmission spectrums of FIG. 16.

Then, using the numerical simulation, Lorentzian regressions are applied on the interpolated high resolution spectra shown in FIG. 17. These Lorentzian regressions require about 1 second of computation time. However, accurate values of resonant frequencies and sensitivity enhancement factors are determined, as illustrated in FIG. 18.

Figures 18, 19:
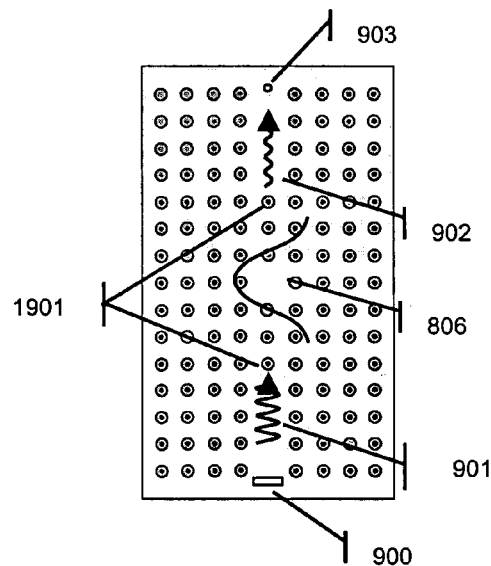
FIG. 18 illustrates a table depicting parameter values obtained by performing Lorentzian regression on the spectral response curves of FIG. 17.
FIG. 19 illustrates an exemplary embodiment of a gas detector in which additional periods are added to the photonic crystal cavity structure.

With reference to FIG. 18, the sensitivity enhancement factors range between 27 and 143. In practice, a higher enhancement factors, between a few hundreds to a few thousands, may be desired. To realize higher enhancement factors, additional periods can be added to the photonic crystal between the I/O waveguides and the optical cavity as shown in FIG. 19. In FIG. 19, additional periods 1901 of photonic crystal were added on each side of the cavity 806.

With the addition of the periods 1901, the lifetime of the photon inside the cavity can increase significantly. Likewise, the sensitivity enhancement factors can increase. FDTD simulations were performed at the same length (i.e. ~2.44 hours) as before. However, the original 1 THz resolution spectra were not seen to provide a high enough resolution for detecting the existence of some of the resonant peaks.

Figures 20, 21:
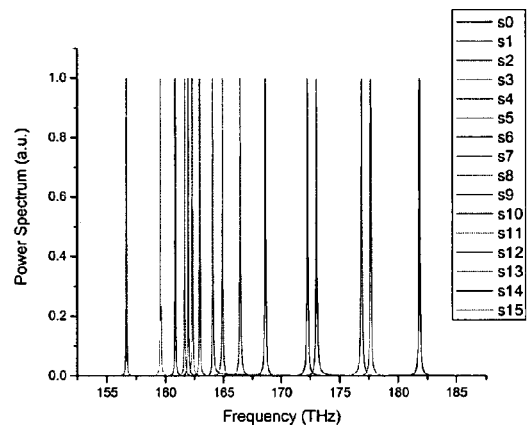
FIG. 20 illustrates the spectral response curves generated by performing rational function interpolation on FDTD frequency points corresponding to 16 exemplary positions of a pillar within the optical cavity of FIG. 19.
FIG. 21 illustrates a table depicting parameter values obtained by performing Lorentzian regression on the spectral response curves of FIG. 20.

Using the numerical simulation described with reference to FIG. 3, fine spectral features were identified as shown in FIG. 20 in reduced time. The much narrower spectral features in FIG. 20 compared with those in FIG. 17 is a suggests the longer photon lifetime as a result of better optical confinement provided by the extra periods 1901 of photonic crystal lattice.

The list of peak frequencies and sensitivity enhancement factors were generated by performing Lorentzian regression, without any increase of FDTD simulation time, as shown in FIG. 21.

For an FDTD simulation with a resolution of $\Delta f$ at least 0.01 THz to test 160 positions, approximately 2,440 hours (>100 days) would be required. However, using the above-described numerical simulation, improved resolution and accuracy can be achieved in approximately 1 day (i.e. 24 hours). As such, design and use of a gas detector is seen to become more manageable. Accordingly, an increased yield in mass production can be realized. In addition, the time required for trouble shooting such a gas detector can be reduced.

Figure 22:
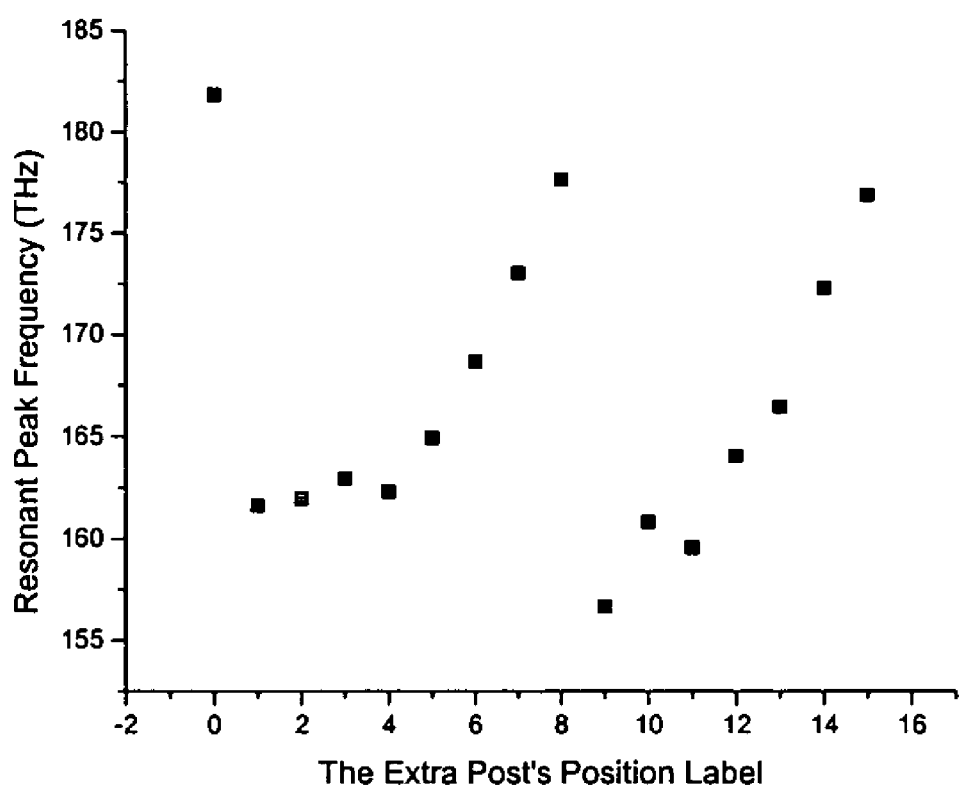
FIG. 22 illustrates a graph of the resonant frequencies of FIG. 21.
Figure 23:
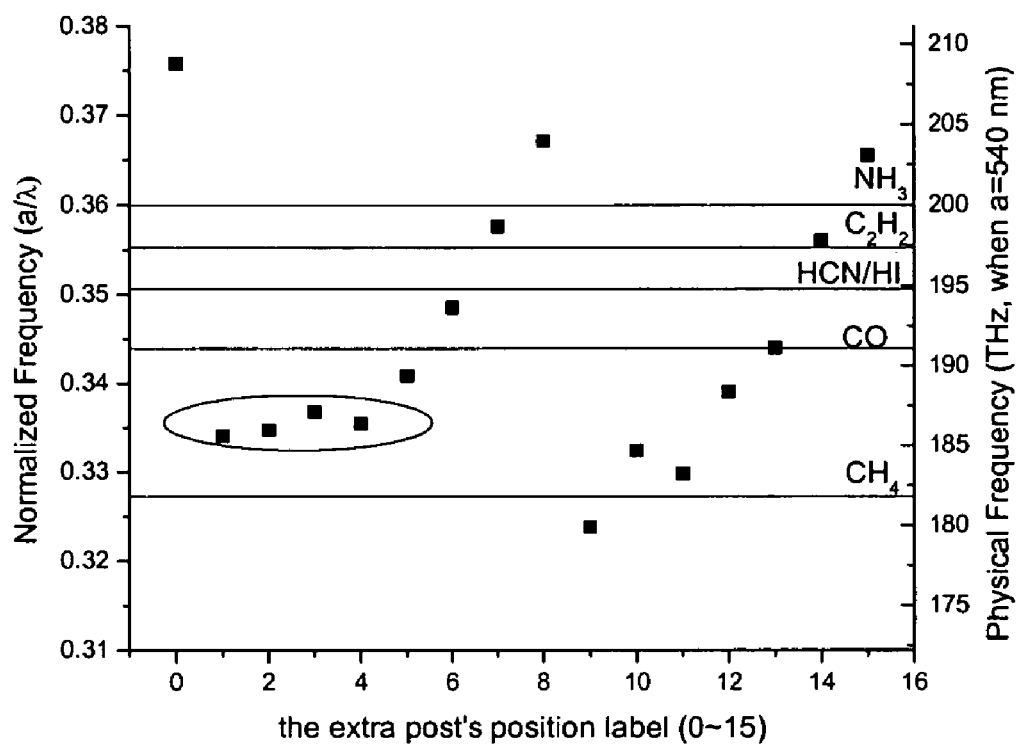
FIG. 23 illustrates a graph of the resonant frequencies of FIG. 21 in which a stable condition of resonance frequency is circled.

FIG. 22 illustrates different regions tuning using various pillar positions. In some part, the tuning curves have relatively high slope, which lead to the capability to tuning the resonant frequency for a large spectral range. As illustrated in FIG. 23, in the high slope regions, a change in pillar position can facilitate large spectral range tuning, where there can be overlapping of the cavity resonant frequency with multiple gas species. Thus in at least one exemplary embodiment, varying the position of an extra pillar in a photonic crystal cavity can tune a photonic crystal having fixed bulk photonic crystal properties (e.g. photonic crystal lattice constant, r/a ratio, material refractive index etc.). Note that although discussion of at least one exemplary embodiment refers to the adjustment of a pillar in a cavity, at least one exemplary embodiment can use a hole to achieve the same effect, and the location of he hole can be varied.

Figure 24:
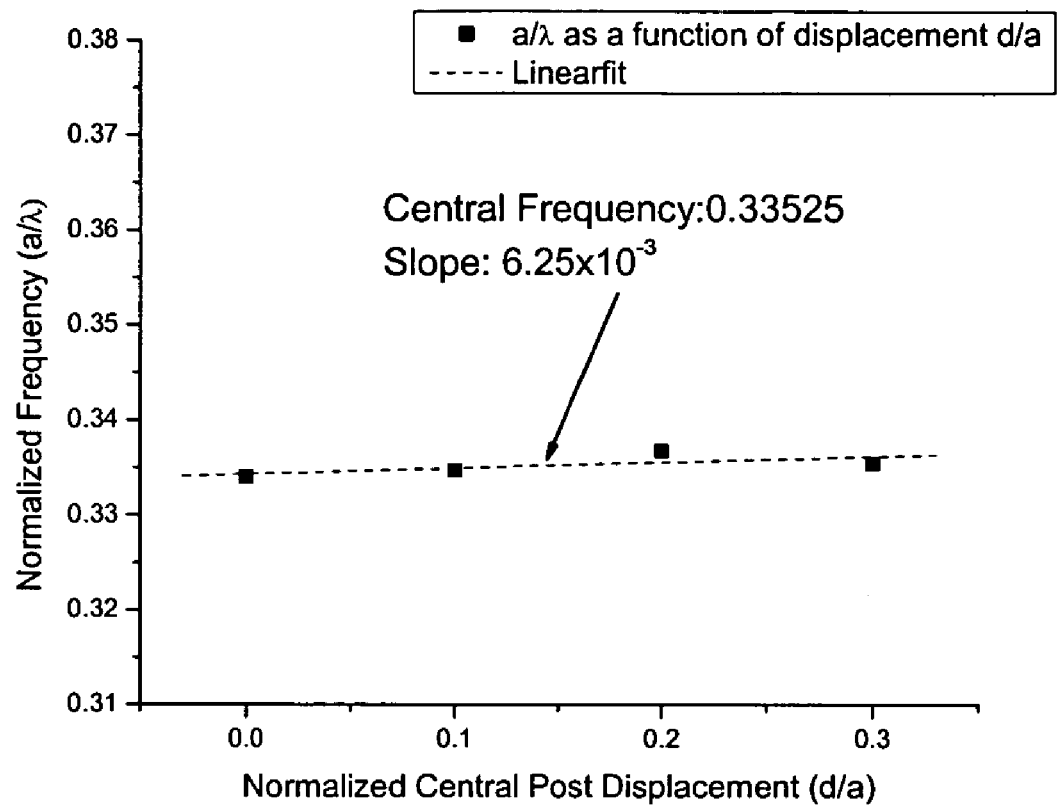
FIG. 24 illustrates an expanded view of the circled portion of FIG. 23.

Other exemplary embodiments can utilize the low slope regions (e.g. the circled region in FIG. 23). For instance, to reduce the fabrication cost of a certain device, the position tuning mechanism can have coarse position resolution and/or stability using pillar positions in the low slope region. In the low slope region, minor variations of the central pillar position do not have significant impact on the resonant frequency (i.e. device performance). Therefore, using this part of the curve, we can also realize higher device fabrication yield. For instance, for Q~1000, the tolerance in normalized frequency is ~±3.5×10$^{-4}$. Using the slope of 6.25×10$^{-3}$ shown in FIG. 24, the tolerance in d/a is ~±0.05. Given a~500 nm, the tolerance in the displacement position is ~25 nm.

Figures 25, 26:
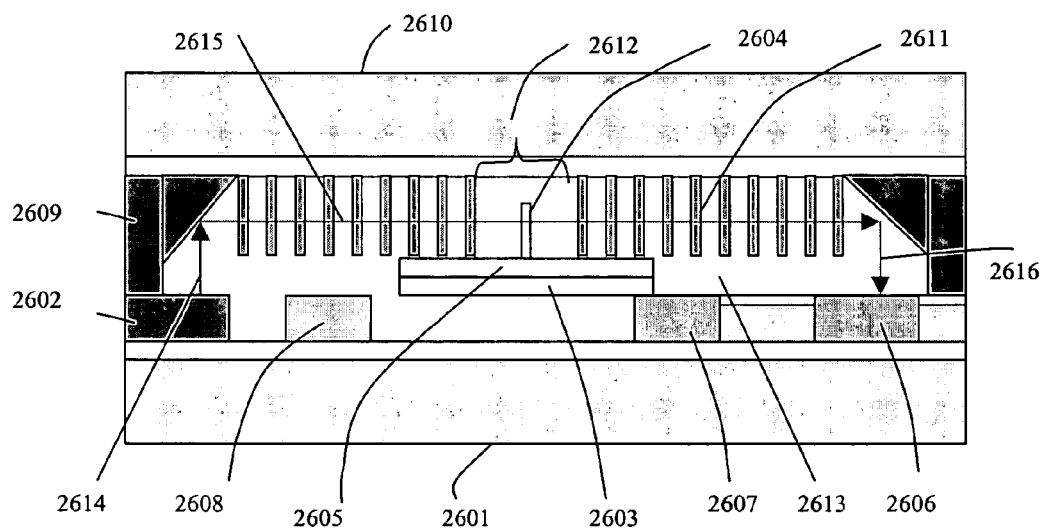
FIG. 25 illustrates a table with lattice constants corresponding to different gases.
FIG. 26 illustrates a second exemplary embodiment of a gas detector which uses a photonic crystal cavity.
Figure 27A:
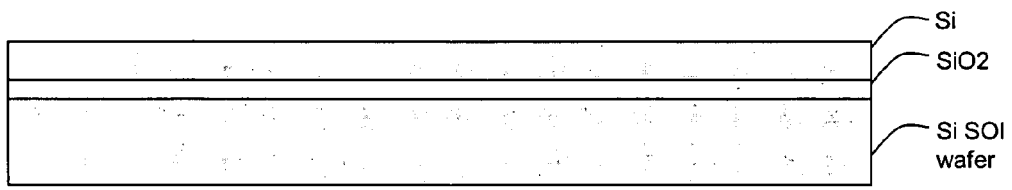
FIGS. 27A to 27F illustrate the fabrication of an active substrate of FIG. 26.
Figure 27B:
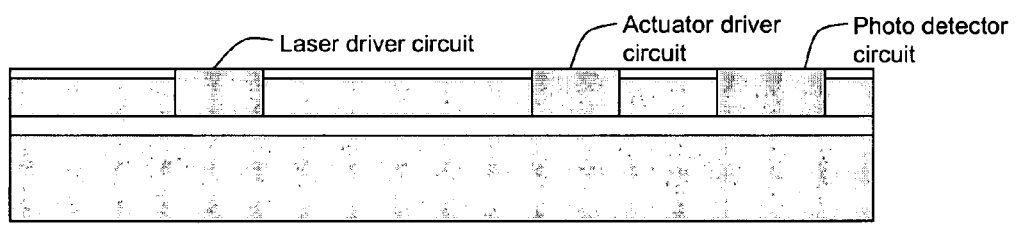
Figure 27C:
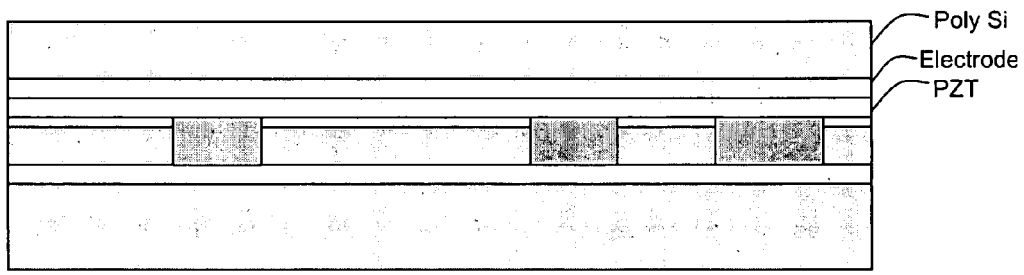
Figure 27D:
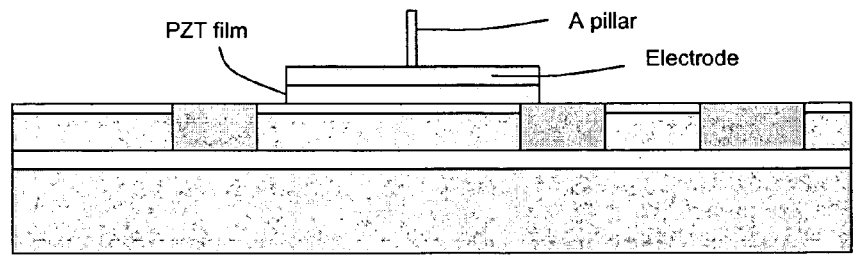
Figure 27E:
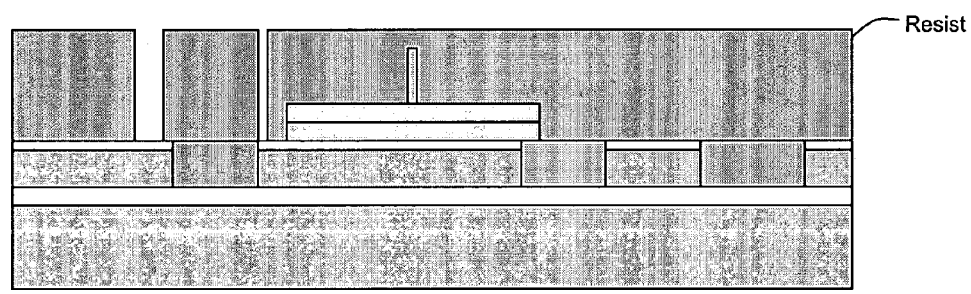
Figure 27F:
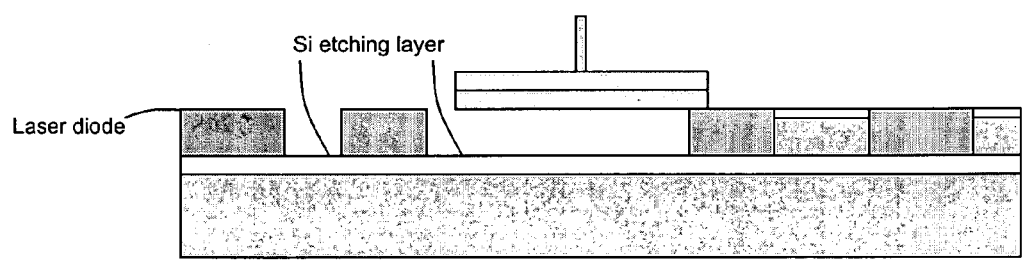

As illustrated in FIG. 23, exemplary embodiments that use the low slope region could be insensitive to the detection of multiple gas species upon small pillar position changes. Thus, these particular embodiments can lose the wide spectral range tunability to accommodate multiple gas species in one fixed bulk photonic crystal properties (e.g. photonic crystal lattice constant, r/a ratio, material refractive index etc.). However, this does not prevent embodiments from integrating multiple sensors on a single substrate or a single sensor with varying photonic crystal properties for multiple gas species. For example exemplary embodiments having pillar positions in the low slope region can shift the physical wavelength (or frequency) of the low slope region by scaling the bulk photonic crystal lattice constants. FIG. 25 is a table listed the respective lattice constants should be used to scale the low slope region to overlap with various gas species. With this technique, multiple gas sensors constructed by different lattice constant photonic crystals can still be integrated on a common substrate. Each of them target one specific gas, and with its performance not vulnerable to minor variations of the extra pillar's position. In additional exemplary embodiment the relative position of each pillar can be similarly situated within their respective cavity (e.g. same approximate distance from the walls of the cavity).

Additionally a single sensor can be constructed to vary the photonic crystal properties during operation. Thus a pillar in a low slope region can still sample various species of gases by varying the photonic crystal properties. For example the photonic crystal can be of a type subject to the Pockels or Kerr effect where the refractive index can be changed in proportion to or as the square of an applied electric field. Additionally the lattice constant can be changed. For example one can build the photonic crystals on a stretchable substrate, say an piezoelectric substrate or even a stretchable plastic substrate, or one can heat the photonic crystal to change both the refractive index and lattice constant.

FIG. 26 illustrates a second exemplary embodiment of a gas detector which incorporates a photonic crystal cavity. The gas detector of FIG. 26 is similar in some aspects to the gas detector illustrated in FIGS. 8A to 8C. Among its differences, however, are the arrangement of the actuator for positioning the pillar, the use of spacers between top and bottom substrates, and the use of a passivation coating film (not shown).

The gas detector includes substrate 2601 (e.g., Si), referred to as the "active" substrate, having an integrated laser diode 2602 (e.g., VCSEL (vertical cavity surface emitting laser)), and a piezoelectric actuator 2603 to control the position of a pillar 2604. Pillar 2604 is operatively connected to the top of a cantilever 2605. The gas detector can also include a detector 2606, a driver circuit 2607 for actuator 2603, a laser diode driver circuit 2608, a detector circuit and its processing circuit, and a passivation coating film (not shown) to prevent erosion by an active gas. Spacer 2609 keeps a gap between substrates 2601 and 2610. All of the active functions can be integrated into substrate 2601.

Counter substrate 2610 (e.g., Si), referred to as the "passive" substrate, includes of waveguide 2611 and cavity 2612. After making each of the active and passive substrates 2601 and 2610, the substrates can be bonded, and aligned by an alignment mark.

When detecting gas, a laser light 2614 is emitted from laser diode 2602, and the light is reflected by a mirror and directed into waveguide 2611. The propagated light 2615 travels through the waveguide through optical cavity 2612 and is reflected by an additional mirror, thereby directing the reflected light 2616 to detector 2606. If the sample gas, in the cavity, corresponds to a gas that absorbs the designed wavelengths in the band gap spectrum, the absorption will vary the light intensity, and thus gas can be detected.

As noted above, there are different ways in which the pillar can be positioned, such as by separate substrate or a piezoelectric device. Using a separate substrate may allow a pillar to be adjusted, but may not be well-suited for a multi-sensor device as described later with reference to FIG. 31. On the other hand, for a piezoelectric device, it may be difficult to deploy an actuator and waveguide simultaneously in one substrate. Accordingly, in this exemplary embodiment (FIG. 26), the waveguide 2611 can be separated from the actuator unit, and the actuator unit 2603 can be deployed near the optical cavity 2612.

It should be noted that the height of the pillar 2612 and spacers can provide for added stability. The height of pillar can be varied to utilize the 2D photonic crystal effects, where the height of spacer is higher than that of pillar (e.g., a 4 μm height). Other heights of the pillar can be used, for example from 0.6 μm to 6 μm, depending on the working light wavelength. After bonding the passive and active substrates to each other, the pillar should not come into contact with the opposing substrate. Accordingly, the pillar structure is seen to be stable.

In addition, thermal management is improved. Since the laser diode 2602 may generate heat, it could interfere with the pitch of the pillar 2604 due to high temperature. This is more applicable if the high temperature part is close to waveguide in the same substrate. However, in this second exemplary embodiment of the gas detector, the cavity 2612 and pillar 2604 are separated from active devices such as the laser diode 2602 and detector 2606. Accordingly, improved stable performance can be realized.

In addition, it should be noted that a gas detector device may have to measure gas that is active. As such, the gas detector containing a photonic crystal cavity may also include a passivation coating film, resulting in an improved durability of the gas detector device.

Figure 28A:
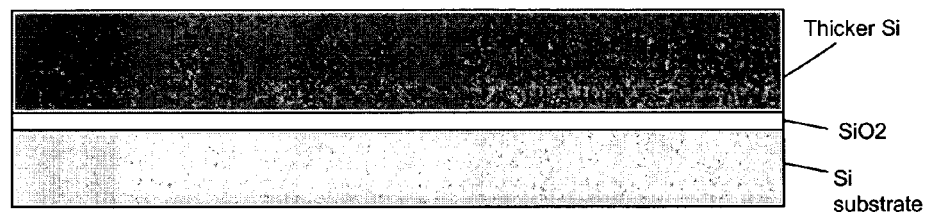
FIGS. 28A to 28C illustrate the fabrication of a passive substrate of FIG. 27.
Figure 28B:
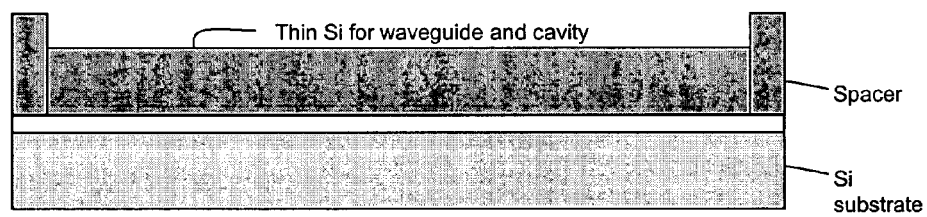
Figure 28C:
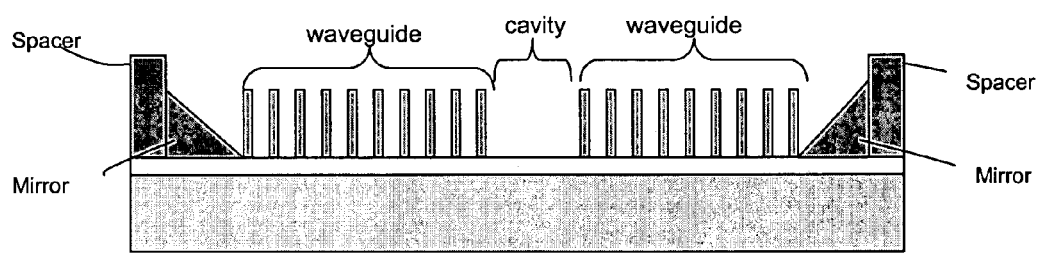

Turning to the fabrication of this gas detector device, FIGS. 27A to 27F illustrate the manufacture of the active substrate, and FIGS. 28A to 28C illustrate the manufacture of the passive substrate.

With reference to FIGS. 27A to 27F, the process flow for fabrication of an active substrate on SOI wafer is illustrated. A CMOS (complementary metal oxide semiconductor) circuit is made for the laser, actuator, and detector. A PZT (Plumbum Zirconate Titanate) film, electrode, and poly-Si layer are then deposited on $SiO_2$ continuously. The poly Si can vary in thickness (e.g. 4 µm), as the pillar can. Next, the electrode is patterned as the shape of an inter-digital transducer by etching. A pillar is then patterned by a LIGA process, so that a high aspect ratio pillar can be obtained. Si layer is then covered with a resist layer. The bottom of actuator can be removed by selective etching process (e.g. wet etching). It can be seen that the electrode with PZT film was connected to the actuator driver at one side. The position of the pillar can therefore be adjusted by the actuator in this substrate. In addition, the surface emitting laser diode can be placed on $SiO_2$ after the sacrificed Si layer for adjusting the height at bonding.

FIGS. 28A to 28C illustrate the fabrication of a passive substrate of FIG. 26, which corresponds to an "opposite" substrate relative to the active substrate of FIGS. 27A to 27F. The opposite substrate (e.g., Si) can vary in thickness, for example as thick as 5 µm. A spacer can be utilized to keep the gap between the active and passive layer, as well as the waveguide and cavity, constant. The layer at the area of waveguide and cavity is etched slightly so that the height of the pillar is less than that of the spacer. By using the same process as for the active substrate, pillars can be patterned for the waveguide and the cavity simultaneously. In addition, mirrors are placed or etched, and can be aligned to the position of the laser and detector in the active substrate.

Figure 29A:
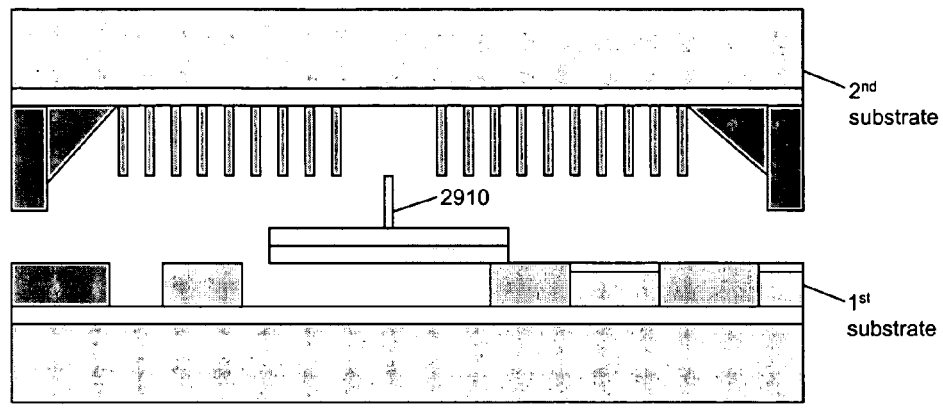
FIGS. 29A and 29B illustrate the bonding the active substrate of FIGS. 28A to 28F with the passive substrate of FIGS. 28A to 28C.
Figure 29B:
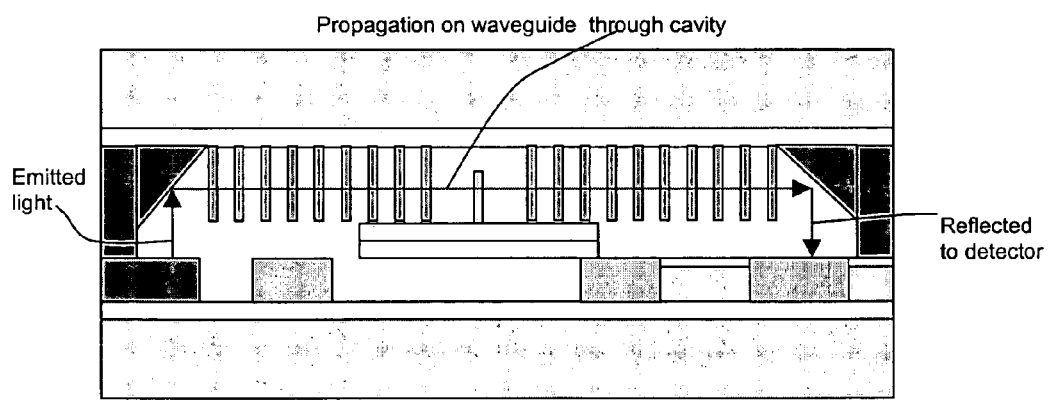

The bonding process of the active and passive layers is discussed with reference to FIGS. 29A and 29B. After both substrates are prepared, the substrates can be aligned by a mark (e.g. raised pin and hole arrangement), and the substrates are bonded to each other. As noted above, the thickness of the spacer can be thicker than that of pillar. The top of pillar should not contact the surface of the opponent substrate. In addition, the top of the pillars in waveguide should not contact the surface of the electrode for the actuator. As such, the likelihood of deformation of the pillar through the bonding process is reduced.

After bonding each substrate, laser light can be emitted from the VCSEL, so that light is reflected by the mirror and directed into the waveguide. The light is propagated in the waveguide through the cavity and is reflected by the mirror at the other side, which is monitored by the detector. In order to tune the resonance frequency, the position of a pillar 2910 can be positioned by the actuator, and then fixed (e.g., by glue). In additional exemplary embodiments, the position of the pillar can be varied between sampling to sample various gases with the same chamber.

Figure 30:
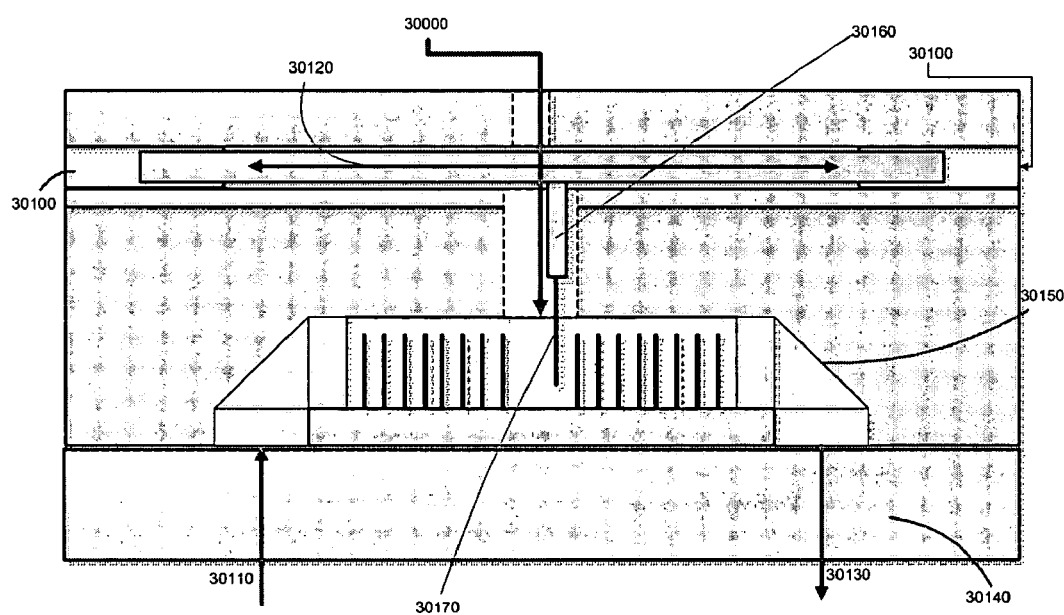
FIG. 30 illustrates a third exemplary embodiment of a gas detector using a photonic crystal cavity.

In at least one embodiment of a gas detector in accordance with the exemplary embodiments, the photonic crystal cavity is isolated from the sampling environment to minimize contamination gases from giving false readings. FIG. 30 illustrates a third exemplary embodiment of a gas detector which incorporates a photonic crystal cavity in a more isolated environment.

With reference to FIG. 30, sample gas enters via channels 30000 on either side of a support arm. The sampling inlet can be exposed to the environment to be sampled, and could also contain a shutter, to take an isolated sample in time. The gas detector of this third exemplary embodiment can include at least one comb drive 30100, with comb drive motion represented by reference numeral 30200. Light from a source 30110 passes through the photonic crystal cavity for subsequent detection (light to the detector 30130). As noted above, a light source and detector chip can be included on a substrate 30140, wherein the substrate 30140 can be isolated from and/or attached to a substrate for the photonic crystal cavity. A reflector can reflect source light 30110 to pass through the photonic crystal cavity, and a reflector 30150 can further reflect the light 30130 to a detector. The reflector 30150 can be made of different solid material of different index of refraction.

The gas detector of this third exemplary embodiment can also include a frequency rod selection arm 30160 and frequency selection rod 30170. The frequency selection rod 30170 can be moved in a vertical direction, can be positioned on a platform which rotates, or rotational gear motion can be converted into translational motion without using comb drives.

In at least one exemplary embodiment, an established pre-cleaning process can be used to clean the cavity of contaminant gases. Such a pre-cleaning process can be viewed as a reset process for the gas detector. For example, a vacuum and purge of the remaining gas can be applied (as well as possible heating to outgas possible contaminants), and a reference inactive gas such as $N_2$ can be introduced. The gas (sample and reference gas) can be delivered to the cavity and through the passage via micro channel nozzle inlets and outlets on the waveguide substrate.

Accordingly, with reference to the exemplary gas detectors described above, a device for detecting a gas sample with increased sensitivity and reduced size can be realized. By using a nearly alignment free integration structure to each component (except the adjustment of resonance frequency), a device with improved reliability and decreased cost can also be realized.

Until now, design of an individual enhanced gas sensors has been described. However, design of a multi-gas detector device is also possible in accordance with exemplary embodiments (e.g., a movable pillar embodiment as discussed in paragraph [204]). Accordingly, design of an array of enhanced gas sensors for different gas specimens in a common photonic crystal platform will now be discussed. Such an array can provide for improved multi-gas detection.

Figure 31:
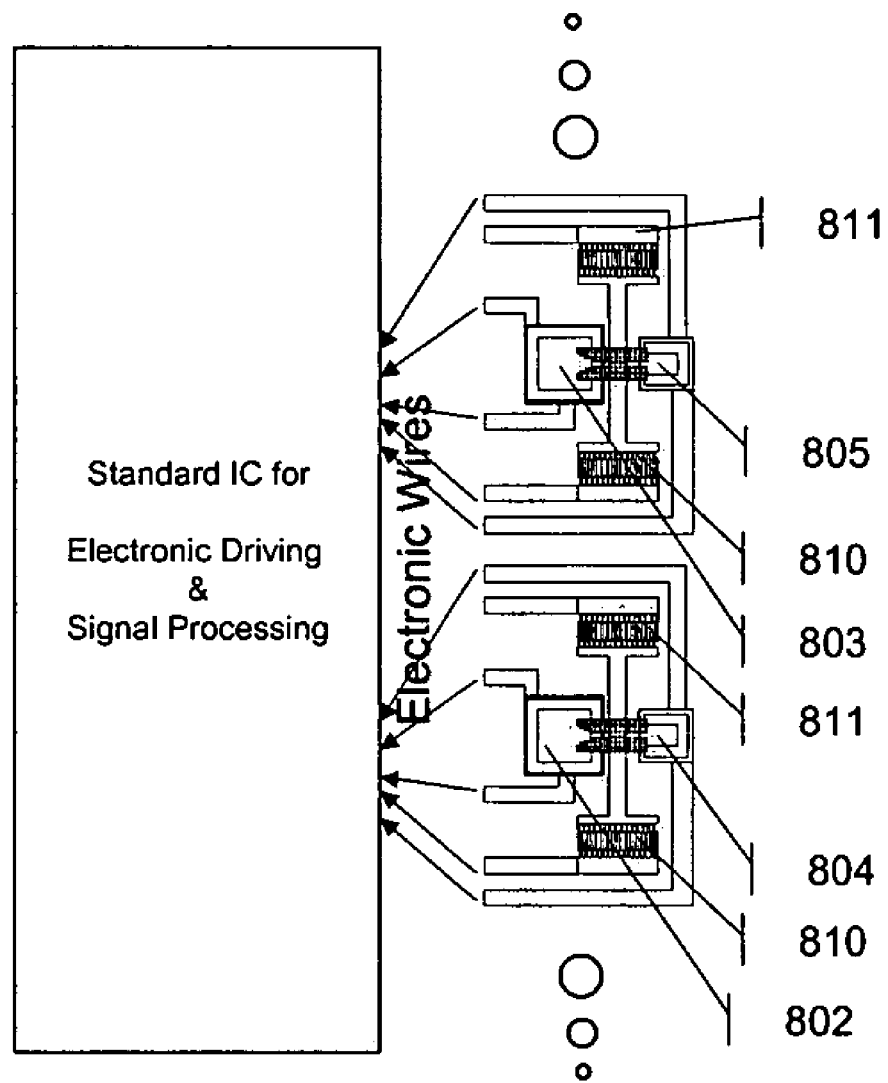
FIG. 31 illustrates an exemplary embodiment of a multi-gas detector device, in which individual gas detectors having photonic crystals are arranged in arrays on a common semiconductor substrate.

Referring to FIG. 31, each of the gas detector devices in the exemplary embodiments can be arranged in arrays on a common semiconductor substrate. Each element gas sensor in the array can be tuned to detect a different gas. In addition, all of the elements can be driven by integrated circuit electronic drivers and signal processing function blocks on the same semiconductor substrate.

In at least one exemplary embodiment, the frequency in the optical cavities can be tuned by a moveable pillar within each cavity. To determine whether an absorption frequency has been reached, one can easily compare the correlation table between the performance and the displacement of the pillar.

Figure 32:
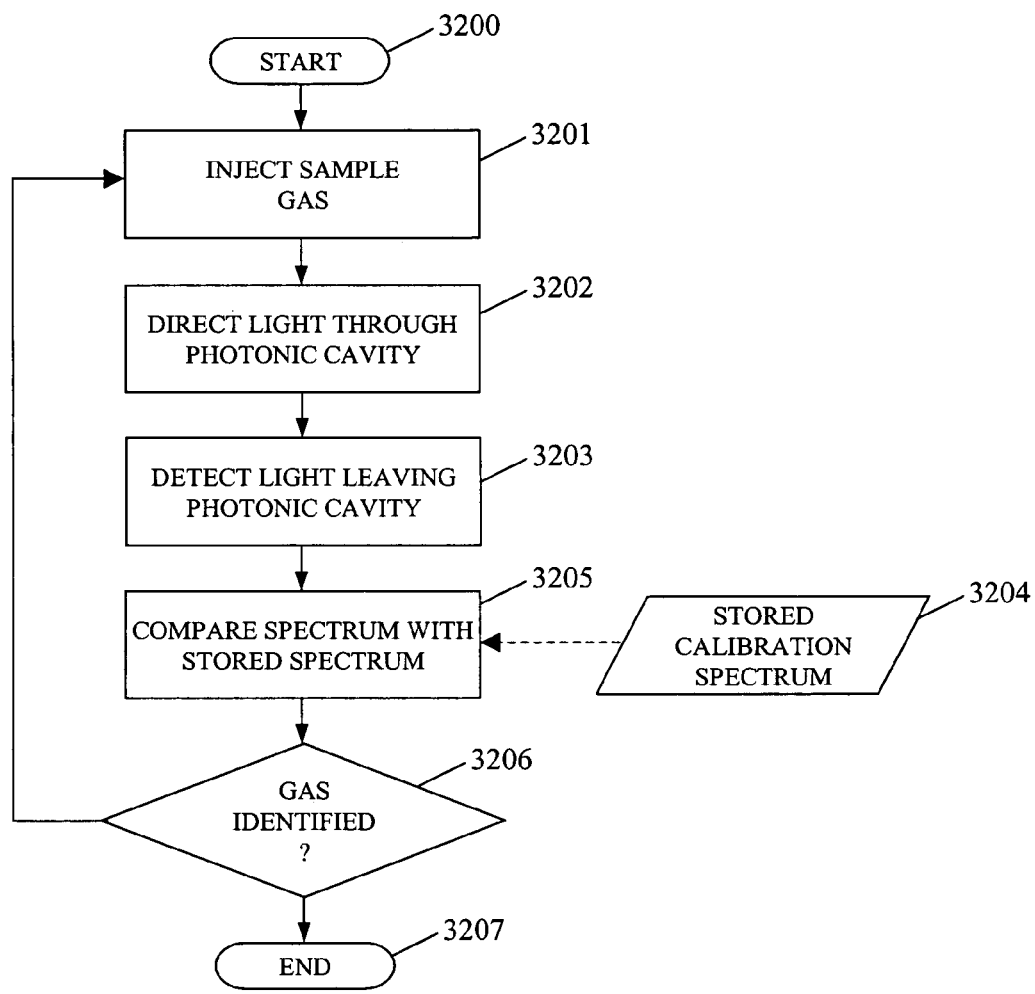
FIG. 32 illustrates a flowchart depicting at least one exemplary embodiment for detecting multiple gas samples.

FIG. 32 illustrates a flowchart depicting at least one exemplary embodiment for performing analysis of a multiple gas samples using photonic crystal cavities. Following start bubble 3200, a sample gas specimen is injected into the photonic crystal cavities of a multi-gas detection device via inlet channels (block 3201). Light having wavelengths associated with various gas absorption wavelengths, for which the photonic cavities are designed to allow to pass (e.g. the light can be directed via waveguides), is directed through the photonic cavities (block 3202). Next, light leaving the photonic cavities is detected via detectors, where the leaving light is directed by a waveguide to each detector, and spectrums of detected light are determined (block 3203). The spectrums of the light detected are compared with stored calibration spectrums of the photonic cavities (block 3205). A determination is then made as to whether the comparison identifies a particular type of gas, using the amplitude reduction of particular band gap peak frequencies (decision diamond 3206). If a particular type of gas is not identified, the process returns to block 3201. Otherwise, the process ends (end bubble 3207).

In addition to using the above described numerical simulation for the design of gas detectors, the numerical simulation, as described with reference to FIG. 3, can also be useful in a photonic crystal design device. In particular, the numerical simulation can assist in the design and use of photonic crystal devices for evaluating and analyzing photonic crystal input.

Figure 33:
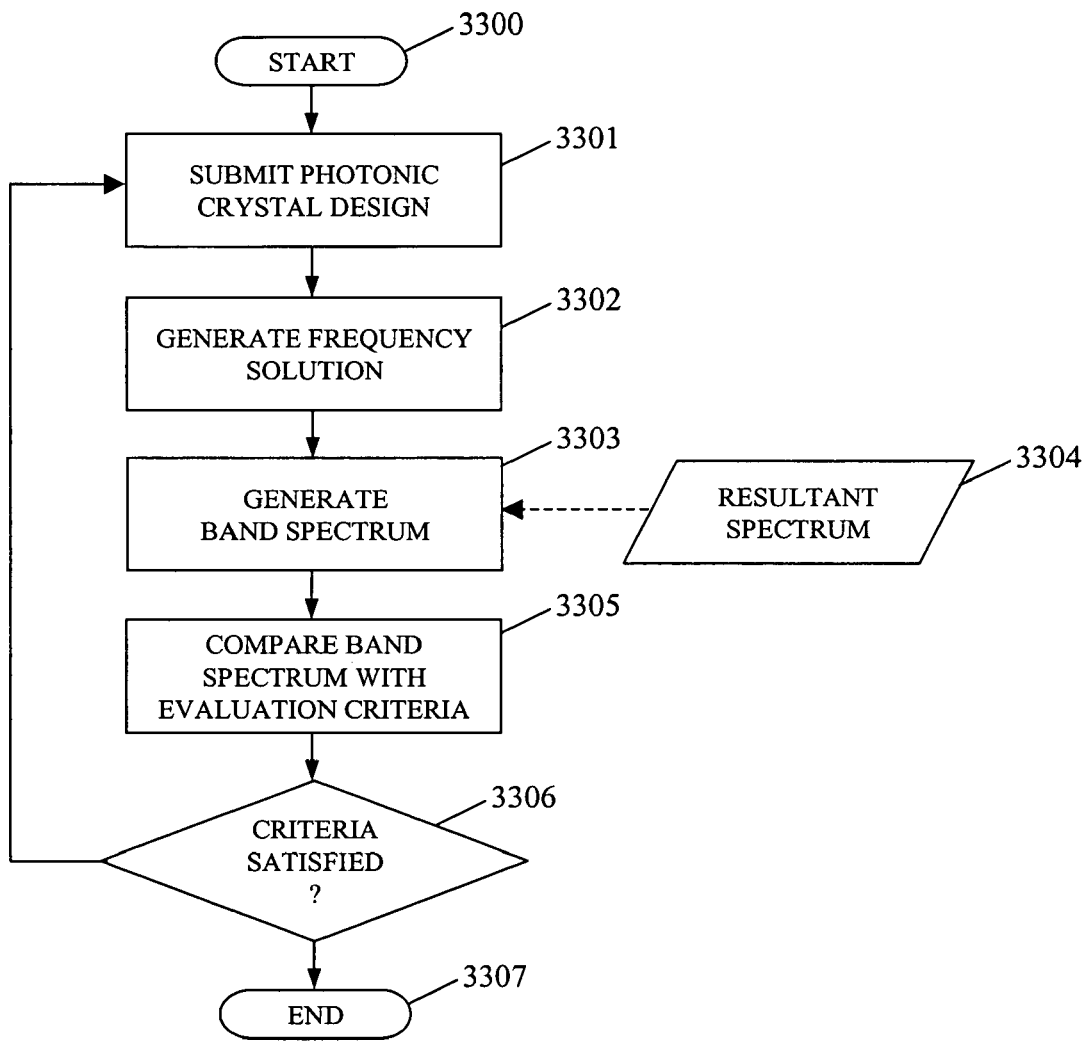
FIG. 33 illustrates a flowchart depicting at least one exemplary embodiment of a photonic crystal design device for evaluating whether data corresponding to a proposed photonic crystal structure meets desired design characteristics.

FIG. 33 illustrates a flowchart depicting at least one embodiment for evaluating whether input data corresponding to a proposed photonic crystal meets desired design characteristics. Following start bubble 3300, photonic crystal design and evaluation criteria are submitted (block 3301). One can construct a computer program that accepts photonic crystal data (e.g. dimensions, material, dielectric constant, boundary condition fields) associated with a particular photonic crystal design. In addition, as stated, evaluation criteria (e.g. target wavelength) can be entered. A frequency solution is then generated for Maxwell's equation for the photonic crystal design (block 3302). The photonic crystal data can be used in the software that solves Maxwell's Equations in the frequency domain (e.g. FDTD, TMM, FEM, and PWE) to obtain coarse data on the band gap spectrum. Next, a band gap spectrum is generated using the numerical simulation described above with reference to FIG. 3, and the resultant spectrum 3304 is produced (block 3303). The coarse data can be used in the algorithm discussed in this paper to derive detailed band gap spectrum (resultant spectrum 3304). The resultant band gap spectrum, 3304 can be stored on computer readable medium (e.g. RAM, hard disk, flash memory). The resultant spectrum is then compared with the evaluation criteria (block 3305). A determination is then made as to whether the resultant spectrum 3304 satisfies the evaluation criteria (block 3306). If the resultant spectrum 3304 satisfies the evaluation criteria (e.g. has a peak frequency within a desired bandwidth inside the band gap structure) the user can be notified, and the process ends (end bubble 3307). If the criteria is not satisfied, the user can be notified and the process repeated by returning to block 3301 where the user can submit a new photonic crystal design. Accordingly, a designer using the above process can speed analysis time between submitted design photonic crystal structure to minutes instead of days.

Figure 34:
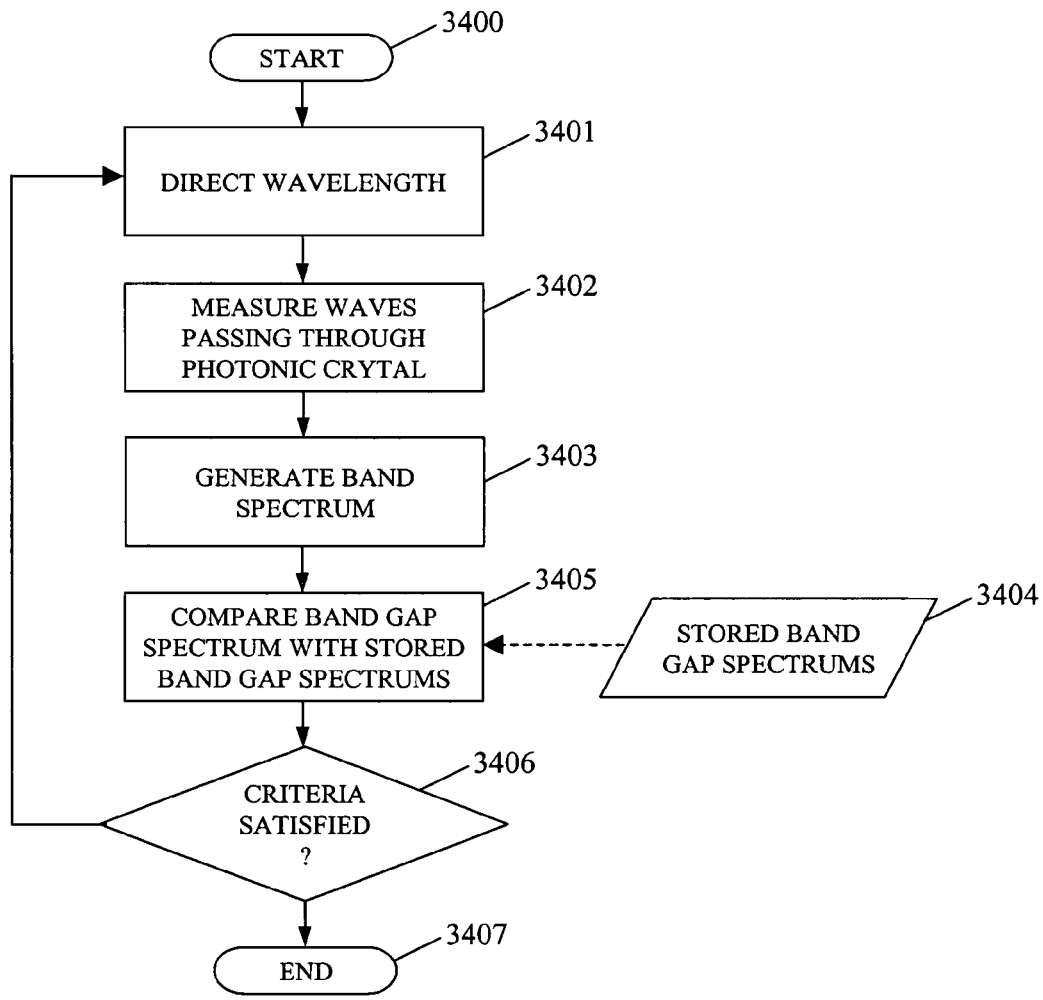
FIG. 34 illustrates a flowchart depicting at least exemplary one embodiment of a photonic crystal design device for determining the characteristics of a photonic crystal structure.

FIG. 34 illustrates a flowchart depicting at least one embodiment for evaluating whether a photonic crystal has a defect, and if so, how the defect can be characterized. As discussed above, a cavity in a photonic structure enables the development of peak frequencies within the band gap structure, where light of these frequencies could pass through the photonic crystal, whereas the equivalent non-cavity photonic crystal would not allow such passage. Thus, following a procedure (similar to the procedure of FIG. 34), a cavity can be detected if peak frequencies exist in the band gap.

Discussed above were methods to intentionally introduce these cavity structures in photonic crystals. However, in some cases, one may wish to have a photonic crystal free of defects. In a further exemplary embodiment, the speed of the algorithm discussed is used in conjunction with a light source and detector to determine if defects (cavities) exist with a photonic crystal. FIG. 34 illustrates a method in accordance with this embodiment described below.

Before the following steps are performed, a database 3404 of solution band gap spectrums can be simulated based upon various cavity sizes, numbers, and placements for a particular photonic crystal structure. The photonic crystal data can be used in software that solve Maxwell's Equations in the frequency domain (e.g. FDTD, TMM, FEM, and PWE) to obtain coarse data on the band gap spectrum. The coarse data can be used to derive detailed band gap spectrum solutions for various conditions of the cavity (e.g. location, size, number) with the results stored in the database 3404 as a function of the variables (e.g. as a function of size of cavity, location of cavity, the number of cavities).

Following start bubble 3400 of FIG. 34, a multi-wavelength electromagnetic wave is directed such that it is incident upon a photonic crystal sample to be tested (block 3401) (e.g., placing the sample photonic crystal to analyze on a holding element, one can direct multi-wavelength electromagnetic waves (e.g. light) into the sample). The wavelengths of the electromagnetic waves can be chosen to correspond to peak frequencies commonly observed if a cavity exists, based upon the stored solution of band gap spectrums 3404 for that particular photonic crystal composition, such as dimensions, material, and boundary values for field (e.g. electric and magnetic). Electromagnetic waves passing through the photonic crystal are then measured (block 3402). A device can be used to measure the electromagnetic waves that pass through the sample, where the detector is sensitive to possible peak wavelengths from the database (3404). Next, a band gap spectrum is generated from the measured electromagnetic waves (block 3403), using the above-described numerical simulation. The generated band gap spectrum is compared with stored band gap spectrums 3404, using evaluation criteria, which can be either user provided or set (block 3405). For example, the generated spectrum can be compared with the stored database 3404 to determine, based on evaluation criteria (e.g. number of matching peak frequencies), which stored photonic crystal cavity structure most closely resembles the measured spectrum. Next, a determination is made as to whether the stored band gap spectrum falls within the evaluation criteria (e.g., spacing of peak frequencies correspond to spacing of stored peak frequencies) (decision diamond 3406). If there is a match within the evaluation criteria in step 3405, a user can be notified that there appears to be a defect in the photonic crystal and the defect is seen to resemble the stored cavity structure that most closely matches the measured spectrum, and the process ends (end bubble 3407). If there are no matching peaks between the measured spectrum and the profiles in the database, and there are no other peaks in the band gap spectrum, the user is notified that the photonic structure appears to be defect free, or the process repeats until a satisfactory match within the evaluation criteria is obtained by returning to block 301. Thus, manufacturing processes that use photonic crystals can utilize the above method to analyze quality before placing the crystal in a manufactured device.

The above-described devices (e.g. gas detector devices, photonic crystal evaluation devices) can also be used with 3D photonic crystal structures. Conventional methods for predicting accurate spectral responses for 3D photonic crystal cavities are seen to be so inefficient as to render design of such devices impractical.

To fully utilize the properties of photonic crystal technology, the full three-dimensional (3D) optical control provided by 3D photonic crystal structures can be used in many applications. The objective of this embodiment as an addition to the above embodiments is to illustrate how the numerical simulation can be used in conjunction with other numerical methods such as TMM (transfer matrix method) to resolve some of the most complex structures, with improved speed and accuracy compared to the conventional methods.

One of most complex structures in electromagnetic designs is microcavities embedded in three-dimensional photonic crystals. First, these structures have complex sub-wavelength geometries, which make nearly all conventional simplifications of Maxwell's equations invalid. A full vectorial numerical solver with large simulation volume should to be used to model such structures. The heavy requirement on the numerical modeling programs typically limits access to these complex structures to cutting edge scientific research topics for a few scientists who have access to powerful computation hardware resources (e.g. large and high speed parallel computer clusters). Even with all of the state-of-the-art supercomputers, such simulations are still time consuming to the extent that designs can only be evaluated by very few iterations. Accordingly, such research tends to be a scientific research topic, not an engineering research topic.

One the other hand, these microcavities will support highly confined (in the full 3D space) optical mode(s). The highly confined the optical mode(s) can serve as the host where optical gain material can be added inside to realize high efficiency light emitting devices (e.g. lasers or light emitting diodes). In addition, the optical modes can be used as an enhanced optical sensor (as described in the gas detector devices embodiments), but with a much higher degree of freedom in integration in 3D space. With this and many other appearing merits in physical properties, the topic of microcavities in 3D photonic crystals is an attractive study area in both academic and industrial communities. The numerical simulation described above can be used with increased speed and accuracy.

The hosting 3D photonic crystal chosen for this embodiment is the so-called "woodpile" photonic crystal. The reasons for such a choice are: (a) the layer-by-layer configuration of such geometry is compatible with standard semiconductor fabrication technologies, compared with other 3D photonic crystal geometries; (b) such structures provide a well behaved and large full 3D photonic bandgap, which makes the device optical properties easier to analyze in the full photonic bandgap frequency range; and ©) the fact that the high dielectric index materials are physically connected in relatively large cross-sections makes it possible to realize electrical injections through such structures later.

Figure 35A:
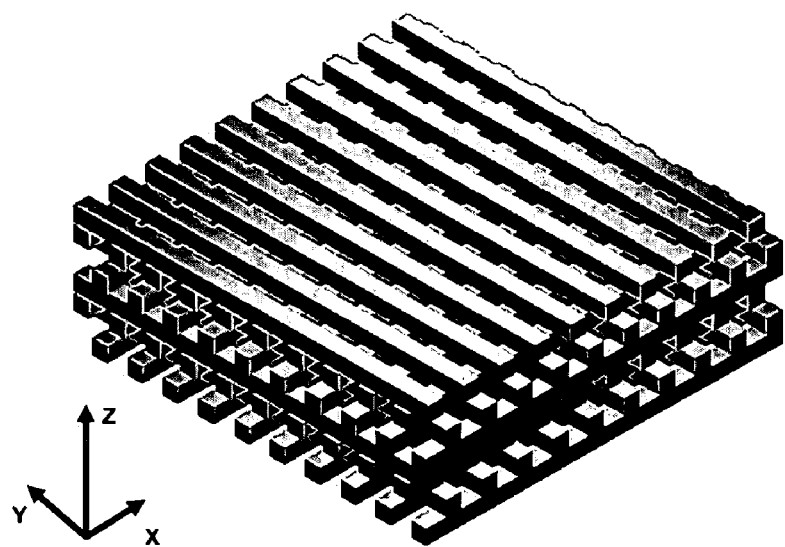
Figure 35B:
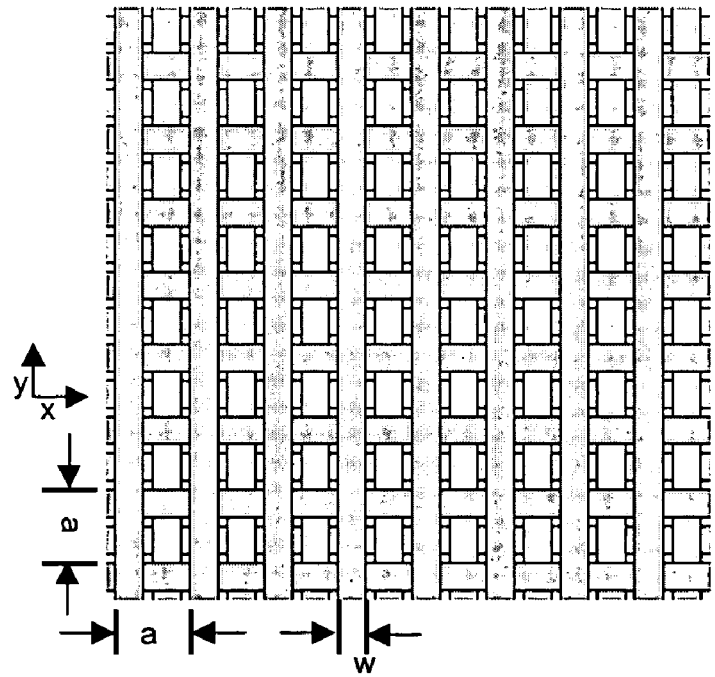
FIG. 35B illustrates a top-view of the 3-D crystal of FIG. 35A.

FIG. 35A illustrates an exemplary geometry of a woodpile 3D photonic crystal structure. It consists of alternating 1D array of rods piled up along the z-orientation. The first layer and the second layer are different by a 90-degree-rotation. The first layer and the third layer are different by an "a/2" shift along the y-orientation, where "a" is the pitch of the rods in each layer as labeled in FIG. 35B, which is a top-view (along the z-orientation) of the FIG. 35A. The second layer and the fourth layer are different by an "a/2" shift along the x-orientation. The whole structure repeats itself every four layers.

Figure 35C:
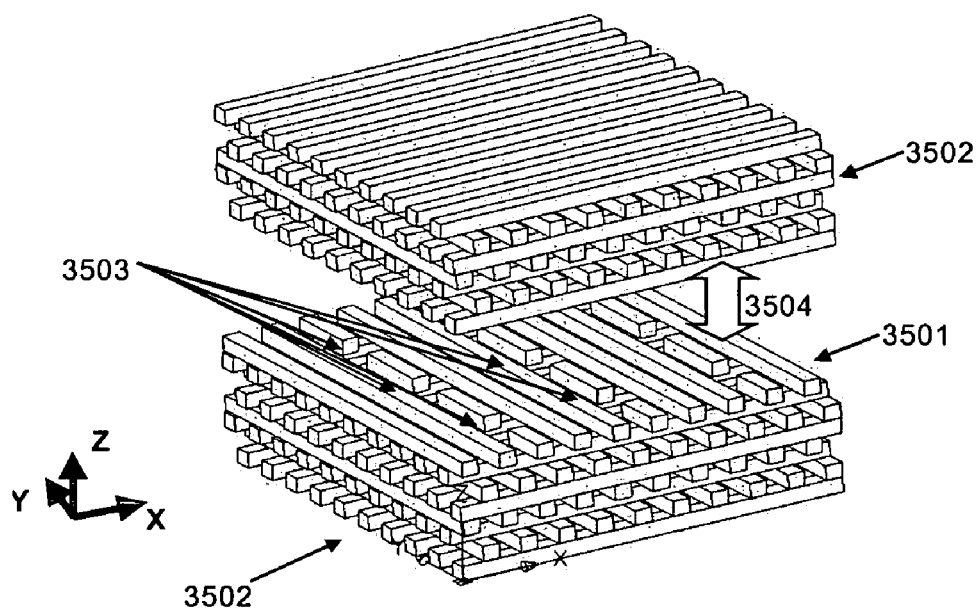
FIG. 35C illustrates an example of a 3-D photonic crystal cavity.

Microcavities can be embedded into the 3D woodpile structure. FIG. 35C is an illustration showing such embedded structure. A layer with cavities 3501 is sandwiched between two cladding woodpile photonic crystal blocks 3502. To make the embedded cavities visible in this 2D graph (i.e. FIG. 35C), the upper and lower cladding blocks 3502 are pulled apart (3504) to show the center layer 3501. The real structure has the upper block 3502, the cavity layer 3501, and the lower blocks 3502 in contact with each other.

In the example, the array of cavities 3503 are formed by breaking gaps in the length of "a" for every "3 a×3 a" area. These cavities can then trap localized modes with their resonant frequency within the photonic bandgap of the hosting woodpile photonic crystal.

In this exemplary embodiment, the lattice constant is a=10.7 mm (or normalized as a=1.0), the thickness of each rod is 3.2 mm (or normalized as 3.2/10.7=0.299), the width of each rod is 3.2 mm (or normalized as 3.2/10.7=0.299) and the refractive index of each rod is 3.015. A total of 22 layers of woodpile were used. In other exemplary embodiments, various dimensions can be used in accordance with design considerations.

An incident probing light along the z-orientation (see FIG. 35C) can be used to obtain the information of the localized resonant mode(s) in the cavity. This is similar to the resonant transmission phenomenon as described in the previous embodiments. The differences are now that the problem is in 3D and free space planewave incident replaces the waveguide incident waves.

Figure 36:
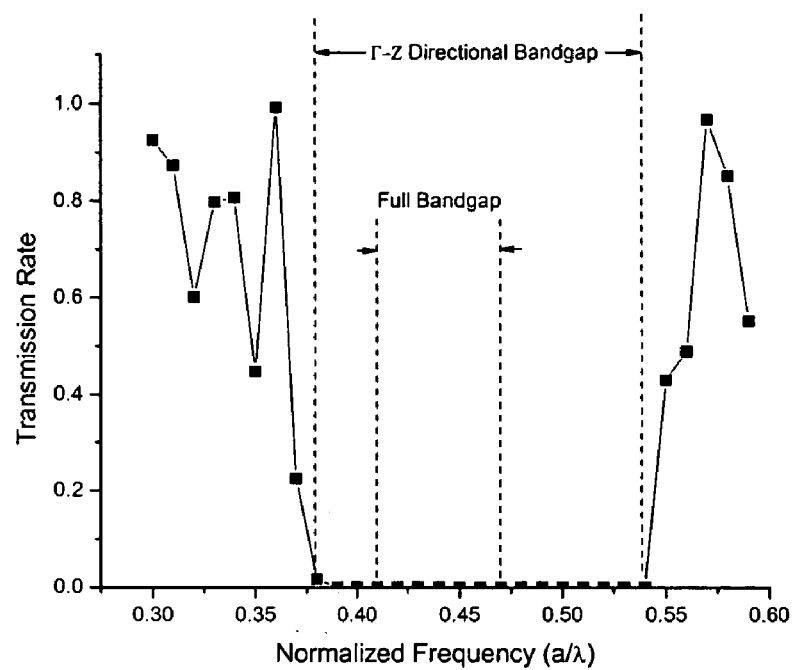
FIG. 36 illustrates a transmission spectrum (with a band-gap) of the photonic crystal structure of FIGS. 35A and 35B.

When the cavities 3503 do not exist, a perfect 3D woodpile photonic crystal is presented. The transmission along the z-orientation through the block is shown in FIG. 36. The strongly attenuated range of frequency (i.e. normalized frequency a/λ 0.38~0.54) corresponds to the directional bandgap of the photonic crystal itself along the z-orientation. This transmission spectrum was obtained by planewave-based transfer matrix method (TMM). Unlike the FDTD method used the gas detector embodiments, TMM is a frequency domain simulation method. Namely, TMM directly generates the transmission rate at each frequency one by one, without the need for time evolution or time-frequency Fourier transformation. Since TMM is such a direction frequency calculation, the transmission amplitude it generates for each frequency point is significantly more accurate that those generated by the DFT (discrete Fourier transformed) time domain signal from FDTD.

However, TMM needs to calculate each frequency point independently one-by-one. Therefore, it is more evident that the requirement of high spectral resolution would directly require more TMM execution time. For instance, to search the frequency range [0.41, 0.47], (i.e. approximately the full bandgap range as labeled in FIG. 36) for all possible sharp resonances, which may be narrower than ~5×10$^{-5}$ (i.e. quality factor ~10,000), the TMM routine would run for at least 2×10$^4$ iterations to first comb through the full range [0.41, 0.47] without missing any resonant peak with quality factor less than 10,000. This can be an extremely time consuming calculation. Moreover, when the cavity structure becomes more complex, each frequency point could cost a couple of hours of computation time. A total of several tens of thousands hours calculation time then make using such calculations to aid in designing devices, practically impossible.

On the other hand, using the rational function interpolation and Lorentzian regression technique described above on the current TMM data, a high resolution spectra can be obtained with only a few or dozens of frequency points.

Figure 37:
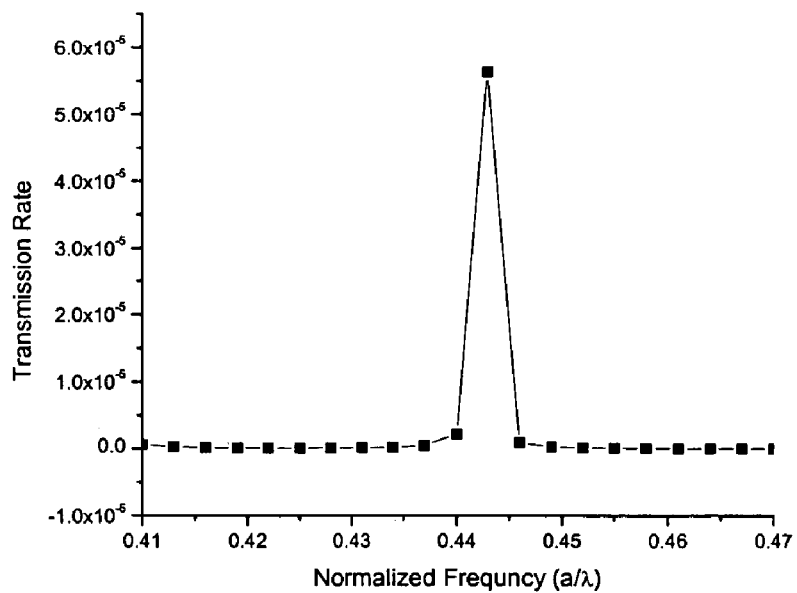
FIG. 37 illustrates a linear-scale graph of a transmission spectrum generated by performing TMM on an original set of points across the range of the band gap of FIG. 36.

FIG. 37 plots the transmission amplitude of 21 frequencies, evenly spaced covering the full frequency range from 0.41 to 0.47. From it, it is difficult to determine whether the low amplitude peak (i.e. transmission rate less than 6×10$^{-5}$) is due to a low quality factor peak with low amplitude, or due to a high quality factor peak with high amplitude, with its peak frequency located somewhere between 0.44 and 0.425. Also, it can be difficult to determine whether there are more sharp peaks located between the sparsely scattered 21 sampled frequencies. Namely, the spectral resolution is nearly too coarse to draw any meaningful conclusion.

To generate a more accurate high resolution spectrum, the 21 scattered data points (shown in FIG. 37) are used as the input to the rational function interpolation routine. In less than 2 seconds, a high resolution spectrum shown as the solid line in FIG. 38 is generated.

Figure 38:
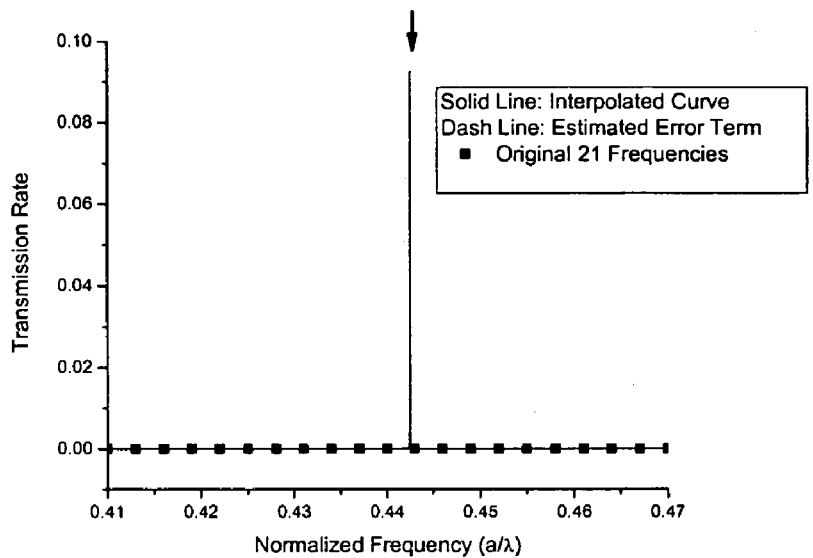
FIG. 38 illustrates the spectral response curve generated by performing rational function interpolation on the TMM frequency points of FIG. 36.
Figure 39:
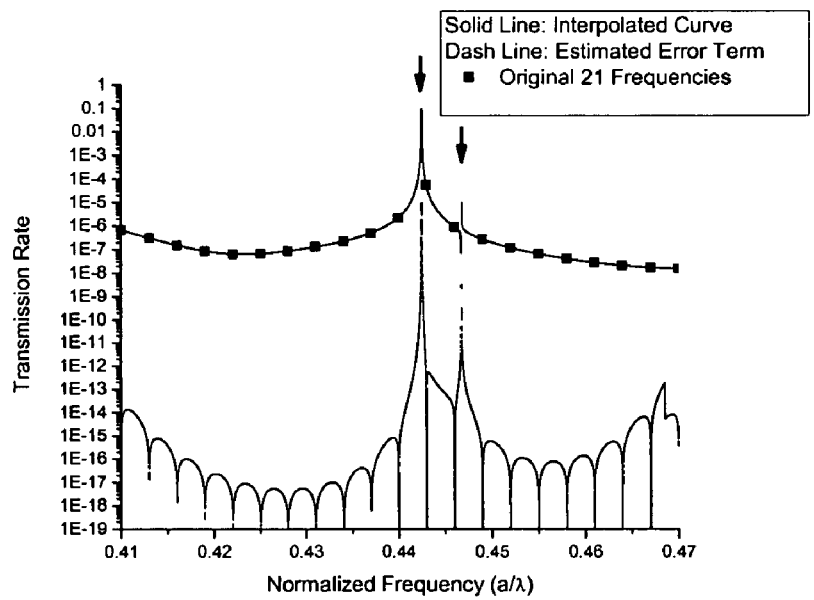
FIG. 39 illustrates the spectral response curve of FIG. 38 in semi-logarithmic scale.

From FIG. 38, a sharp and high amplitude (~9% transmission rate, as oppose to the $10^{-5}$ seen in FIG. 36) peak located near frequency 0.442 can be seen. To better see the details provided by such high resolution spectrum, FIG. 38 is plotted again in semi-logarithmic scale in FIG. 39. From FIG. 39, the estimated error term is seen to be more than 8 orders of magnitude smaller than the interpolated curve in most of the frequency regions. Even near the two sharp peaking frequencies, the error term is still consistently more than 3 orders of magnitude below the interpolated curve. This suggests that the interpolation result is reliable with only 21 input frequencies.

With such high resolution, two sharp resonant features located near 0.4425 and 0.4675 respectively can be seen. To observe each feature in greater details, FIGS. 40 and 41 provide the zoom-in views of the two sharp resonant features.

Figure 40:
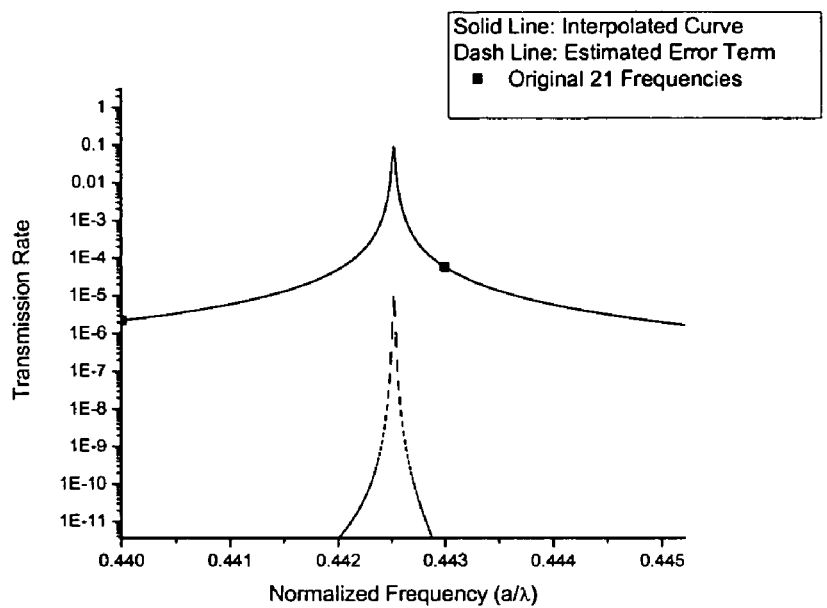
FIG. 40 illustrates a zoom-in view of a first peak of FIG. 39.
Figure 41:
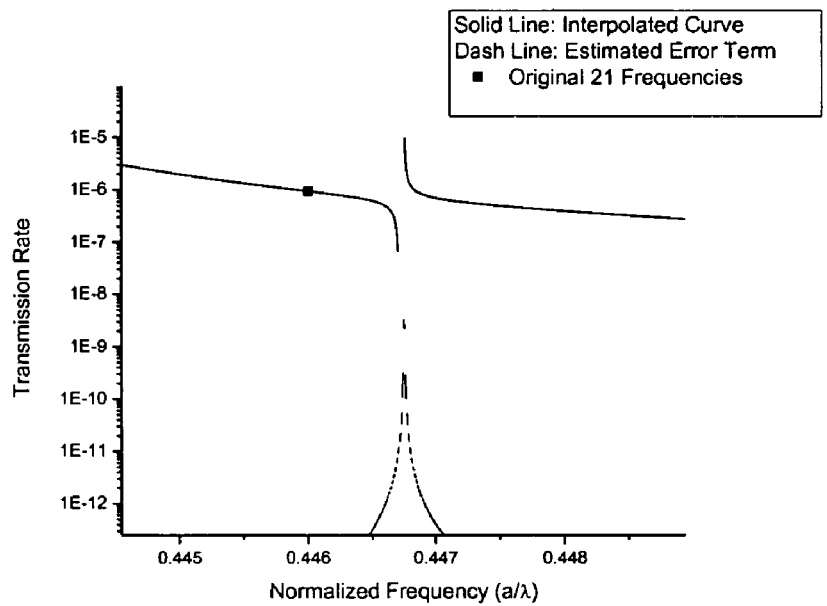
FIG. 41 illustrates a zoom-in view of a second peak of FIG. 39.
Figure 42:
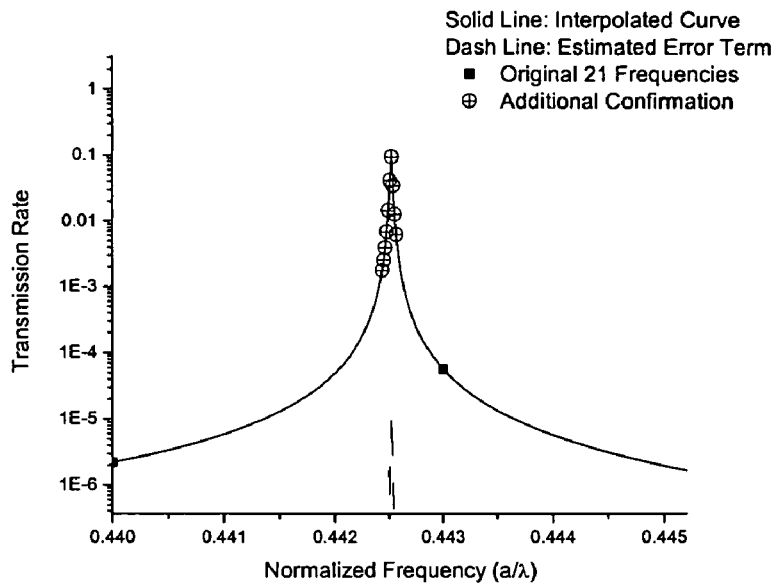
FIG. 42 illustrates the peak of FIG. 40 with additional TMM points superimposed thereon for verifying accuracy of the spectral response curve.
Figure 43:
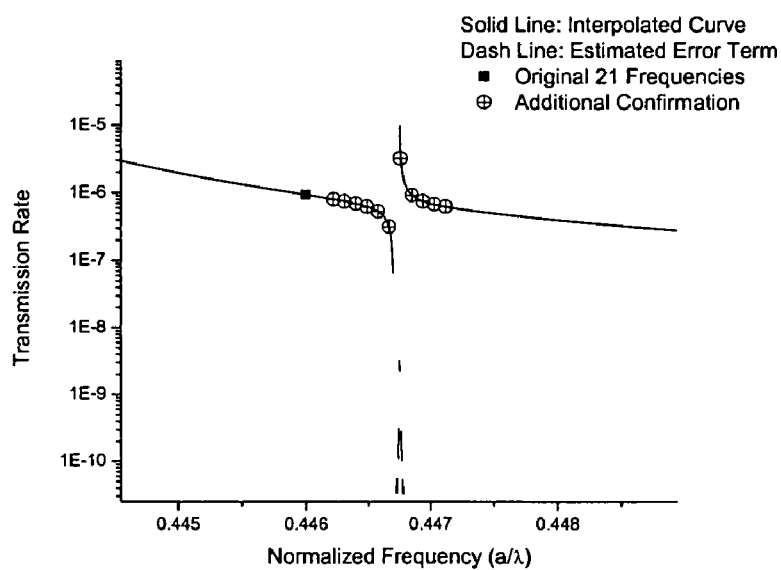
FIG. 43 illustrates the peak of FIG. 41 with additional TMM points superimposed thereon for verifying accuracy of the spectral response curve.

Although the low amplitude sharp feature shown in FIG. 40 is not a mode of physical interest, the accuracy of the rational interpolation method can be checked using both features. To demonstrate the accuracy of this method, additional frequency points were calculated near the sharp resonant features. The results of these additional data points are plotted on top of the interpolation results. FIG. 42 and FIG. 43 show the accuracy of the interpolation. The solid line in FIG. 42 and FIG. 43 are the same shown in FIG. 40 and FIG. 41. The scattered symbols show the additional frequencies being checked by TMM. The additional frequency points are seen to agree with the interpolation line.

Next, Lorentzian regression can be performed. The values of peak frequency, width, and height can be extracted automatically by performance of the Lorentzian regression routine, using the interpolated line as its input.

Figure 44:
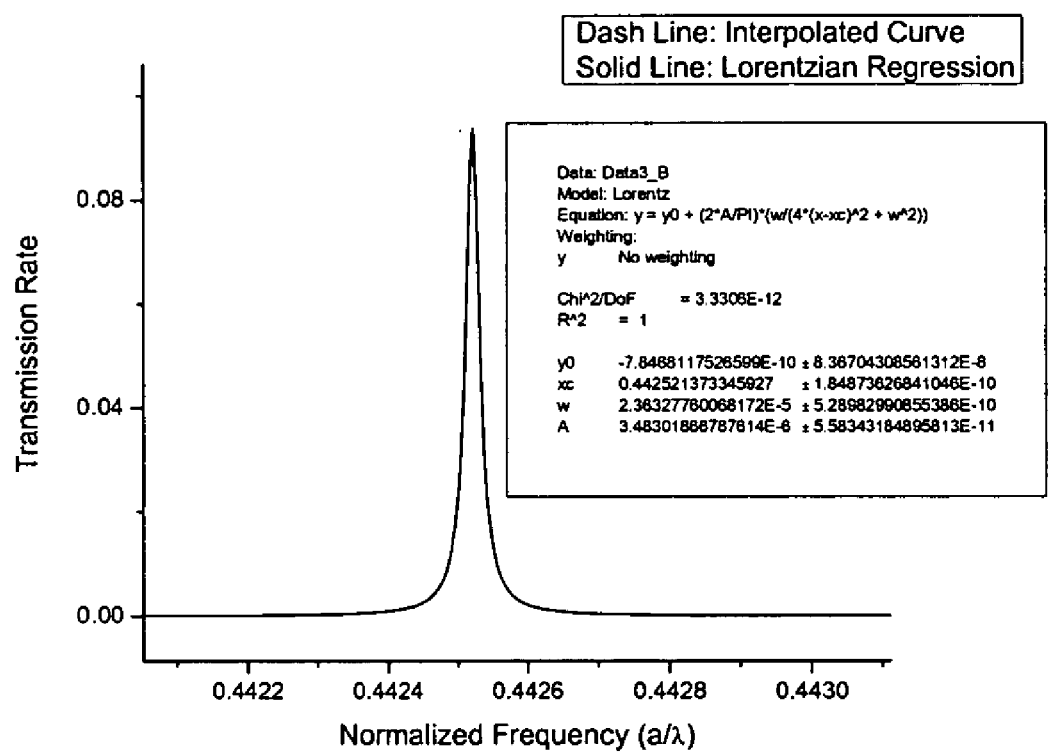
FIG. 44 illustrates the curve generated by performing Lorentzian regression on the peak of FIG. 40.

FIG. 44 shows the result of the Lorentzian regression. The dashed line for the interpolation curve is invisible in this plot, because it is overlapped by the Lorentzian regression curve (solid line). The results of this regression include: a peak frequency of $0.4425213733 \pm 1.8 \times 10^{-10}$, a peak width of $2.363277 \times 10^{-5} \pm 5.3 \times 10^{-10}$, and a peak height of 9.38256%. The narrow peak width corresponds to a quality factor of $1.87 \times 10^4$.

Up to this point, the discussion regarding the previous embodiments did not account for adjustment of a large estimated error term, and also did not account for two or more peaks overlapping at a common curve. As will be discussed, the above-described numerical simulation can generate efficient and accurate spectral response data for complex photonic crystal structures in which large estimated error terms exist (after a first performance of rational function interpolation), or overlapping peaks exist.

Figures 45, 46:
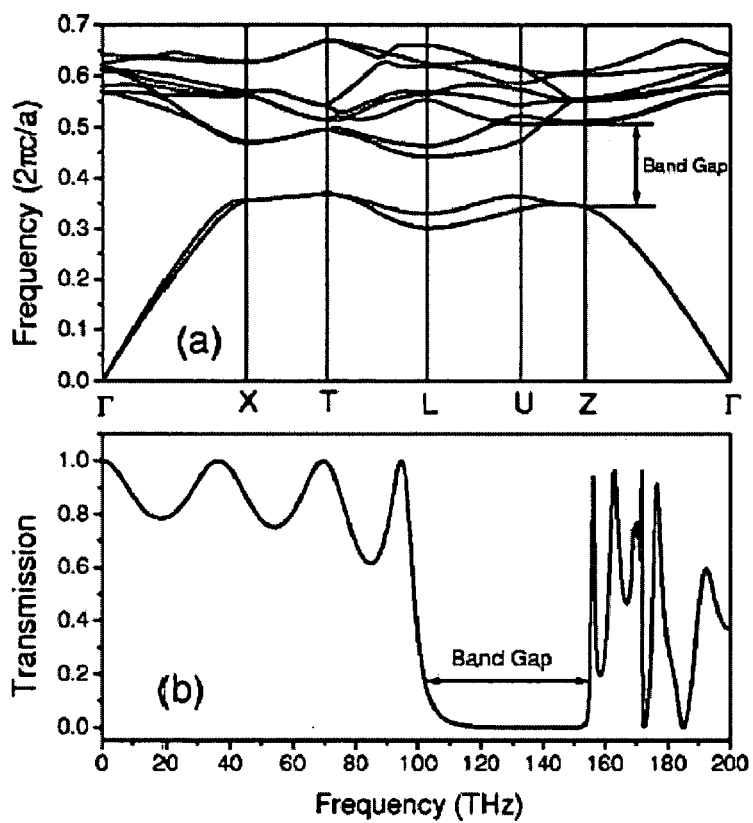
FIG. 45 illustrates plots of photonic band structures for a particular photonic crystal structure in accordance with at least one exemplary embodiment.
FIG. 46 illustrates the transmission spectrum of the photonic crystal structure of FIG. 45.

With reference to FIG. 45, plots are depicted of photonic band structures along some high-symmetry lines of a first Brillouin zone of an fct lattice, and corresponds to a particular 3D photonic crystal arrangement. The crystal is of a rod-to-rod spacing of 1 μm, a rod width and thickness of 0.25 and 0.3125 μm, respectively, and a refractive index of the rods n=3.4. FIG. 46 depicts a transmission spectrum of FIG. 45, showing the directional band gap on the Γ-Z direction. The wave is polarized so that the electric field is parallel to the rods in the first layer. This band gap structure was calculated by an ISU Journal Publication, namely Journal of Applied Physics 94(2), 811-21 (2003). Although the following calculations were not necessarily performed with the photonic crystal structure of FIGS. 45 and 46, the above-described numerical simulation can be used to efficiently and accurately predict the band spectrum of this structure.

Figure 47:
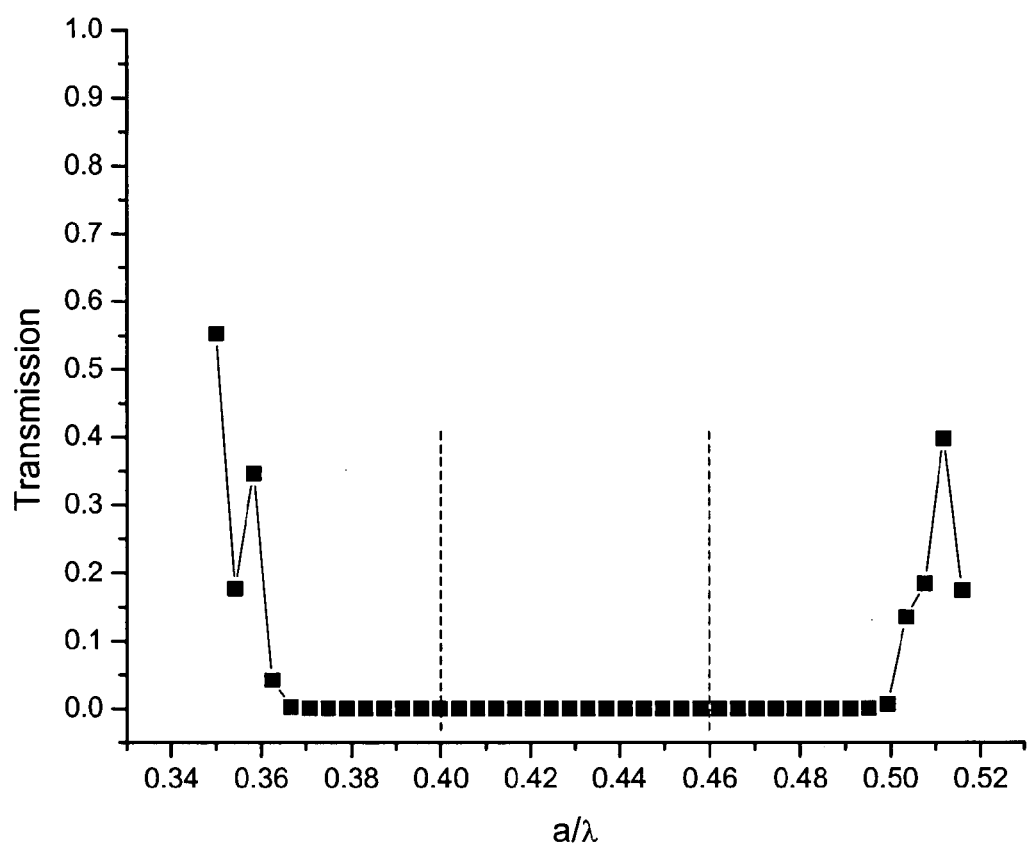
FIG. 47 illustrates the frequency range of the band gap within the transmission spectrum of FIG. 46.

FIG. 47 illustrates a frequency range of the band gap that was calculated to estimate a particularly complex band gap range. As can be seen, the full band gap is located at approximately the central ⅓ region of the directional band gap, and the normalized frequency (i.e. a/λ) range is within ~0.4 to ~0.46, which is delineated by two dashed vertical lines in FIG. 47.

Presuming that there is one resonant peak with a quality factor (Q) of 10,000 somewhere in the band gap, a frequency (wavelength) domain scanning of resolution better than $5.5 \times 10^{-5}$ μm would be required to detect this peak. At this resolution, at least 2,000 frequency points would need to be calculated. As noted above, TMM is a frequency domain method with a calculation time that increases linearly with the number of frequency points being calculated. If one frequency point requires 10 minutes of calculation time (which is a reasonable estimate), then 2,000 points would require over 330 hours of calculation time. However, exemplary embodiments do not require the calculation of 2,000 frequency points using TMM in order to resolve a resonant peak.

Figure 48:
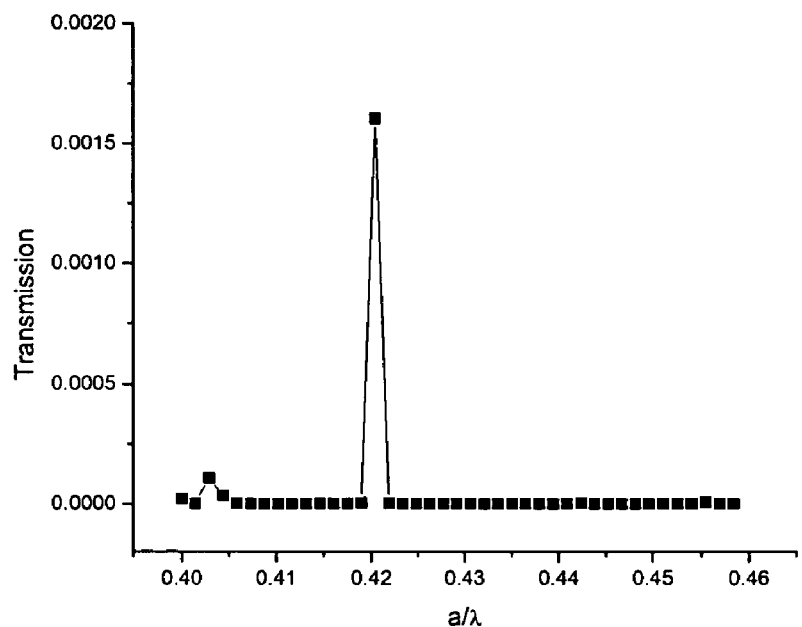
FIG. 48 illustrates a linear-scale graph of a transmission spectrum generated by performing TMM on an original set of points across the range of the band gap of FIG. 47.
Figure 49:
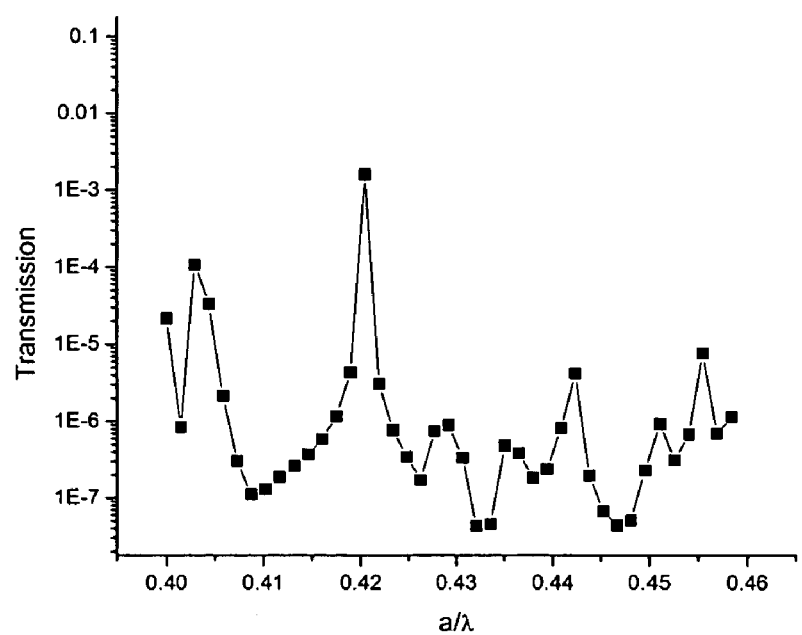
FIG. 49 illustrates a semi-logarithmic scale graph of FIG. 48.

Results of the transmission spectrum generated by performing TMM (block 302 of FIG. 3) are shown in FIGS. 48 and 49. FIG. 48 illustrates the transmission spectrum generated by performing TMM on the initial set of 41 points across the range of the band gap of FIG. 47. FIG. 49 is a semi-logarithmic scale graph of FIG. 48. As can be seen in these diagrams, there may be a decent peak near the normalized frequency 0.42. However, to be confident that no resonant peak(s) with a quality factor as high as $10^4$ are missed, and to be able to locate peak frequencies and widths with practical accuracy, a better spectral resolution is needed (e.g. 0.00004, or $4 \times 10^{-5}$). To obtain peak width accurately, even a higher resolution is needed (e.g. $1 \times 10^{-6}$). For example, with 41 points, the resolution is 0.0015 (i.e. $1.5 \times 10^{-3}$). Therefore, to obtain any reasonable accurate results using the traditional TMM approach, more simulations would need to be conducted. Although higher Q (say $10^6$) peaks might still be missed. In at least one exemplary embodiment, rational function interpolation can be performed to increase accuracy and efficiency of generating a spectral response based on N frequency points.

Figure 50:
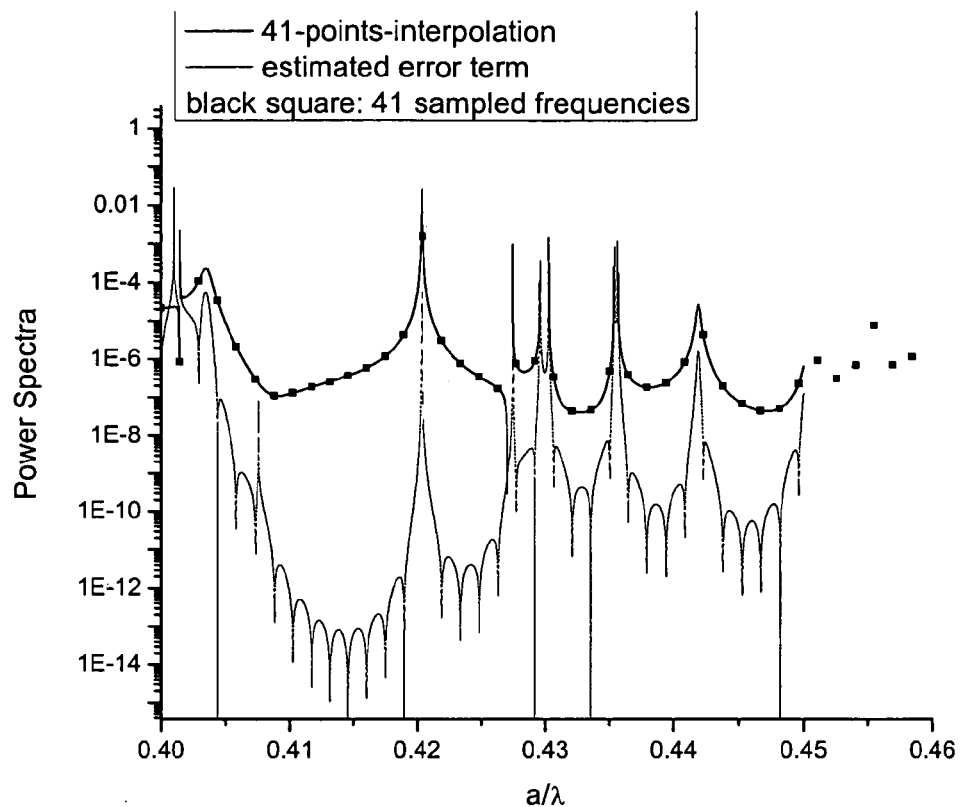
FIG. 50 illustrates the spectral response curve generated by performing rational function interpolation on the TMM frequency points of FIGS. 48 and 49.
Figure 51:
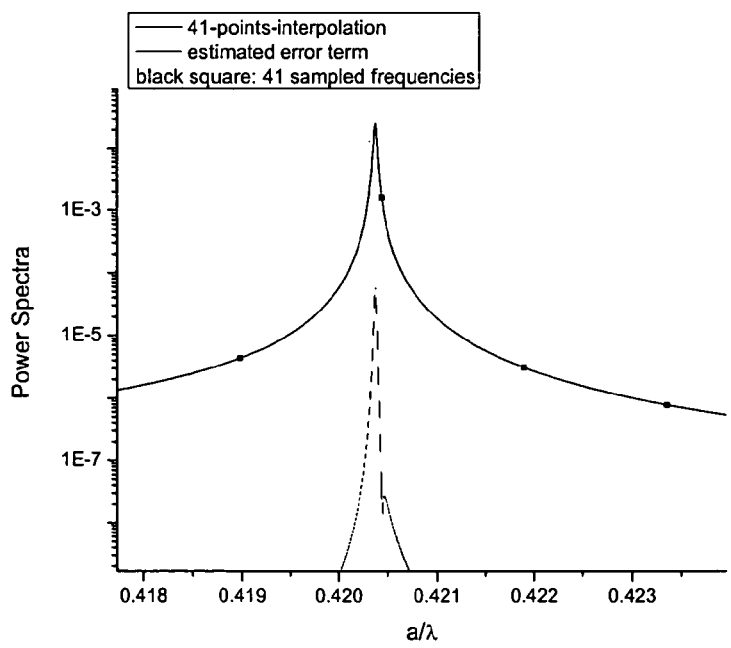
FIG. 51 illustrates an expanded view of a peak of FIG. 50.

Results of performing rational function interpolation are shown with reference to FIGS. 50 and 51. FIG. 50 illustrates the spectral response curve generated by performing rational function interpolation (e.g. using Bulirsch-Stoer algorithm) on the TMM frequency points of FIGS. 48 and 49. It can be seen in the full range that there is more than one peak, with some peaks being narrow (i.e. high Q). FIG. 51 illustrates an expanded view of one of the peaks of FIG. 50.

FIGS. 50 and 51 illustrate the result of using rational interpolation procedure, in accordance with at least one exemplary embodiment, to generate the predicted spectral details (solid line) and the error estimation terms (dashed line). In this example, 10,000 frequencies were predicted at resolution of $6 \times 10^{-6}$ in less than 2 seconds. If necessary, within a few seconds, resolution can be increased to as high as needed, say $1 \times 10^{-10}$.

It can be seen that the peak in FIG. 51 is already accurately resolved, because the error term is more than 2 orders of magnitudes smaller than the interpolated line. However, there are some complications in the frequency range of 0.425~0.438 of FIG. 50, where the error term exceeds the interpolated line. Accordingly, the complexity of the photonic crystal cavity was most likely underestimated. In other words, although it was estimated that 10 or fewer resonant features were present in the photonic crystal cavity, more than 10 resonant features might actually be present.

With reference to FIG. 50, it can be seen that additional resonant modes are likely located outside the full bandgap range, but within the directional bandgap range. This corresponds to the first category of underestimation discussed with reference to FIG. 3 above (i.e. extra resonant peaks with relatively high amplitudes and low quality factors existing outside the frequency range of the photonic crystal bandgap). Although these additional resonant modes lie outside the full bandgap range, the additional resonant modes may still have significant envelope functions across the full bandgap range of 0.4~0.46.

Figure 52:
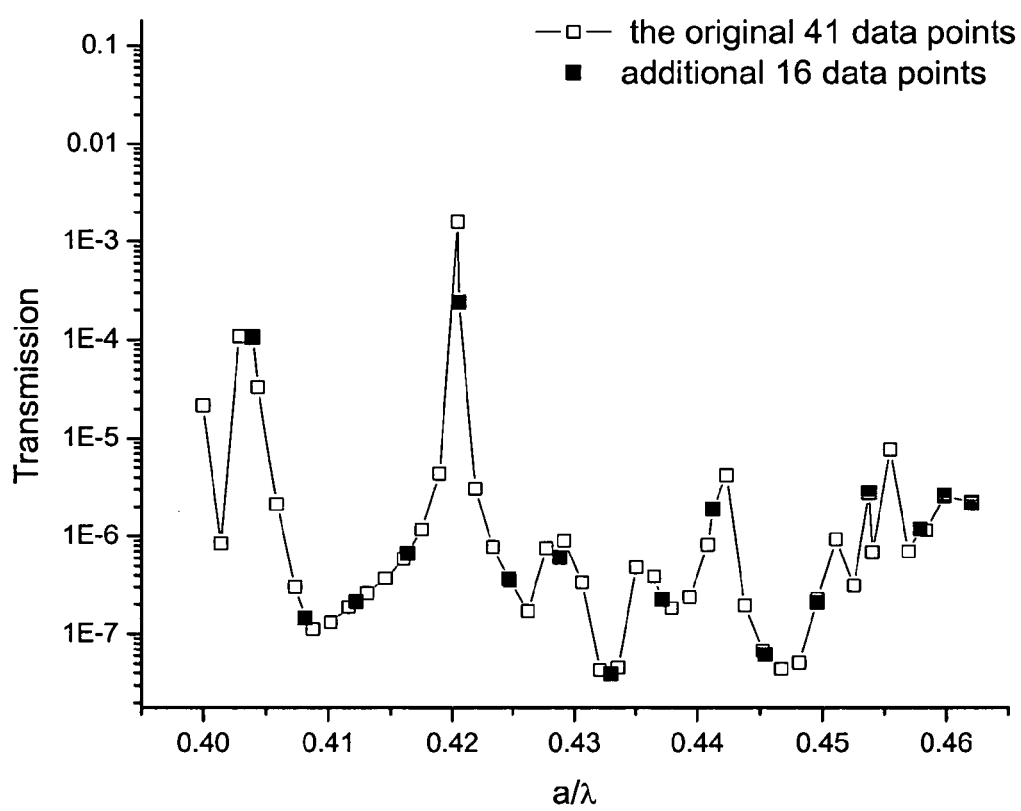
FIG. 52 illustrates a semi-logarithmic scale graph that illustrates the transmission spectrum generated by performing TMM on the original set of points of FIG. 48 and additional points.

Results of calculations based on the original N points and additional $N_1$ points (block 310 of FIG. 3) are shown with reference to FIG. 52. To improve the quality throughout the full bandgap range, 16 additional frequencies (solid squares) were calculated and added to the original 41 frequencies (open squares). FIG. 52 is a semi-logarithmic scale graph that illustrates the transmission spectrum generated by performing TMM on the original set of points (N=41) of FIG. 47 and the additional points ($N_1$=16).

Figure 53:
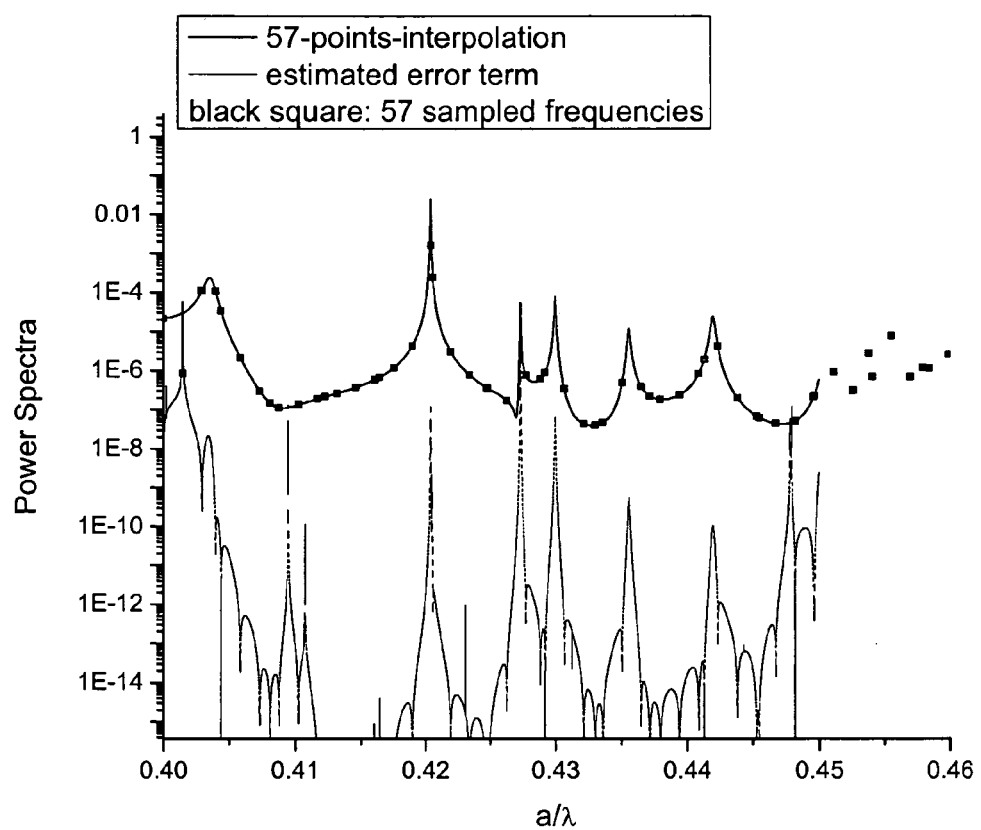
FIG. 53 illustrates the spectral response curve generated by performing rational function interpolation on the TMM frequency points of FIG. 52.

Results of performing rational function interpolation again (block 306 of FIG. 3) are shown with reference to FIG. 53. FIG. 53 illustrates the spectral response curve generated by performing rational function interpolation on the TMM frequency points of FIG. 52. It can be seen that after the addition of the $N_1$ frequency points, the estimated error term is now constantly lower than the interpolated power spectrum itself.

To confirm the accuracy and efficiency of the updated spectral response, although time consuming, hundreds of extra frequency points near the resonant peaks were calculated by TMM and compared to the spectral response of FIG. 53. The performance of the additional computations resulted in hundreds of hours of extra calculation time, and normally would not be performed as part of the numerical simulation of the present invention.

Figure 54:
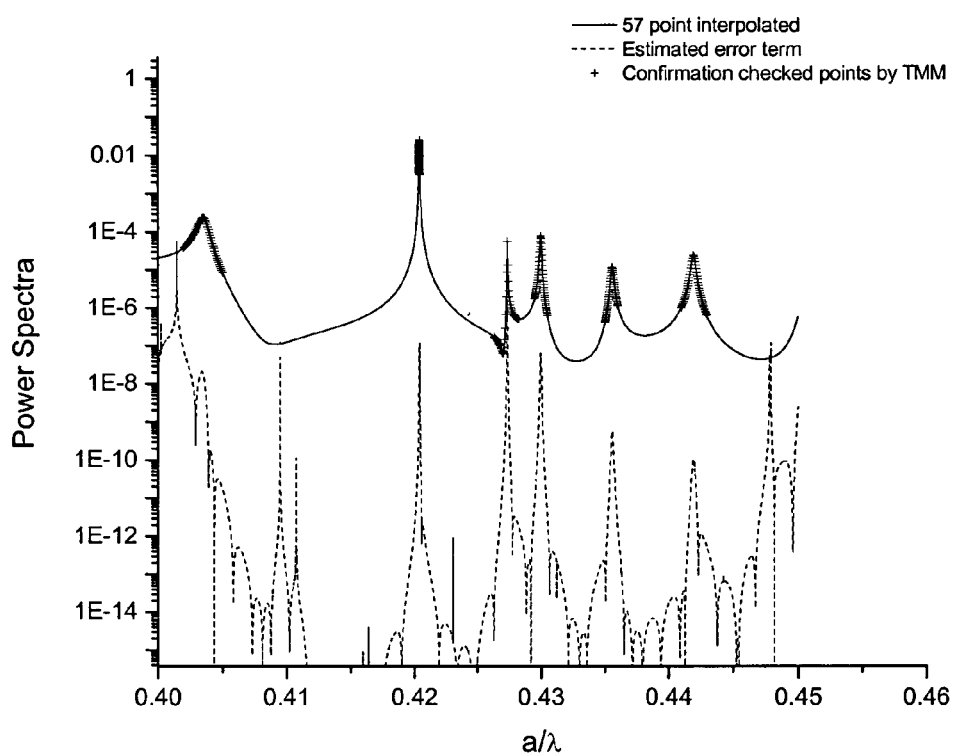
FIG. 54 illustrates the spectral response curve of FIG. 53 with additional TMM points superimposed thereon for verifying accuracy of the spectral response curve.
Figure 55:
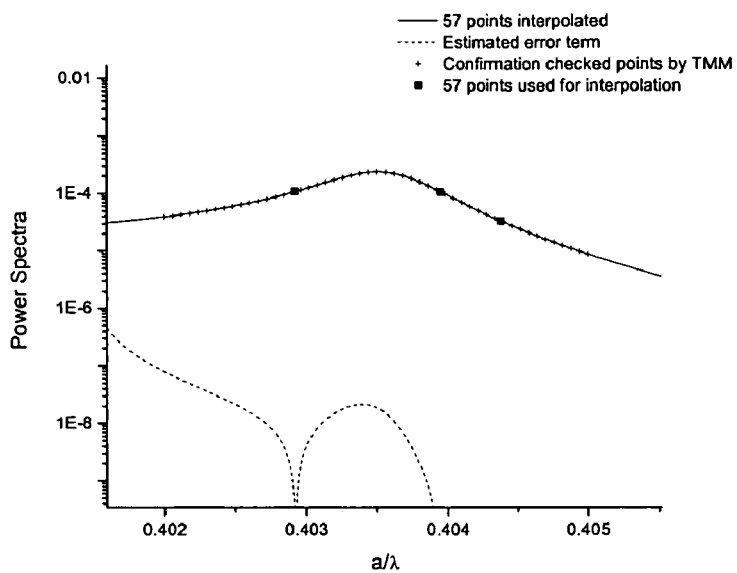
FIG. 55 illustrates an expanded view of a peak of FIG. 54.
Figure 56:
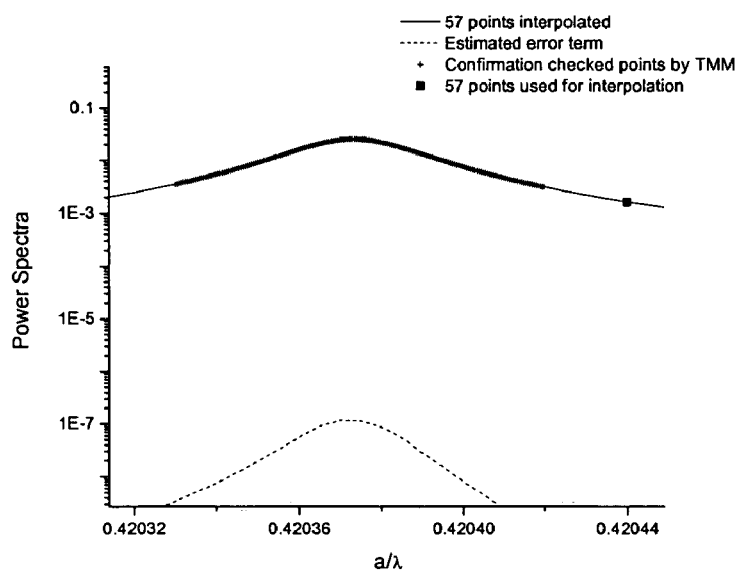
FIG. 56 illustrates an expanded view of another peak of FIG. 54.

Results of the performance of additional TMM confirming calculations are shown with reference to FIGS. 54 to 58. FIG. 54 depicts the additional TMM measurements (scattered crosses). FIGS. 55 to 58 are expanded views near different peaks of the spectral response curve. It can be seen that the updated spectral response of FIG. 53 matches closely with the additional TMM computations of FIGS. 54 to 58.

Figure 57:
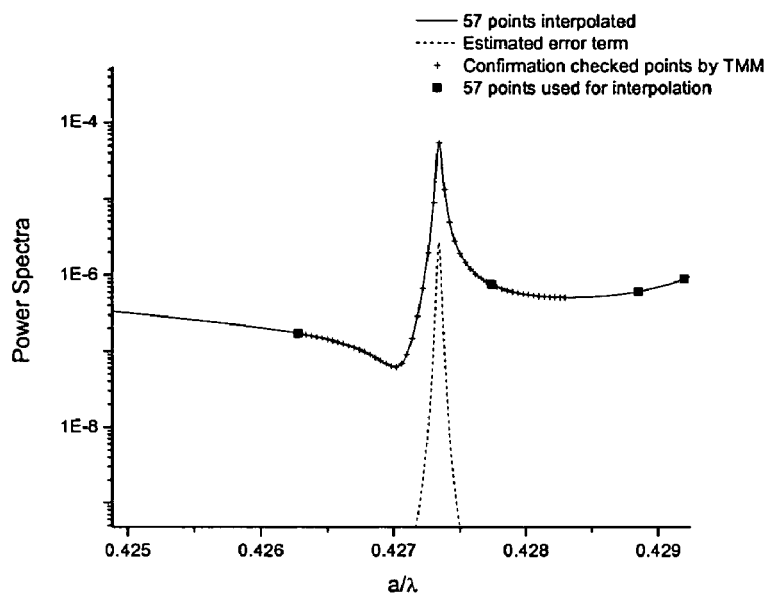
FIG. 57 illustrates an expanded view of yet another peak of FIG. 54.
Figure 58:
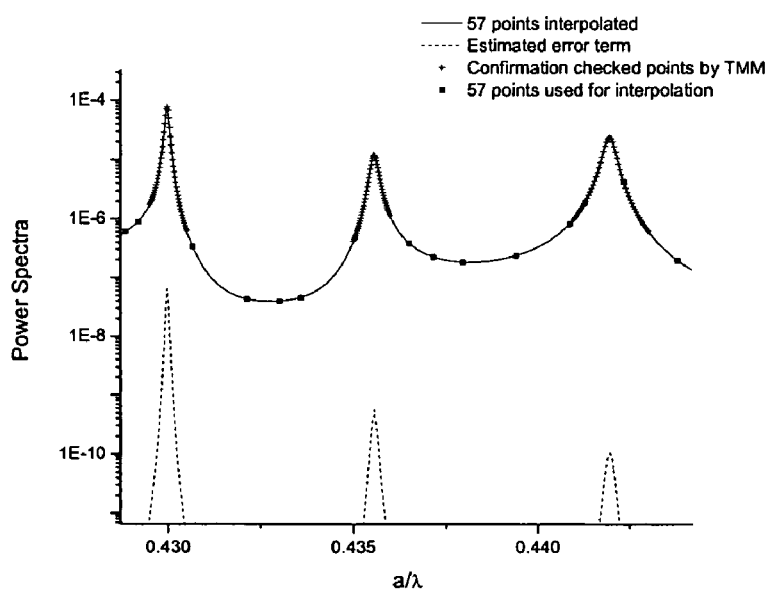
FIG. 58 illustrates an expanded view of yet another peak of FIG. 54.

With particular reference to FIG. 57, it was observed that the ideal individual resonant transmission peak fits a symmetrical Lorentzian. The asymmetric feature in narrow bandwidth (i.e. small frequency range) is due to a non-localized state.

Figure 59:
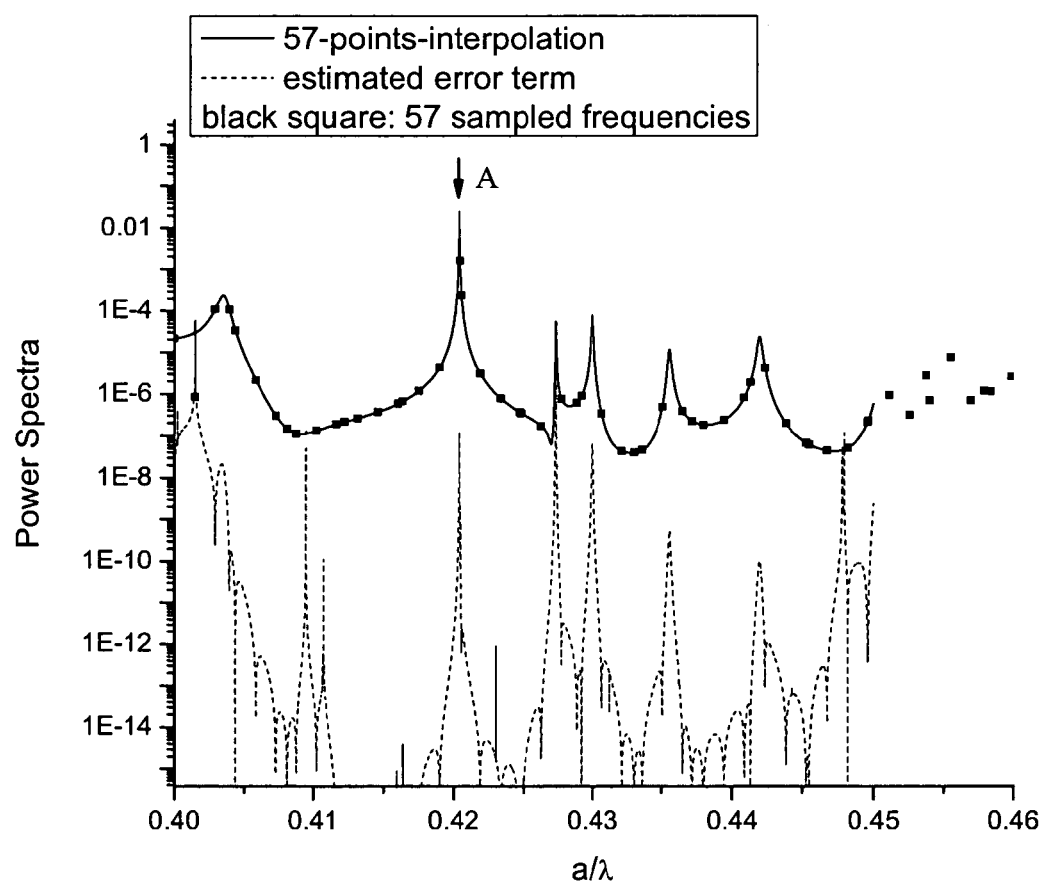
FIG. 59 illustrates the selection of a peak of FIG. 54 for which additional numerical simulation will be performed.

FIG. 59 illustrates the selection A of one of the resonant peaks (block 311 of FIG. 3). Additional numerical simulation is then performed at the vicinity of the selected peak (block 312). In at least one exemplary embodiment, Lorentzian regression is performed.

Figure 60:
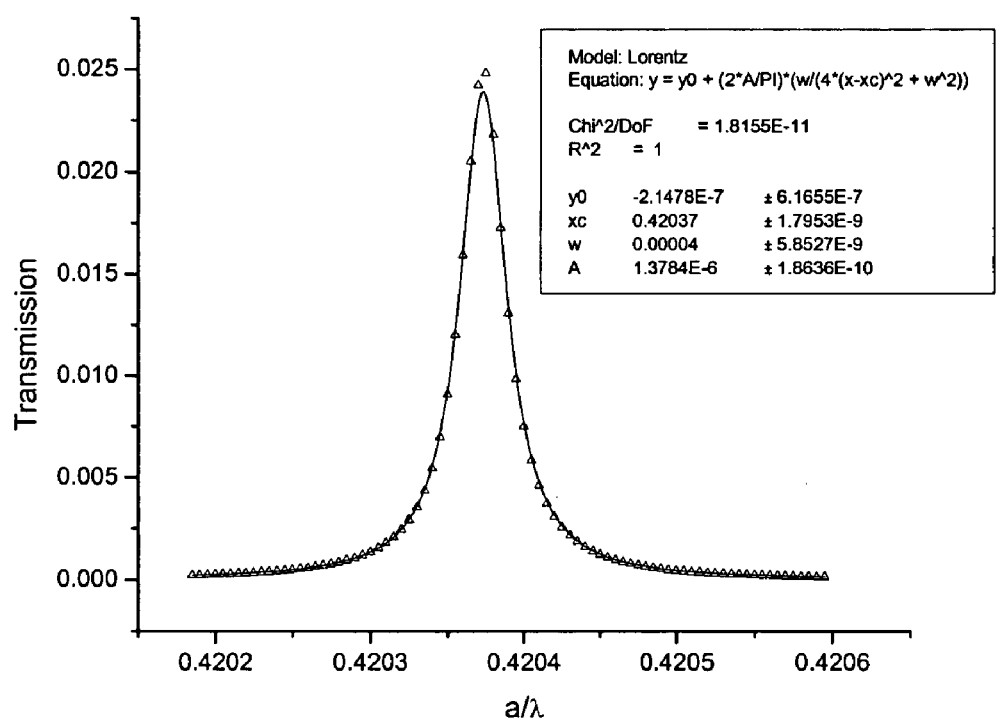
FIG. 60 illustrates the curve generated by performing Lorentzian regression on the selected peak of FIG. 59.
Figure 61:
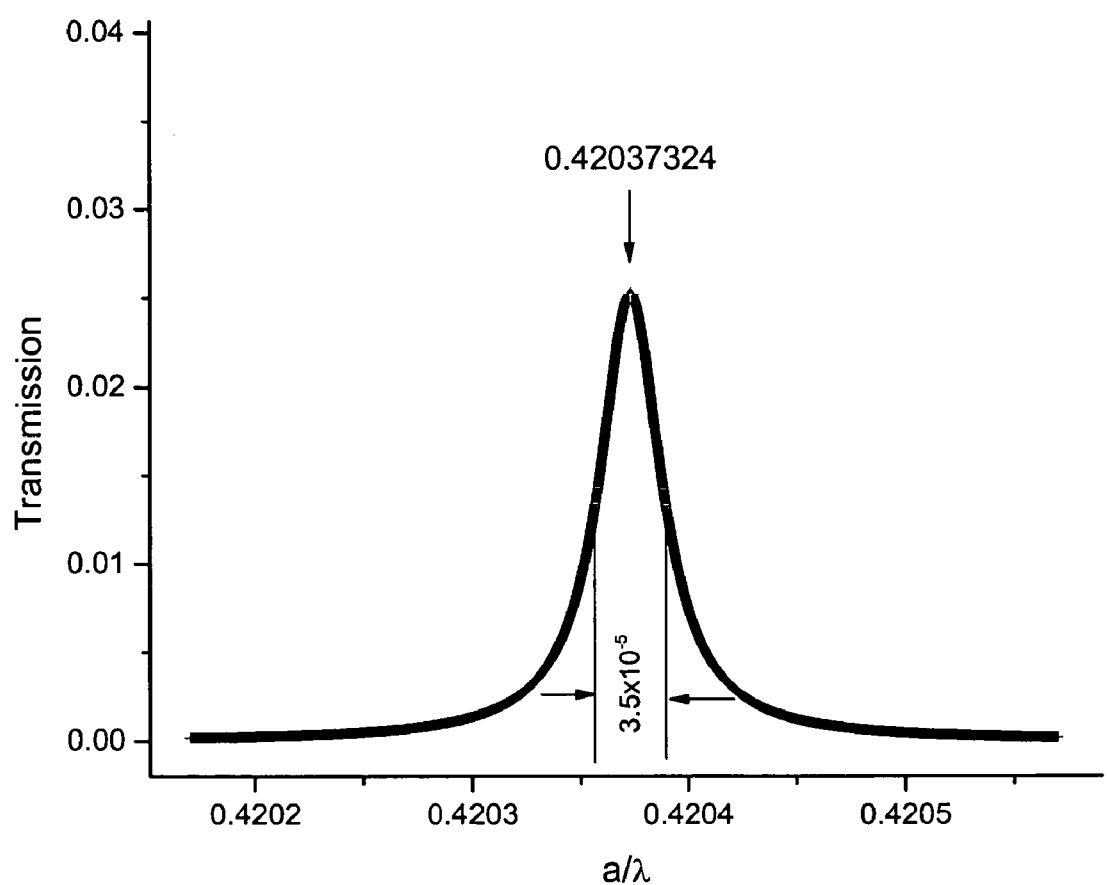
FIG. 61 illustrates the curve generated by performing interpolation on the selected peak of FIG. 59.
Figure 62:
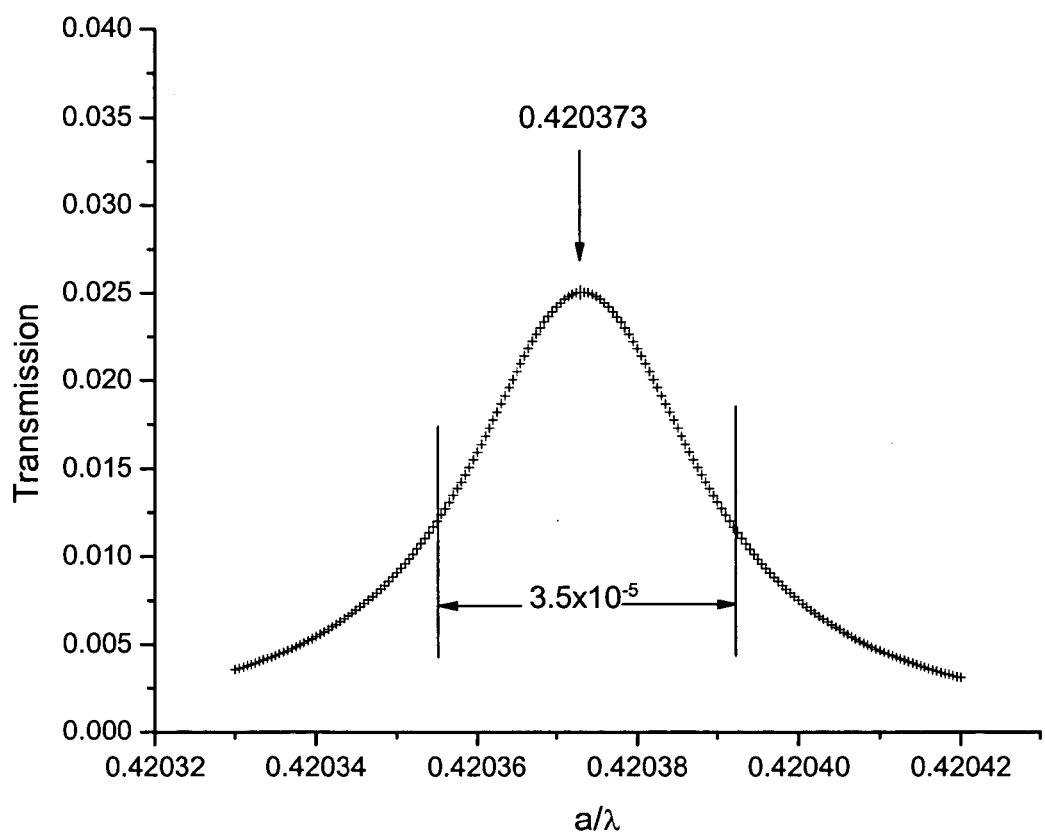
FIG. 62 illustrates the curve generated by performing TMM on the selected peak of FIG. 59.

Results for performing additional numerical simulation are shown with reference to FIGS. 60 to 62. FIG. 60 depicts the performance of Lorentzian regression at the selected peak A. It can be seen that the parameter information is obtained, namely $\omega_0$, width and Q. The computation time was only a couple of seconds.

Although, in the examples of exemplary embodiments discussed, Lorentzian regression is used, other algorithms may be used for the additional numerical simulation of block 312 of FIG. 3. For example, FIG. 61 corresponds to an increased resolution of the interpolated spectra near the peaks using rational interpolation, which required a couple of seconds of computation time. The increased resolution includes parameter information. FIG. 62 corresponds to an increased resolution of the interpolated spectra near the resonant peaks by performing TMM, which requires several tens of hours of computation time. This increased resolution also includes parameter information.

Figure 63:
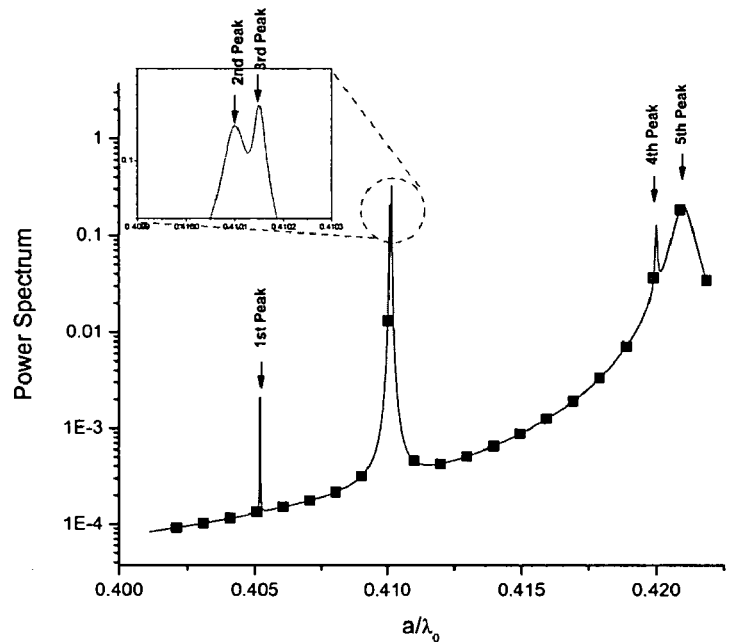
FIG. 63 illustrates the resolution of multiple resonant peaks overlapping on a common curve.
Figure 64:
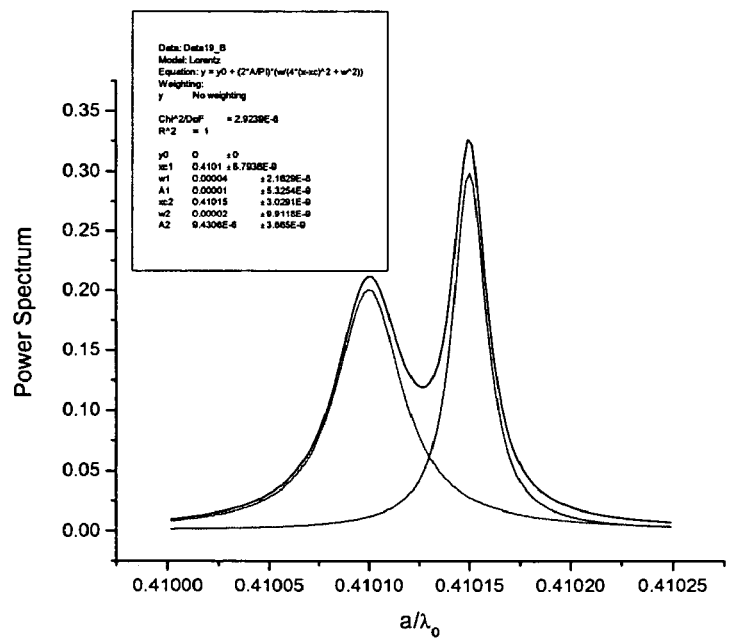
FIG. 64 illustrates a curve generated by performing Lorentzian regression on the common curve of FIG. 63.

An example of multiple peaks overlapping at the same curve envelope is shown in FIGS. 63 and 64. It should be noted that these figures do not necessarily correspond with the data measurements of the previous figures. Rather, FIGS. 63 and 64 illustrate the identification and characterization of peaks within a spectral response which has overlapping peaks.

FIG. 63 depicts assumed frequency sampling points (square symbols) based on TMM, along with an interpolated spectrum (solid line) based on rational function interpolation. The inset of FIG. 63 depicts a zoom-in view showing that two peaks overlap within the same curve. The zoom-in view is also depicted in linear scale as the single line curve in FIG. 64. However, it can be difficult to determine the exact parameter information for each of the peaks.

To determine more precise parameter information, a two-peak Lorentzian regression routine can be performed. Since a large number of data points can be determined by rational function interpolation, these data points can be used as the input data of the two-peak Lorentzian regression routine. The decomposed two peaks are shown as two separate curves in FIG. 64. Since the peaks are more clearly separated, parameter information, including the frequency and amplitude for each of these peaks, can be determined, as shown in the inset table of FIG. 64.

The exemplary embodiments discussed have described the tuning of a sensor device through the adjustment of the physical position of one pillar. It should be noted that exemplary embodiments are not limited to the pillar method of tuning and can use other methods of tuning. For example, the refractive index instead of the physical position of the pillar material may be tuned by using nonlinear material subjected to adjustable external electric field (or magnetic field) as described above with respect to the Pockels and Kerr effect.

Moreover, the adjustment does not have to be limited to the local physical properties near a cavity. Adjustment covering an extended area can also be used to tuning the optical performance of a device. For example, the bulk photonic crystal area can have its distributed refractive index be tuning through applying external electric field across multiple lattice constant range, or infiltrating nonlinear liquid (such as liquid crystals) in to the bulk photonic crystal area.

Additionally exemplary embodiments are not limited to gas sensors. The methods, processes, and devices of exemplary embodiments can be used in other sensors, lasers, enhanced photo diodes, other devices that can use tunable photonic crystals as known by one of ordinary skill in the relevant art, and equivalents.

For example, by utilizing optical gain material inside a cavity similar to exemplary embodiments described so-far, we can form tunable lasers. Moreover, the devices do not have to use localized photonic crystal defect modes. DFB (distributed feed back) photonic crystal lasers can be formed by bulk photonic crystals without defect, which function at the band edge modes of the bulk photonic crystal itself. They can also be tuned by adjusting the distributed physical properties of the device, such as the refractive index, lattice constants, as described above.

Additional exemplary embodiments include the fabrication of photonic crystals. At least one exemplary embodiment includes: preliminary design simulation; developing or mapping out the tuning curves caused by multiple physical parameters, which can include intentional tuning and unintentional fabrication related variations; and choosing the optimized combinations of parameter values to maximize fabrication margin, and/or to reaching tuning targets. Further exemplary embodiments can additionally test whether the resulted optical characteristics are indeed optimized by the design, or whether additional parameters may be identified as significant but omitted in the previous design. For example testing can determine whether the difference between the actual tuning property of the photonic crystal prototype is within a variation value of the target tuning property. These additional parameters can be used to develop a new design, which can then be simulated and the steps of above repeated to check optimization of the new design.

If the prototype testing is consistent with the previous design then mass production can be facilitated. If the prototype testing suggesting addition significant physical parameter(s), then addition mapping of the tuning curves for newly discovered physical parameter(s) can be performed and a new optimized structure can be chosen as discussed above.

Determining new parameters for the prototype photonic crystal can be selected by several methods in accordance with exemplary embodiments, for example the new parameters can be chosen by one of the following: by selecting the new parameter values to be at least one parameter value associated with difficult to control fabrication related parameters which fall within the regions where the tuning curves are flat; by selecting the new parameter values to be at least one parameter value associated with controllable fabrication related parameters which fall within the region where the tuning curves are relatively steep; by selecting the new parameter values to be at least one parameter value that fall within the region where the tuning curves are relatively steep while providing a tuning frequency within a predetermined variation value of a target tuning frequency; and by selecting the new parameter values to be at least one parameter value that fall within the region where the tuning curves are relatively flat while providing a tuning frequency with a predetermined tuning frequency error.

The tuning curves can be mapped and/or developed for many other potential parameters (or tuning mechanisms), for example the locations of four nearest posts surrounding a cavity, or the roughness/perfection of the chosen post or posts near and/or far from the cavity. The consequence of each of those individual variables (either by intentional tuning or by unintentional fabrication errors/margins) can be mapped out by using the simulation methods and equivalents as discussed herein.

Several methods and criteria for optimization can be used in exemplary embodiments, for example after a map of multiple curves is developed (e.g., with different tuning/fabrication-variation parameters as FIG. 23), then one can choose one/several to optimize the design for fabrication. The criteria of choosing optimized designs can vary in accordance with exemplary embodiments but can include: determining whether the parameter values of those uncontrollable (or hard-to-control) fabrication related parameters can fall within the regions where the tuning curves are flat (i.e. low slope); and determining whether the parameter value(s) of those controllable (or easy-to-control) fabrication related parameters can fall the region where the tuning curves are relatively steep; and/or determining whether the parameter value(s) of the mechanism one plans to tune dynamically can be chosen to be either flat or steep to accommodate the specific device requirements and/or parameter tuning accuracy/range.

The invention has been described above with respect to particular illustrative exemplary embodiments. It is understood that the invention is not limited to the above-described embodiments and that various changes and modifications may be made by those skilled in the relevant art without departing from the spirit and scope of the invention.

What is claimed is:

1. A device for detecting presence of a gas having a specific absorption wavelength, the device comprising:
   a photonic crystal cavity configured to sample a gas and receive light, wherein the light passes through the photonic crystal cavity, and wherein the light has a wavelength that at least partially falls within the specific absorption wavelength of the gas;
   a detector to detect the light after passing through the photonic crystal cavity;
   a generator configured for generating at least one parameter of a band gap spectrum from at least a portion of the light passing through the photonic crystal cavity, wherein the generator is configured to perform a numerical simulation within a frequency range of the photonic crystal cavity to generate a set of spectral response data points, and wherein the generator performs rational function interpolation on the set of spectral response data points to generate a spectral response of the photonic crystal cavity, and wherein the generator determines at least one parameter representing the band gap spectrum from the spectral response of the photonic crystal cavity; and
   a comparator for comparing the at least one parameter of the generated band gap spectrum with stored parameters of band gap spectrums, wherein a match of parameters indicates a presence of the gas.

2. A device according to claim 1, wherein the frequency range represents a band gap of the photonic crystal cavity.

3. A device according to claim 1, wherein the numerical simulation performed within the frequency range of the photonic crystal cavity uses a finite difference time domain (FDTD) algorithm.

4. A device according to claim 1, wherein the at least one parameter comprises frequency, width, and amplitude information.

5. A device according to claim 1, wherein the generator is configured to determine the at least one parameter by using Lorentzian regression on the spectral response of the photonic crystal cavity.

6. A device according to claim 1, further comprising:
   a pillar positioned within the photonic crystal cavity, wherein movement of the pillar can adjust the spectral output of the photonic crystal cavity.

7. A device according to claim 6, wherein the pillar is positioned by an actuator.

8. A device according to claim 6, wherein the pillar is positioned on a substrate opposite a substrate on which the photonic cavity is mounted.

9. A device for simultaneous detection of a plurality of gases, comprising:

a plurality of devices according to claim 1, wherein each photonic crystal cavity is capable of detecting the presence of at least one of the plurality of gases.

10. A device according to claim 1, wherein the gas is introduced into the photonic crystal cavity via gas inlet channels.

11. A device according to claim 1, further comprising mirrors for reflecting the light from an emitter to the photonic crystal cavity, and for reflecting light passing through the photonic crystal cavity to a detector.

12. A device according to claim 1, wherein the photonic crystal cavity is in a 3D photonic crystal.

13. A method for detecting presence of a gas having a specific absorption wavelength, the method comprising the steps of:
  emitting light having a wavelength that at least partially falls within the specific absorption wavelength of the gas;
  placing the gas within a photonic crystal cavity through which the light passes;
  detecting at least a portion of the light passing through the photonic crystal cavity;
  generating at least one parameter of a band gap spectrum from the detected portion of the light,
  wherein the step of generating at least one parameter comprises performing a numerical simulation within a frequency range of the photonic crystal cavity to generate a set of spectral response data points, performing rational function interpolation on the set of spectral response data points to generate a spectral response of the photonic crystal cavity, and determining the at least one parameter from the spectral response of the photonic crystal cavity; and
  comparing the generated at least one parameter with stored parameters of band gap spectrums, wherein a match of parameters indicates the presence of the gas.

14. A computer-readable memory medium which stores computer-executable process steps, said computer-executable process steps for causing a computer to detect presence of a gas having a specific absorption wavelength, said computer-executable process steps comprising process steps executable by the computer to perform a method according to claim 13.

15. A method for determining whether data representative of a photonic crystal meets a predetermined design standard for photonic crystal design, the method comprising the steps of:
  receiving the data representative of the photonic crystal;
  generating a frequency solution of the photonic crystal based on the data representative of the photonic crystal;
  generating a band gap spectrum from the frequency solution of the photonic crystal,
  wherein the step of generating the band gap spectrum comprises performing a numerical simulation within the frequency solution of the photonic crystal to generate a set of spectral response data points, performing rational function interpolation on the set of spectral response data points to generate a spectral response of the photonic crystal, and determining parameter information representing the band gap spectrum from the spectral response of the photonic crystal cavity; and
  determining whether the data representative of the photonic crystal meets the predetermined design standard based on the generated band gap spectrum.

16. A method according to claim 15, wherein the frequency range represents a band gap of the photonic crystal.

17. A method according to claim 15, wherein the parameter information comprises frequency, width and amplitude information.

18. A method according to claim 16, wherein the parameter information is determined by performing Lorentzian regression on the spectral response of the photonic crystal cavity.

19. A method according to claim 15, wherein the data representative of a photonic crystal represents a 3D photonic crystal.

20. A method according to claim 15, wherein the frequency solution is determined using Maxwell's equation based on the data representative of the photonic crystal.

21. A method according to claim 15, wherein if it is determined that the data representative of the photonic crystal does not meet the predetermined design standard based on the generated band gap spectrum, the data representative of the photonic crystal is modified and the steps of receiving, generating a frequency solution, generating a band gap spectrum, and determining are repeated with the modified data.

22. An apparatus for determining whether data representative of a photonic crystal meets a predetermined design standard for photonic crystal design, wherein the apparatus utilizes the numerical simulation, rational interpolation and parameter determination of claim 15 to determine whether the data representative of a photonic crystal meets the predetermined design standard for photonic crystal design.

23. A computer-readable memory medium which stores computer-executable process steps, said computer-executable process steps for causing a computer to determine whether data representative of a photonic crystal meets a predetermined design standard for photonic crystal design, said computer-executable process steps comprising process steps executable by the computer to perform a method according to claim 15.

24. A device for characterizing a photonic crystal, the device comprising:
  an emitter configured for emitting light such that the light is incident upon and passes through the photonic crystal;
  a detector configured for detecting at least a portion of the light that passes through the photonic crystal;
  a generator configured for generating a band gap spectrum from the detected portion of the light,
  wherein the generator is configured to perform a numerical simulation within a frequency range of the photonic crystal to generate a set of spectral response data points, and wherein the generator performs rational function interpolation on the set of spectral response data points to generate a spectral response of the photonic crystal, and wherein the generator determines parameter information representing the band gap spectrum from the spectral response of the photonic crystal; and
  a comparator for comparing the generated band gap spectrum with stored band spectrums for characterizing the photonic crystal.

25. A device according to claim 24, wherein the frequency range represents a band gap of the photonic crystal.

26. A device according to claim 24, wherein the parameter information comprises frequency, width and amplitude information.

27. A device according to claim 24, wherein the parameter information is determined by performing Lorentzian regression on the spectral response of the photonic crystal cavity.

28. A device according to claim 24, wherein the data representative of a photonic crystal represents a 3D photonic crystal.

29. A device according to claim 24, wherein the frequency solution is determined using Maxwell's equation based on the data representative of the photonic crystal.

30. A method for characterizing a photonic crystal, the method comprising the steps of:

emitting light such that the light is incident upon and passes through the photonic crystal;

detecting at least a portion of the light that passes through the photonic crystal;

generating a band gap spectrum from the detected portion of the light, wherein the step of generating the band gap spectrum comprises:

performing a numerical simulation within a frequency range of the photonic crystal to generate a set of spectral response data points;

performing rational function interpolation on the set of spectral response data points to generate a spectral response of the photonic crystal; and determining parameter information representing the band gap spectrum from the spectral response of the photonic crystal; and comparing the generated band gap spectrum with stored band gap spectrums, wherein matching generated and stored band gap spectrums characterize the photonic crystal.

31. A computer-readable memory medium which stores computer-executable process steps, said computer-executable process steps for causing a computer to characterize a photonic crystal, said computer-executable process steps comprising process steps executable by the computer to perform a method according to claim 30.

* * * * *

UNITED STATES PATENT AND TRADEMARK OFFICE
CERTIFICATE OF CORRECTION

PATENT NO.       : 7,352,466 B2
APPLICATION NO.  : 11/157042
DATED            : April 1, 2008
INVENTOR(S)      : Jiang-Rong Cao et al.

It is certified that error appears in the above-identified patent and that said Letters Patent is hereby corrected as shown below:

IN THE DRAWINGS
    Sheet 28, Figure 34, "CRYTAL" in step S3402 should read --CRYSTAL--.

COLUMN 16
    Line 40, "©)" should read --(c)--.

COLUMN 17
    Line 9, "then" should read --then be--;
    Line 18, "proportional" should read --proportional to--; and
    Line 28, "through out" should read --throughout--.

COLUMN 18
    Line 11, "though" should read --through--.

COLUMN 20
    Line 39, "is a" should be deleted.

COLUMN 21
    Line 5, "he" should read --the--.

COLUMN 27
    Line 18, "One" should read --On--; and
    Line 40, "©)" should read --(c)--.

COLUMN 29
    Line 7, "oppose" should read --opposed--.

UNITED STATES PATENT AND TRADEMARK OFFICE
CERTIFICATE OF CORRECTION

PATENT NO. : 7,352,466 B2
APPLICATION NO. : 11/157042
DATED : April 1, 2008
INVENTOR(S) : Jiang-Rong Cao et al.

It is certified that error appears in the above-identified patent and that said Letters Patent is hereby corrected as shown below:

COLUMN 36
Line 4, "claim 16," should read --claim 15,--.

Signed and Sealed this

Twenty-third Day of September, 2008

JON W. DUDAS
*Director of the United States Patent and Trademark Office*